United States Patent
Anderson et al.

(10) Patent No.: US 10,116,563 B1
(45) Date of Patent: Oct. 30, 2018

(54) SYSTEM AND METHOD FOR AUTOMATICALLY UPDATING DATA PACKET METADATA

(71) Applicant: Pearson Education, Inc., New York, NY (US)

(72) Inventors: Jacob Anderson, Centennial, CO (US); Yun Jin Rho, Acton, MA (US)

(73) Assignee: PEARSON EDUCATION, INC., New York, NY (US)

( * ) Notice: Subject to any disclaimer, the term of this patent is extended or adjusted under 35 U.S.C. 154(b) by 20 days.

(21) Appl. No.: 15/360,657

(22) Filed: Nov. 23, 2016

Related U.S. Application Data

(63) Continuation-in-part of application No. 15/236,103, filed on Aug. 12, 2016, which is a
(Continued)

(51) Int. Cl.
| | | |
|---|---|---|
| H04L 12/741 | (2013.01) | |
| H04L 29/08 | (2006.01) | |
| H04L 29/06 | (2006.01) | |

(52) U.S. Cl.
CPC .............. *H04L 45/74* (2013.01); *H04L 67/22* (2013.01); *H04L 67/306* (2013.01); *H04L 69/22* (2013.01)

(58) Field of Classification Search
CPC ... H04L 41/0816; H04L 47/805; H04L 63/20; H04L 65/1036; H04L 12/6402; H04L 65/1033; H04L 65/103; H04L 67/1078; H04L 67/16; H04L 12/2838; H04L 63/02; H04L 65/1023; H04L 67/2842; H04L 67/1095; H04L 12/2801; H04L 29/06095;
(Continued)

(56) References Cited

U.S. PATENT DOCUMENTS

| 6,049,777 A | 4/2000 | Sheena et al. |
| 6,112,186 A | 8/2000 | Bergh et al. |
| (Continued) | | |

FOREIGN PATENT DOCUMENTS

WO   2009/149262 A1   12/2009

OTHER PUBLICATIONS

International Search Report and Written Opinion dated Feb. 23, 2016, for International Application No. PCT/US2015/058467, 12 pages.

*Primary Examiner* — Mounir Moutaouakil
(74) *Attorney, Agent, or Firm* — Kilpatrick Townsend & Stockton LLP

(57) ABSTRACT

Systems and methods for accelerated stabilization of data packet metadata are disclosed herein. The system can include a memory having a content database and a user profile database. The system can include a user device having a first network interface and a first I/O subsystem. The system can include one or more servers. The one or more servers can: retrieve data packet metadata for a data packet; determine that the data packet metadata is unstable; identify a set of potential recipients of the data packet; select one of the set of potential recipients as the recipient of the data packet; provide the data packet to the recipient of the data packet; receive a response from the recipient to the provided data packet; and automatically update the data packet metadata based on the response received from the recipient.

17 Claims, 19 Drawing Sheets

Related U.S. Application Data continuation-in-part of application No. 14/927,115, filed on Oct. 29, 2015, said application No. 15/236,103 is a continuation-in-part of application No. 14/927,145, filed on Oct. 29, 2015, which is a continuation-in-part of application No. 14/927,170, filed on Oct. 29, 2015, which is a continuation-in-part of application No. 14/928,152, filed on Oct. 30, 2015, now Pat. No. 9,667,321.

(60) Provisional application No. 62/320,213, filed on Apr. 8, 2016, provisional application No. 62/211,156, filed on Aug. 28, 2015, provisional application No. 62/072,910, filed on Oct. 30, 2014, provisional application No. 62/073,751, filed on Oct. 31, 2014, provisional application No. 62/072,914, filed on Oct. 30, 2014, provisional application No. 62/073,814, filed on Oct. 31, 2014.

(58) Field of Classification Search
CPC ..... H04L 67/12; H04L 12/1453; H04L 12/66; H04L 67/104; H04L 63/10; H04L 63/0281; H04L 65/40; H04L 65/102; H04L 67/10; H04L 47/2491; H04L 41/32; H04L 45/302; H04L 2012/2849; H04L 65/4084; H04L 41/5019; H04N 5/445; H04N 21/482; H04N 21/632; H04N 21/258; H04N 21/6543; H04N 21/47202; H04N 21/6373; H04N 21/6371; H04N 21/43615; H04N 21/454; G05B 13/02; G06Q 40/12; G06Q 30/04; G06Q 30/0215; G06Q 30/0226; G06Q 20/10; G05F 1/66; H04W 12/08; H04W 52/265; G06F 21/10; G06F 2221/07; G06F 21/6245; Y02D 30/30
See application file for complete search history.

(56) References Cited

U.S. PATENT DOCUMENTS

| | | | |
|---|---|---|---|
| 6,470,170 B1* | 10/2002 | Chen | G09B 5/14 434/350 |
| 6,772,202 B2 | 8/2004 | Wright | |
| 7,184,844 B2 | 2/2007 | Dausch | |
| 7,240,235 B2 | 7/2007 | Lewalski-Brechter | |
| 7,653,739 B1 | 1/2010 | Kalker | |
| 7,747,369 B2 | 6/2010 | Koehrsen | |
| 7,828,552 B2 | 11/2010 | Shute | |
| 8,249,868 B2 | 8/2012 | Lloyd | |
| 8,550,822 B2 | 10/2013 | Templin | |
| 8,666,740 B2 | 3/2014 | Lloyd | |
| 8,774,043 B2 | 7/2014 | Vilke | |
| 9,043,433 B2 | 5/2015 | Backholm | |
| 9,246,822 B2 | 1/2016 | Vilke | |
| 9,654,175 B1 | 5/2017 | Lowrie | |
| 2002/0071393 A1 | 6/2002 | Musoll | |
| 2002/0184020 A1 | 12/2002 | Shinoda | |
| 2004/0153373 A1 | 8/2004 | Song et al. | |
| 2005/0234763 A1 | 10/2005 | Pinto | |
| 2005/0288954 A1 | 12/2005 | McCarthy et al. | |
| 2006/0040247 A1 | 2/2006 | Templin | |
| 2006/0117077 A1 | 6/2006 | Kiiveri | |
| 2006/0204040 A1 | 9/2006 | Freeman | |
| 2006/0212386 A1 | 9/2006 | Willey | |
| 2006/0286533 A1 | 12/2006 | Hansen | |
| 2007/0172808 A1 | 7/2007 | Capone | |
| 2008/0015793 A1 | 1/2008 | Ben-Menahem | |
| 2008/0319829 A1 | 12/2008 | Hunt | |
| 2009/0037398 A1 | 2/2009 | Horvitz | |
| 2009/0268830 A1 | 10/2009 | Birru | |
| 2010/0010878 A1 | 1/2010 | Pinto | |
| 2010/0010942 A1* | 1/2010 | Kobayashi | G10H 1/0008 706/12 |
| 2010/0120422 A1 | 5/2010 | Cheung | |
| 2010/0190142 A1 | 7/2010 | Gal | |
| 2011/0040896 A1 | 2/2011 | DeCusatis et al. | |
| 2011/0087877 A1 | 4/2011 | Dagg | |
| 2011/0208695 A1* | 8/2011 | Anand | G06F 17/30578 707/610 |
| 2011/0212430 A1* | 9/2011 | Smithmier | G09B 5/06 434/322 |
| 2011/0283355 A1 | 11/2011 | Livshits | |
| 2012/0265783 A1 | 10/2012 | Kenedy | |
| 2012/0314599 A1 | 12/2012 | Vilke | |
| 2013/0163837 A1 | 6/2013 | Zabair | |
| 2013/0226839 A1 | 8/2013 | Archambeau | |
| 2013/0266925 A1 | 10/2013 | Nunamaker, Jr. | |
| 2013/0288222 A1* | 10/2013 | Stacy | G09B 5/00 434/362 |
| 2014/0130076 A1 | 5/2014 | Moore et al. | |
| 2014/0141888 A1 | 5/2014 | Pavlish | |
| 2014/0157371 A1* | 6/2014 | Le Chevalier | G06F 17/30563 726/4 |
| 2014/0254376 A1 | 9/2014 | Vilke | |
| 2014/0286337 A1* | 9/2014 | Dolson | H04L 43/12 370/392 |
| 2015/0052559 A1* | 2/2015 | Leong | G06F 3/0482 725/44 |
| 2015/0134694 A1 | 5/2015 | Burke | |
| 2015/0215841 A1* | 7/2015 | Hsu | H04L 43/12 370/328 |
| 2015/0269941 A1 | 9/2015 | Jones | |
| 2015/0316383 A1 | 11/2015 | Donikian | |
| 2015/0317582 A1 | 11/2015 | Nath | |
| 2015/0332372 A1 | 11/2015 | Hariri | |
| 2015/0347508 A1 | 12/2015 | Lang | |
| 2015/0356420 A1 | 12/2015 | Byron | |
| 2016/0124999 A1 | 5/2016 | Brenes et al. | |
| 2016/0127010 A1 | 5/2016 | Rho et al. | |
| 2016/0127244 A1 | 5/2016 | Brenes et al. | |
| 2016/0127248 A1 | 5/2016 | Brenes et al. | |
| 2017/0359236 A1* | 12/2017 | Circlaeys | H04L 43/16 |

* cited by examiner

SYSTEM AND METHOD FOR AUTOMATICALLY UPDATING DATA PACKET METADATA

RELATED APPLICATIONS

This application is a Continuation-in-Part of U.S. application Ser. No. 15/236,103, filed on Aug. 12, 2016, and entitled "SYSTEMS AND METHODS FOR DATA PACKET METADATA STABILIZATION", which claims the benefit of U.S. Provisional Application No. 62/320,213, filed on Apr. 8, 2016, and entitled "ADAPTIVE PATHWAYS AND COGNITIVE TUTORING"; U.S. application Ser. No. 15/236,103 claims the benefit of U.S. Provisional Application No. 62/211,156, filed on Aug. 28, 2015, and entitled "DATA-ENABLED SUCCESS AND PROGRESSION SYSTEM"; U.S. application Ser. No. 15/236,103 is a Continuation-in-Part of U.S. application Ser. No. 14/927,115, filed on Oct. 29, 2015, and entitled "SYSTEM AND METHOD FOR INCREASING DATA TRANSMISSION RATES THROUGH A CONTENT DISTRIBUTION NETWORK", which claims the benefit of U.S. Provisional Application No. 62/072,910, filed on Oct. 30, 2014; U.S. application Ser. No. 15/236,103 is a Continuation-in-Part of U.S. application Ser. No. 14/927,145, filed on Oct. 29, 2015, and entitled "SYSTEM AND METHOD FOR INCREASING DATA TRANSMISSION RATES THROUGH A CONTENT DISTRIBUTION NETWORK WITH CUSTOMIZED AGGREGATIONS", which claims the benefit of U.S. Provisional Application No. 62/073,751, filed on Oct. 31, 2014; U.S. application Ser. No. 15/236,103 is a Continuation-in-Part of U.S. application Ser. No. 14/927,170, filed on Oct. 29, 2015, and entitled "CONTENT DATABASE GENERATION", which claims the benefit of U.S. Provisional Application No. 62/072,914, filed on Oct. 30, 2014; U.S. application Ser. No. 15/236,103 is a Continuation-in-Part of U.S. application Ser. No. 14/928,152, filed on Oct. 30, 2015, and entitled "PREDICTIVE RECOMMENDATION ENGINE", which claims the benefit of U.S. Provisional Application No. 62/073,814, filed on Oct. 31, 2014, the entirety of each of which is hereby incorporated by reference herein.

BACKGROUND

A computer network or data network is a telecommunications network which allows computers to exchange data. In computer networks, networked computing devices exchange data with each other along network links (data connections). The connections between nodes are established using either cable media or wireless media. The best-known computer network is the Internet.

Network computer devices that originate, route and terminate the data are called network nodes. Nodes can include hosts such as personal computers, phones, servers as well as networking hardware. Two such devices can be said to be networked together when one device is able to exchange information with the other device, whether or not they have a direct connection to each other.

Computer networks differ in the transmission media used to carry their signals, the communications protocols to organize network traffic, the network's size, topology and organizational intent. In most cases, communications protocols are layered on (i.e. work using) other more specific or more general communications protocols, except for the physical layer that directly deals with the transmission media.

BRIEF SUMMARY

One aspect of the present disclosure relates to a system for accelerated stabilization of data packet metadata. The system includes a memory. The memory can include: a content database including a plurality of data packets and metadata identifying an attribute of an associated data packet; and a user profile database including user history data identifying an attribute of an associated user. In some embodiments, each of the plurality of data packets is associated with unique metadata, and in some embodiments, each user is associated with unique user history data. The system can include a user device. The user device can include: a first network interface that can exchange data via a communication network; and a first I/O subsystem that can convert electrical signals to user interpretable outputs via a user interface. The system can include one or more servers. The one or more servers can: identify a data packet that includes content for delivery to a user device; retrieve data packet metadata from the content database of the memory, which data packet metadata identifies a difficulty level of the data packet; determine that the data packet metadata is unstable; identify a set of potential recipients of the data packet; select one of the set of potential recipients as the recipient of the data packet based on a correspondence between the data packet metadata and user data for the recipient; provide the data packet to the recipient of the data packet; receive a response from the recipient to the provided data packet; and automatically update the data packet metadata based on the response received from the recipient.

In some embodiments, determining that the data packet metadata is unstable includes retrieving a stability threshold, which stability threshold identifies a minimum number of received user responses subsequent to the providing of the data packet. In some embodiments, determining that the data packet metadata is unstable includes extracting a value indicative of the number of received responses subsequent to the providing of the data packet from the data packet metadata; and comparing the stability threshold and the value indicative of the number of received responses subsequent to the providing of the data packet from the metadata.

In some embodiments, the one or more servers include a response processor that can translate the received response into an observable. In some embodiments, translating the received response into an observable includes evaluating the received response to determine if the received response is a desired response. In some embodiments, updating the data packet metadata includes updating a model of the difficulty of the data packet. In some embodiments, the model of the difficulty of the data packet is a piecewise Gaussian distribution model.

In some embodiments, the one or more servers can repeatedly: identify the set of potential recipients of the data packet; select one of the set of potential recipients as the recipient of the data packet based on a correspondence between the data packet metadata and user data for the recipient; provide the data packet to the recipient of the data packet; receive a response from the recipient to the provided data packet; and automatically update the data packet metadata based on the response received from the recipient, until the one or more servers determine that the data packet metadata is stable. In some embodiments, the one or more servers can add an indicator of stability to the data packet metadata when the one or more servers determine that the data packet metadata is stable.

In some embodiments, the one or more servers can: automatically generate an alert including an indicator of the stability of the data packet metadata when the one or more servers determine that the data packet metadata is stable; and send the alert to a supervisor device. In some embodiments, the alert includes computer code to direct the supervisor device to automatically launch an application that displays an indicator of the metadata stability.

One aspect of the present disclosure relates to a method for accelerated stabilization of data packet metadata. The method includes: (a) identifying a data packet that includes content for delivery to a user device; (b) retrieving data packet metadata from a memory including a content library database; (c) determining that the data packet metadata is unstable; (d) identifying a set of potential recipients of the data packet; (e) selecting one of the set of potential recipients as the recipient of the data packet based on a correspondence between the data packet metadata and user data for the recipient; (f) providing the data packet to the recipient of the data packet; (g) receiving a response from the recipient to the provided data packet; and (h) automatically updating the data packet metadata based on the response received from the recipient. In some embodiments, the data packet metadata identifies a difficulty level of the data packet.

In some embodiments, the method includes, repeating steps (a)-(h) until the data packet metadata is stable. In some embodiments, selecting one of the set of potential recipients as the recipient of the data packet includes: (i) selecting one potential recipient of the set of potential recipients for analysis; (ii) determining a load level for the selected one potential recipient of the set of potential recipients; and (iii) adding a value indicative of acceptability when a predicted load level is less than a load threshold.

In some embodiments, selecting one potential recipient of the set of potential recipients as the recipient of the data packet includes generating a predicted load value that is based off of the determined load level for the selected one potential recipient of the set of potential recipients update to include the load effect of receipt of the data packet. In some embodiments, the method includes: retrieving the load threshold; comparing the predicted load value to the load threshold; and removing the selected one potential recipient of the set of potential recipients from the set of potential recipient when the predicted load level is greater than the load threshold.

In some embodiments, the method includes repeating steps (i)-(iii) when it is determined that there are additional potential recipients in the set of potential recipients that have not been selected in step (i). In some embodiments, the method includes designating a recipient associated with the value indicative of acceptability when it is determined that there are no additional potential recipients in the set of potential recipients that have not been selected in step (i). In some embodiments, determining that the data packet metadata is unstable includes retrieving a stability threshold that identifies a minimum number of received user responses subsequent to the providing of the data packet. In some embodiments, determining that the data packet metadata is unstable includes extracting a value indicative of the number of received responses subsequent to the providing of the data packet from the data packet metadata; and comparing the stability threshold and the value indicative of the number of received responses subsequent to the providing of the data packet from the metadata.

One aspect of the present disclosure relates to a system for content provisioning via the automatic determination of a content attribute. The system includes a memory including a content database containing a plurality of data packets and metadata identifying an attribute of an associated data packet and a user profile database including user history data identifying an attribute of an associated user. In some embodiments, each of the plurality of data packets is associated with unique metadata. In some embodiments, each user is associated with unique user history data. The system can include a user device that can include: a first network interface that can exchange data via a communication network; and a first I/O subsystem that can convert electrical signals to user interpretable outputs via a user interface. The system can include one or more servers. The one or more severs can: receive a response from a user via a user device, which response is to a previously provided data packet; identify the previously provided data packet; retrieve data packet metadata, which packet metadata includes at least one attribute value identifying an attribute of the data packet; translate the received response into an observable; update the data packet metadata based on the observable; and provide the received data packet to a user based on the updated data packet metadata.

In some embodiments, the data packet metadata includes a model of the difficulty level of the data packet. In some embodiments, the model is based on a localized distribution. In some embodiments, the localized distribution includes a piecewise Gaussian distribution. In some embodiments, the mode of the Gaussian distribution corresponds to a difficulty level of the data packet. In some embodiments, the Gaussian distribution is a piecewise Gaussian distribution.

In some embodiments, the Gaussian distribution is defined in part by an error value corresponding to the width of the Gaussian distribution. In some embodiments, updating the update the data packet metadata based on the observable includes updating the Gaussian distribution. In some embodiments, updating the Gaussian distribution includes updating the mode of the Gaussian distribution and the error value of the Gaussian distribution.

In some embodiments, the update of the Gaussian distribution varies based on whether the received response is a desired response or an undesired response. In some embodiments, providing the received data packet to the user device based on the updated data packet metadata of the received data packet includes selecting a recipient of the received data packet. In some embodiments, the recipient of the received data packet is selected based on a comparison of the data packet metadata and user metadata associated with the recipient.

One aspect of the present disclosure relates to a method for automatically updating data packet metadata. The method includes: receiving a response from a user via a user device, which response is to a previously provided data packet; identifying the previously provided data packet; retrieving data packet metadata, which data packet metadata includes at least one attribute value identifying an attribute of the data packet; translating the received response into an observable; updating the data packet metadata based on the observable; and providing the received data packet to a user based on the updated data packet metadata.

In some embodiments, the data packet metadata includes a model of the difficulty level of the data packet. In some embodiments, the model is based on a localized distribution.

In some embodiments, the mode of the localized distribution corresponds to a difficulty level of the data packet.

In some embodiments, the localized distribution is a Gaussian distribution. In some embodiments, the Gaussian distribution is defined in part by an error value corresponding to the width of the Gaussian distribution. In some embodiments, updating the data packet metadata based on the observable includes updating the Gaussian distribution. In some embodiments, updating the Gaussian distribution includes updating the mode of the Gaussian distribution and the error value of the Gaussian distribution. In some embodiments, the update of the Gaussian distribution varies based on whether the received response is a desired response or an undesired response.

In some embodiments, providing the received data packet to the user device based on the updated data packet metadata of the received data packet includes selecting a recipient of the received data packet. In some embodiments, the recipient of the received data packet is selected based on a comparison of the data packet metadata and user metadata associated with the recipient.

One aspect of the present disclosure relates to a system for content provisioning via the automatic determination of a content attribute. The system includes: memory including a content database including a plurality of data packets and metadata identifying an attribute of an associated data packet. In some embodiments, each of the plurality of data packets is associated with unique metadata. The memory includes a user profile database including user history data identifying an attribute of an associated user. In some embodiments, each user is associated with unique user history data. The system includes a user device including: a first network interface that can exchange data via a communication network; and a first I/O subsystem that can convert electrical signals to user interpretable outputs via a user interface. The system includes one or more servers. The one or more server can, in some embodiments, be controlled according to stored computer code. The server can: receive a data packet including content for providing to a user via a user device; retrieve data packet metadata associated with the data packet, which data packet metadata includes at least one attribute value identifying an attribute of the data packet; identify a data packet content network relevant to the received data packet, which data packet content network and the data packet relate to a common subject; determine a position within the data packet network for placement of the data packet within the data packet content network; generate a combined attribute value based on attribute values of similarly placed data packets in the content network; and update the data packet metadata of the received data packet, which data packet metadata is updated to include an attribute value matching the generating combined attribute value of the similarly placed data packets in the content network.

In some embodiments, the one or more servers can further determine when the difficulty of the received data packet is identified in the retrieved data packet metadata. In some embodiments, the one or more servers can further identify a plurality of similarly positioned data packets in the identified data packet content network. In some embodiments, the plurality of similarly positioned data packets in the identified data packet content network are identified based on the determined position for placement of the data packet within the data packet network.

In some embodiments, the one or more servers can further retrieve attribute information for the identified plurality of similarly positioned data packets. In some embodiments, the attribute information identifies a difficulty level for each of the plurality of similarly positioned data packets. In some embodiments, the combined attribute value is generated based on difficulty levels for the plurality of similarly positioned data packets.

In some embodiments, the one or more servers can further provide the received data packet to the user device based on the updated data packet metadata of the received data packet. In some embodiments, providing the received data packet to the user device based on the updated data packet metadata of the received data packet includes selecting a recipient of the received data packet. In some embodiments, the recipient of the received data packet is selected based on a comparison of the data packet metadata and user metadata associated with the recipient.

One aspect of the present disclosure relates to a method for content provisioning via the automatic determination of a content attribute. The method includes: receiving a data packet including content for providing to a user via a user device; retrieving data packet metadata associated with the data packet, which data packet metadata includes at least one attribute value identifying an attribute of the data packet; identifying a data packet content network relevant to the received data packet, which data packet content network and the data packet relate to a common subject; determining a position within the data packet network for placement of the data packet within the data packet content network; generating a combined attribute value based on attribute values of similarly placed data packets in the content network; and updating the data packet metadata of the received data packet. In some embodiments, the data packet metadata is updated to include an attribute value matching the generating combined attribute value of the similarly placed data packets in the content network.

In some embodiments, the method includes determining that the difficulty of the received data packet is not identified in the retrieved data packet metadata. In some embodiments, the method includes identifying a plurality of similarly positioned data packets in the identified data packet content network. In some embodiments, the plurality of similarly positioned data packets in the identified data packet content network are identified based on the determined position for placement of the data packet within the data packet network.

In some embodiments, the method includes retrieving attribute information for the identified plurality of similarly positioned data packets. In some embodiments, the attribute information identifies a difficulty level for each of the plurality of similarly positioned data packets. In some embodiments, the combined attribute value is generated based on difficulty levels for the plurality of similarly positioned data packets.

In some embodiments, the method includes providing the received data packet to the user device based on the updated data packet metadata of the received data packet. In some embodiments, providing the received data packet to the user device based on the updated data packet metadata of the received data packet includes selecting a recipient of the received data packet. In some embodiments, the recipient of the received data packet is selected based on a comparison of the data packet metadata and user metadata associated with the recipient.

Further areas of applicability of the present disclosure will become apparent from the detailed description provided hereinafter. It should be understood that the detailed description and specific examples, while indicating various embodi-

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides illustrative embodiment(s) only and is not intended to limit the scope, applicability or configuration of the disclosure. Rather, the ensuing description of the illustrative embodiment(s) will provide those skilled in the art with an enabling description for implementing a preferred exemplary embodiment. It is understood that various changes can be made in the function and arrangement of elements without departing from the spirit and scope as set forth in the appended claims.

This application is related to U.S. application Ser. No. 15/236,196, filed on Aug. 12, 2016, and entitled "SYSTEMS AND METHODS OF EVENT-BASED CONTENT PROVISIONING"; U.S. application Ser. No. 15/236,275, filed on Aug. 12, 2016, and entitled "SYSTEM AND METHOD FOR AUTOMATIC CONTENT AGGREGATION GENERATION"; and U.S. application Ser. No. 15/236,238, filed on Aug. 12, 2016, and entitled "SYSTEM AND METHOD FOR CONTENT PROVISIONING WITH DUAL RECOMMENDATION ENGINES", the entirety of each of which is hereby incorporated by reference herein.

Figure 1:
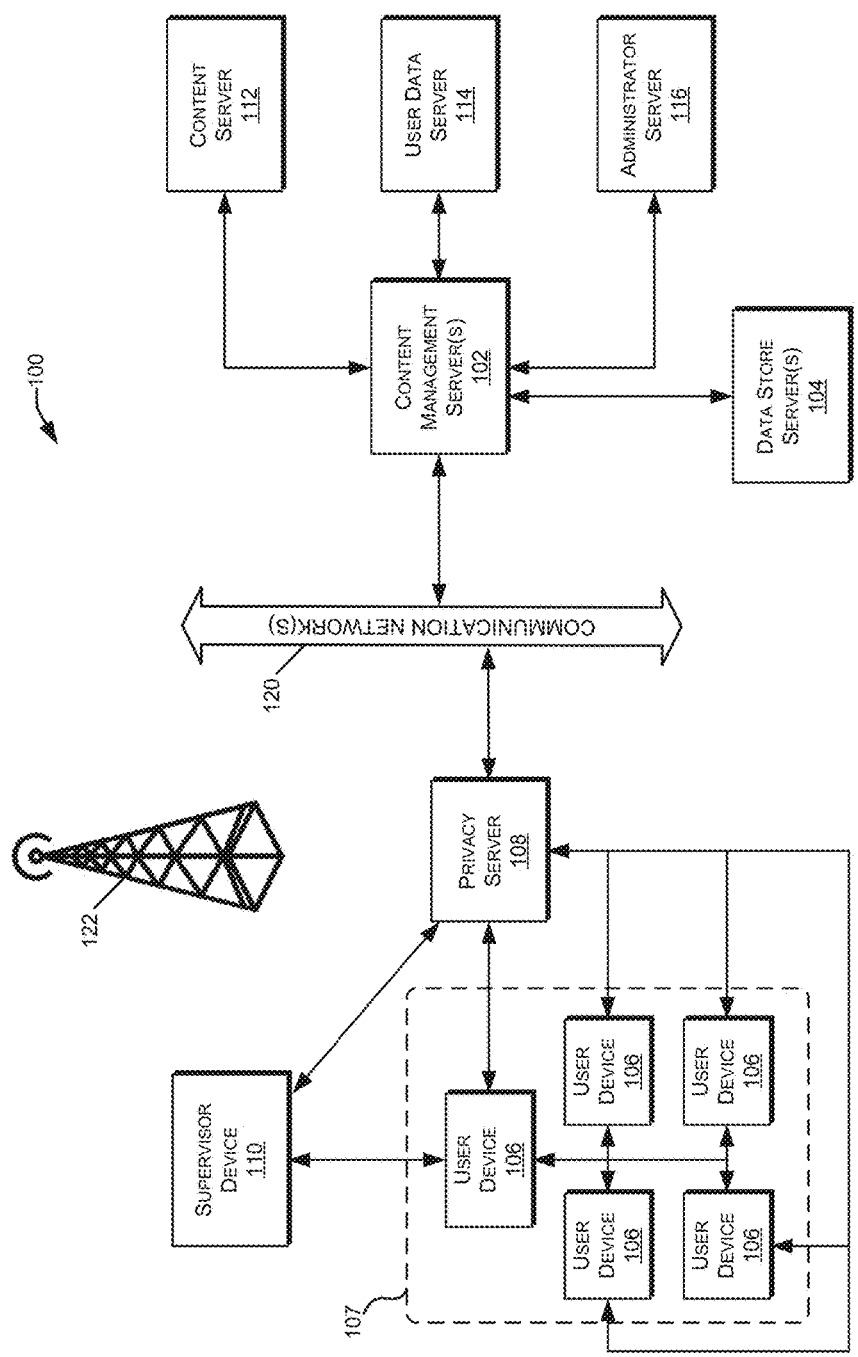
FIG. 1 is a block diagram illustrating an example of a content distribution network.

With reference now to FIG. 1, a block diagram is shown illustrating various components of a content distribution network (CDN) 100 which implements and supports certain embodiments and features described herein. In some embodiments, the content distribution network 100 can comprise one or several physical components and/or one or several virtual components such as, for example, one or several cloud computing components. In some embodiments, the content distribution network 100 can comprise a mixture of physical and cloud computing components.

Content distribution network 100 may include one or more content management servers 102. As discussed below in more detail, content management servers 102 may be any desired type of server including, for example, a rack server, a tower server, a miniature server, a blade server, a mini rack server, a mobile server, an ultra-dense server, a super server, or the like, and may include various hardware components, for example, a motherboard, a processing unit, memory systems, hard drives, network interfaces, power supplies, etc. Content management server 102 may include one or more server farms, clusters, or any other appropriate arrangement and/or combination of computer servers. Content management server 102 may act according to stored instructions located in a memory subsystem of the server 102, and may run an operating system, including any commercially available server operating system and/or any other operating systems discussed herein.

The content distribution network 100 may include one or more data store servers 104, such as database servers and file-based storage systems. The database servers 104 can access data that can be stored on a variety of hardware components. These hardware components can include, for example, components forming tier 0 storage, components forming tier 1 storage, components forming tier 2 storage, and/or any other tier of storage. In some embodiments, tier 0 storage refers to storage that is the fastest tier of storage in the database server 104, and particularly, the tier 0 storage is the fastest storage that is not RAM or cache memory. In some embodiments, the tier 0 memory can be embodied in solid state memory such as, for example, a solid-state drive (SSD) and/or flash memory.

In some embodiments, the tier 1 storage refers to storage that is one or several higher performing systems in the memory management system, and that is relatively slower than tier 0 memory, and relatively faster than other tiers of memory. The tier 1 memory can be one or several hard disks that can be, for example, high-performance hard disks. These hard disks can be one or both of physically or communicatingly connected such as, for example, by one or several fiber channels. In some embodiments, the one or several disks can be arranged into a disk storage system, and specifically can be arranged into an enterprise class disk storage system. The disk storage system can include any desired level of redundancy to protect data stored therein, and in one embodiment, the disk storage system can be made with grid architecture that creates parallelism for uniform allocation of system resources and balanced data distribution.

In some embodiments, the tier 2 storage refers to storage that includes one or several relatively lower performing systems in the memory management system, as compared to the tier 1 and tier 2 storages. Thus, tier 2 memory is relatively slower than tier 1 and tier 0 memories. Tier 2 memory can include one or several SATA-drives or one or several NL-SATA drives.

In some embodiments, the one or several hardware and/or software components of the database server 104 can be arranged into one or several storage area networks (SAN), which one or several storage area networks can be one or several dedicated networks that provide access to data storage, and particularly that provide access to consolidated, block level data storage. A SAN typically has its own network of storage devices that are generally not accessible through the local area network (LAN) by other devices. The SAN allows access to these devices in a manner such that these devices appear to be locally attached to the user device.

Data stores 104 may comprise stored data relevant to the functions of the content distribution network 100. Illustrative examples of data stores 104 that may be maintained in certain embodiments of the content distribution network 100 are described below in reference to FIG. 3. In some embodiments, multiple data stores may reside on a single server 104, either using the same storage components of server 104 or using different physical storage components to assure data security and integrity between data stores. In other embodiments, each data store may have a separate dedicated data store server 104.

Content distribution network 100 also may include one or more user devices 106 and/or supervisor devices 110. User devices 106 and supervisor devices 110 may display content received via the content distribution network 100, and may support various types of user interactions with the content. User devices 106 and supervisor devices 110 may include mobile devices such as smartphones, tablet computers, personal digital assistants, and wearable computing devices. Such mobile devices may run a variety of mobile operating systems, and may be enabled for Internet, e-mail, short message service (SMS), Bluetooth®, mobile radio-frequency identification (M-RFID), and/or other communication protocols. Other user devices 106 and supervisor devices 110 may be general purpose personal computers or special-purpose computing devices including, by way of example, personal computers, laptop computers, workstation computers, projection devices, and interactive room display systems. Additionally, user devices 106 and supervisor devices 110 may be any other electronic devices, such as thin-client computers, Internet-enabled gaming systems, business or home appliances, and/or a personal messaging devices, capable of communicating over network(s) 120.

In different contexts of content distribution networks 100, user devices 106 and supervisor devices 110 may correspond to different types of specialized devices, for example, student devices and teacher devices in an educational network, employee devices and presentation devices in a company network, different gaming devices in a gaming network, etc.

In some embodiments, user devices 106 and supervisor devices 110 may operate in the same physical location 107, such as a classroom or conference room. In such cases, the devices may contain components that support direct communications with other nearby devices, such as a wireless transceivers and wireless communications interfaces, Ethernet sockets or other Local Area Network (LAN) interfaces, etc. In other implementations, the user devices 106 and supervisor devices 110 need not be used at the same location 107, but may be used in remote geographic locations in which each user device 106 and supervisor device 110 may use security features and/or specialized hardware (e.g., hardware-accelerated SSL and HTTPS, WS-Security, firewalls, etc.) to communicate with the content management server 102 and/or other remotely located user devices 106. Additionally, different user devices 106 and supervisor devices 110 may be assigned different designated roles, such as presenter devices, teacher devices, administrator devices, or the like, and in such cases the different devices may be provided with additional hardware and/or software components to provide content and support user capabilities not available to the other devices.

The content distribution network 100 also may include a privacy server 108 that maintains private user information at the privacy server 108 while using applications or services hosted on other servers. For example, the privacy server 108 may be used to maintain private data of a user within one jurisdiction even though the user is accessing an application hosted on a server (e.g., the content management server 102) located outside the jurisdiction. In such cases, the privacy server 108 may intercept communications between a user device 106 or supervisor device 110 and other devices that include private user information. The privacy server 108 may create a token or identifier that does not disclose the private information and may use the token or identifier when communicating with the other servers and systems, instead of using the user's private information.

As illustrated in FIG. 1, the content management server 102 may be in communication with one or more additional servers, such as a content server 112, a user data server 112, and/or an administrator server 116. Each of these servers may include some or all of the same physical and logical components as the content management server(s) 102, and in some cases, the hardware and software components of these servers 112-116 may be incorporated into the content management server(s) 102, rather than being implemented as separate computer servers.

Content server 112 may include hardware and software components to generate, store, and maintain the content resources for distribution to user devices 106 and other devices in the network 100. For example, in content distribution networks 100 used for professional training and educational purposes, content server 112 may include data stores of training materials, presentations, plans, syllabi, reviews, evaluations, interactive programs and simulations, course models, course outlines, and various training interfaces that correspond to different materials and/or different types of user devices 106. In content distribution networks 100 used for media distribution, interactive gaming, and the like, a content server 112 may include media content files such as music, movies, television programming, games, and advertisements.

User data server 114 may include hardware and software components that store and process data for multiple users relating to each user's activities and usage of the content distribution network 100. For example, the content management server 102 may record and track each user's system usage, including his or her user device 106, content resources accessed, and interactions with other user devices 106. This data may be stored and processed by the user data server 114, to support user tracking and analysis features. For instance, in the professional training and educational contexts, the user data server 114 may store and analyze each user's training materials viewed, presentations attended, courses completed, interactions, evaluation results, and the like. The user data server 114 may also include a repository for user-generated material, such as evaluations and tests completed by users, and documents and assignments prepared by users. In the context of media distribution and interactive gaming, the user data server 114 may store and process resource access data for multiple users (e.g., content titles accessed, access times, data usage amounts, gaming histories, user devices and device types, etc.).

Administrator server 116 may include hardware and software components to initiate various administrative functions at the content management server 102 and other components within the content distribution network 100. For example, the administrator server 116 may monitor device status and performance for the various servers, data stores, and/or user devices 106 in the content distribution network 100. When necessary, the administrator server 116 may add or remove devices from the network 100, and perform device maintenance such as providing software updates to the devices in the network 100. Various administrative tools on the administrator server 116 may allow authorized users to set user access permissions to various content resources, monitor resource usage by users and devices 106, and perform analyses and generate reports on specific network users and/or devices (e.g., resource usage tracking reports, training evaluations, etc.).

The content distribution network 100 may include one or more communication networks 120. Although only a single network 120 is identified in FIG. 1, the content distribution network 100 may include any number of different communication networks between any of the computer servers and devices shown in FIG. 1 and/or other devices described herein. Communication networks 120 may enable communication between the various computing devices, servers, and other components of the content distribution network 100. As discussed below, various implementations of content distribution networks 100 may employ different types of networks 120, for example, computer networks, telecommunications networks, wireless networks, and/or any combination of these and/or other networks.

The content distribution network 100 may include one or several navigation systems or features including, for example, the Global Positioning System ("GPS"), GALILEO, or the like, or location systems or features including, for example, one or several transceivers that can determine location of the one or several components of the content distribution network 100 via, for example, triangulation. All of these are depicted as navigation system 122.

In some embodiments, navigation system 122 can include several features that can communicate with one or several components of the content distribution network 100 including, for example, with one or several of the user devices 106 and/or with one or several of the supervisor devices 110. In some embodiments, this communication can include the transmission of a signal from the navigation system 122 which signal is received by one or several components of the content distribution network 100 and can be used to determine the location of the one or several components of the content distribution network 100.

Figure 2:
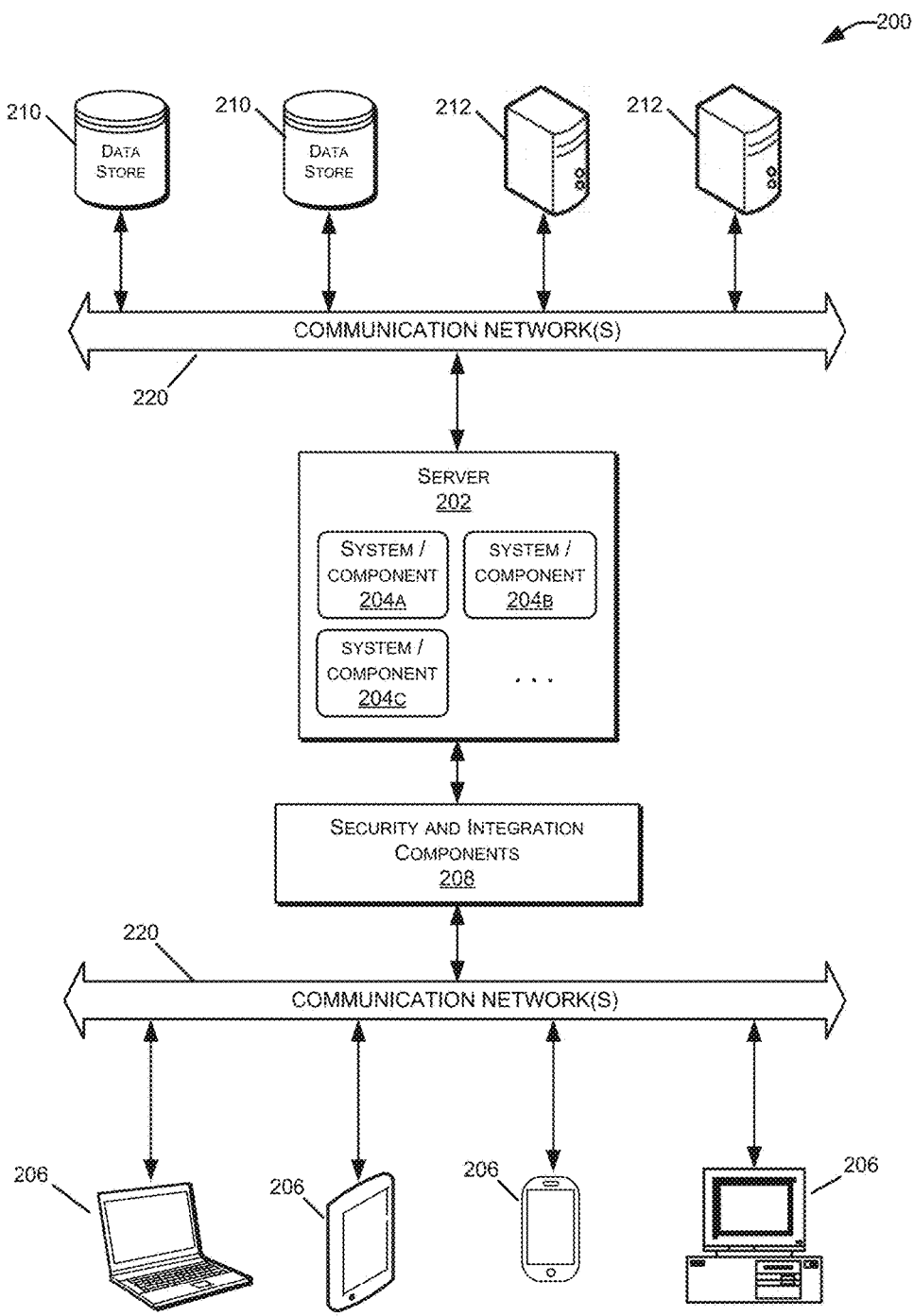
FIG. 2 is a block diagram illustrating a computer server and computing environment within a content distribution network.

With reference to FIG. 2, an illustrative distributed computing environment 200 is shown including a computer server 202, four client computing devices 206, and other components that may implement certain embodiments and features described herein. In some embodiments, the server 202 may correspond to the content management server 102 discussed above in FIG. 1, and the client computing devices 206 may correspond to the user devices 106. However, the computing environment 200 illustrated in FIG. 2 may correspond to any other combination of devices and servers configured to implement a client-server model or other distributed computing architecture.

Client devices 206 may be configured to receive and execute client applications over one or more networks 220. Such client applications may be web browser-based applications and/or standalone software applications, such as mobile device applications. Server 202 may be communicatively coupled with the client devices 206 via one or more communication networks 220. Client devices 206 may receive client applications from server 202 or from other application providers (e.g., public or private application stores). Server 202 may be configured to run one or more server software applications or services, for example, web-based or cloud-based services, to support content distribution and interaction with client devices 206. Users operating client devices 206 may in turn utilize one or more client applications (e.g., virtual client applications) to interact with server 202 to utilize the services provided by these components.

Various different subsystems and/or components 204 may be implemented on server 202. Users operating the client devices 206 may initiate one or more client applications to use services provided by these subsystems and components. The subsystems and components within the server 202 and client devices 206 may be implemented in hardware, firmware, software, or combinations thereof. Various different system configurations are possible in different distributed computing systems 200 and content distribution networks 100. The embodiment shown in FIG. 2 is thus one example of a distributed computing system and is not intended to be limiting.

Although exemplary computing environment 200 is shown with four client computing devices 206, any number of client computing devices may be supported. Other devices, such as specialized sensor devices, etc., may interact with client devices 206 and/or server 202.

As shown in FIG. 2, various security and integration components 208 may be used to send and manage communications between the server 202 and user devices 206 over one or more communication networks 220. The security and integration components 208 may include separate servers, such as web servers and/or authentication servers, and/or specialized networking components, such as firewalls, routers, gateways, load balancers, and the like. In some cases, the security and integration components 208 may correspond to a set of dedicated hardware and/or software operating at the same physical location and under the control of same entities as server 202. For example, components 208 may include one or more dedicated web servers and network hardware in a datacenter or a cloud infrastructure. In other examples, the security and integration components 208 may correspond to separate hardware and software components which may be operated at a separate physical location and/or by a separate entity.

Security and integration components 208 may implement various security features for data transmission and storage, such as authenticating users and restricting access to unknown or unauthorized users. In various implementations, security and integration components 208 may provide, for example, a file-based integration scheme or a service-based integration scheme for transmitting data between the various devices in the content distribution network 100. Security and integration components 208 also may use secure data transmission protocols and/or encryption for data transfers, for example, File Transfer Protocol (FTP), Secure File Transfer Protocol (SFTP), and/or Pretty Good Privacy (PGP) encryption.

In some embodiments, one or more web services may be implemented within the security and integration components 208 and/or elsewhere within the content distribution network 100. Such web services, including cross-domain and/or cross-platform web services, may be developed for enterprise use in accordance with various web service standards, such as RESTful web services (i.e., services based on the Representation State Transfer (REST) architectural style and constraints), and/or web services designed in accordance with the Web Service Interoperability (WS-I) guidelines. Some web services may use the Secure Sockets Layer (SSL) or Transport Layer Security (TLS) protocol to provide secure connections between the server 202 and user devices 206. SSL or TLS may use HTTP or HTTPS to provide authentication and confidentiality. In other examples, web services may be implemented using REST over HTTPS with the OAuth open standard for authentication, or using the WS-Security standard which provides for secure SOAP messages using XML encryption. In other examples, the security and integration components 208 may include specialized hardware for providing secure web services. For example, security and integration components 208 may include secure network appliances having built-in features such as hardware-accelerated SSL and HTTPS, WS-Security, and firewalls. Such specialized hardware may be installed and configured in front of any web servers, so that any external devices may communicate directly with the specialized hardware.

Communication network(s) 220 may be any type of network familiar to those skilled in the art that can support data communications using any of a variety of commercially-available protocols, including without limitation, TCP/IP (transmission control protocol/Internet protocol), SNA (systems network architecture), IPX (Internet packet exchange), Secure Sockets Layer (SSL) or Transport Layer Security (TLS) protocols, Hyper Text Transfer Protocol (HTTP) and Secure Hyper Text Transfer Protocol (HTTPS), Bluetooth®, Near Field Communication (NFC), and the like. Merely by way of example, network(s) 220 may be local area networks (LAN), such as one based on Ethernet, Token-Ring and/or the like. Network(s) 220 also may be wide-area networks, such as the Internet. Networks 220 may include telecommunication networks such as public switched telephone networks (PSTNs), or virtual networks such as an intranet or an extranet. Infrared and wireless networks (e.g., using the Institute of Electrical and Electronics (IEEE) 802.11 protocol suite or other wireless protocols) also may be included in networks 220.

Computing environment 200 also may include one or more data stores 210 and/or back-end servers 212. In certain examples, the data stores 210 may correspond to data store server(s) 104 discussed above in FIG. 1, and back-end servers 212 may correspond to the various back-end servers 112-116. Data stores 210 and servers 212 may reside in the same datacenter or may operate at a remote location from server 202. In some cases, one or more data stores 210 may reside on a non-transitory storage medium within the server 202. Other data stores 210 and back-end servers 212 may be remote from server 202 and configured to communicate with server 202 via one or more networks 220. In certain embodiments, data stores 210 and back-end servers 212 may reside in a storage-area network (SAN), or may use storage-as-a-service (STaaS) architectural model.

Figure 3:
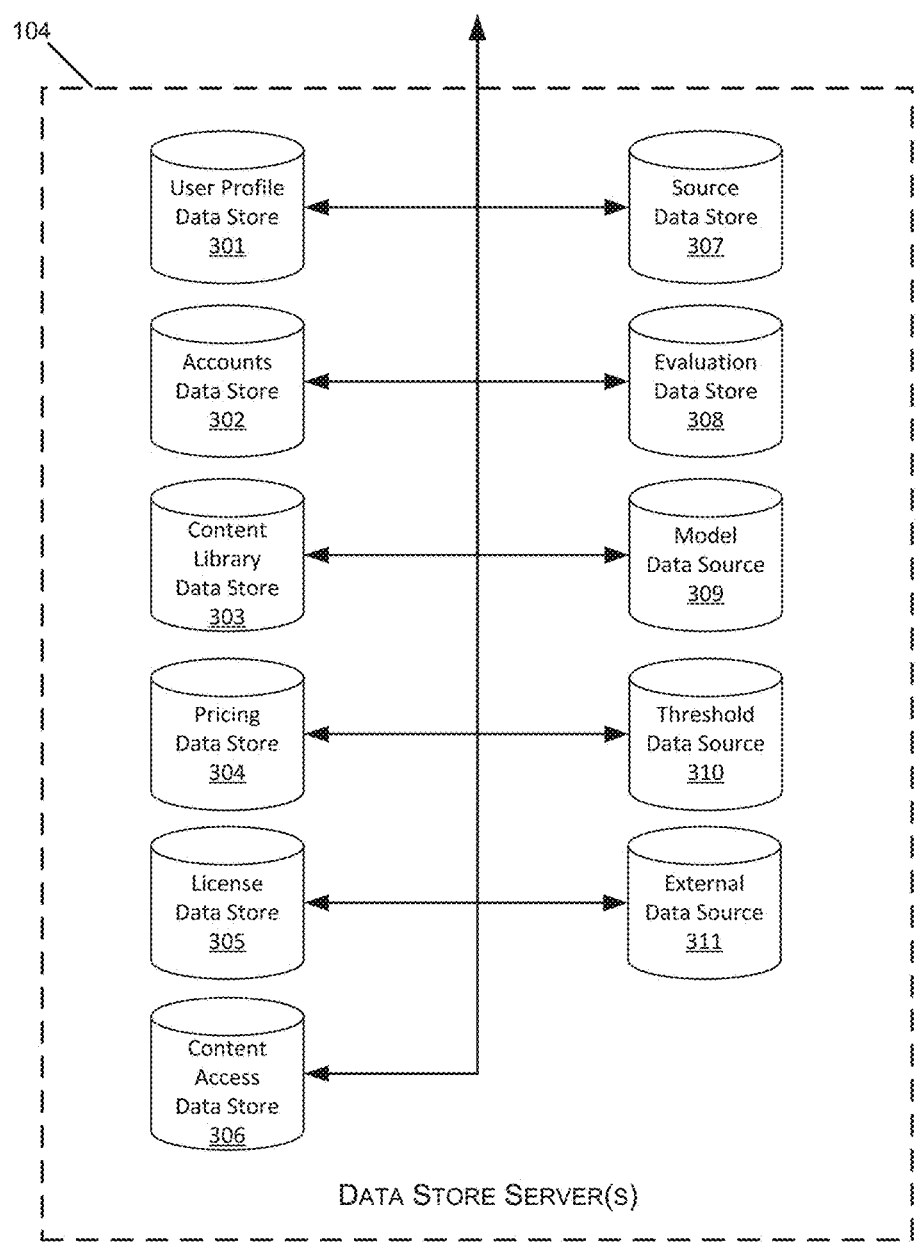
FIG. 3 is a block diagram illustrating an embodiment of one or more data store servers within a content distribution network.

With reference to FIG. 3, an illustrative set of data stores and/or data store servers is shown, corresponding to the data store servers 104 of the content distribution network 100 discussed above in FIG. 1. One or more individual data stores 301-311 may reside in storage on a single computer server 104 (or a single server farm or cluster) under the control of a single entity, or may reside on separate servers operated by different entities and/or at remote locations. In some embodiments, data stores 301-311 may be accessed by the content management server 102 and/or other devices and servers within the network 100 (e.g., user devices 106, supervisor devices 110, administrator servers 116, etc.). Access to one or more of the data stores 301-311 may be limited or denied based on the processes, user credentials, and/or devices attempting to interact with the data store.

The paragraphs below describe examples of specific data stores that may be implemented within some embodiments of a content distribution network 100. It should be understood that the below descriptions of data stores 301-311, including their functionality and types of data stored therein, are illustrative and non-limiting. Data stores server architecture, design, and the execution of specific data stores 301-311 may depend on the context, size, and functional requirements of a content distribution network 100. For example, in content distribution systems 100 used for professional training and educational purposes, separate databases or file-based storage systems may be implemented in data store server(s) 104 to store trainee and/or student data, trainer and/or professor data, training module data and content descriptions, training results, evaluation data, and the like. In contrast, in content distribution systems 100 used for media distribution from content providers to subscribers, separate data stores may be implemented in data stores server(s) 104 to store listings of available content titles and descriptions, content title usage statistics, subscriber profiles, account data, payment data, network usage statistics, etc.

A user profile data store 301, also referred to herein as a user profile database 301, may include information relating to the end users within the content distribution network 100. This information may include user characteristics such as the user names, access credentials (e.g., logins and passwords), user preferences, and information relating to any previous user interactions within the content distribution network 100 (e.g., requested content, posted content, content modules completed, training scores or evaluations, other associated users, etc.). In some embodiments, this information can relate to one or several individual end users such as, for example, one or several students, teachers, administrators, or the like, and in some embodiments, this information can relate to one or several institutional end users such as, for example, one or several schools, groups of schools such as one or several school districts, one or several colleges, one or several universities, one or several training providers, or the like. In some embodiments, this information can identify one or several user memberships in one or several groups such as, for example, a student's membership in a university, school, program, grade, course, class, or the like.

The user profile database 301 can include information relating to a user's status, location, or the like. This information can identify, for example, a device a user is using, the location of that device, or the like. In some embodiments, this information can be generated based on any location detection technology including, for example, a navigation system 122, or the like.

Information relating to the user's status can identify, for example, logged-in status information that can indicate whether the user is presently logged-in to the content distribution network 100 and/or whether the log-in-is active. In some embodiments, the information relating to the user's status can identify whether the user is currently accessing content and/or participating in an activity from the content distribution network 100.

In some embodiments, information relating to the user's status can identify, for example, one or several attributes of the user's interaction with the content distribution network 100, and/or content distributed by the content distribution network 100. This can include data identifying the user's interactions with the content distribution network 100, the content consumed by the user through the content distribution network 100, or the like. In some embodiments, this can include data identifying the type of information accessed through the content distribution network 100 and/or the type of activity performed by the user via the content distribution network 100, the lapsed time since the last time the user accessed content and/or participated in an activity from the content distribution network 100, or the like. In some embodiments, this information can relate to a content program comprising an aggregate of data, content, and/or activities, and can identify, for example, progress through the content program, or through the aggregate of data, content, and/or activities forming the content program. In some embodiments, this information can track, for example, the amount of time since participation in and/or completion of one or several types of activities, the amount of time since communication with one or several supervisors and/or supervisor devices 110, or the like.

In some embodiments in which the one or several end users are individuals, and specifically are students, the user profile database 301 can further include information relating to these students' academic and/or educational history. This information can identify one or several courses of study that the student has initiated, completed, and/or partially completed, as well as grades received in those courses of study. In some embodiments, the student's academic and/or educational history can further include information identifying student performance on one or several tests, quizzes, and/or assignments. In some embodiments, this information can be stored in a tier of memory that is not the fastest memory in the content delivery network 100.

The user profile database 301 can include information relating to one or several student learning preferences. In some embodiments, for example, the user, also referred to herein as the student or the student-user may have one or several preferred learning styles, one or several most effective learning styles, and/or the like. In some embodiments, the student's learning style can be any learning style describing how the student best learns or how the student prefers to learn. In one embodiment, these learning styles can include, for example, identification of the student as an auditory learner, as a visual learner, and/or as a tactile learner. In some embodiments, the data identifying one or several student learning styles can include data identifying a learning style based on the student's educational history such as, for example, identifying a student as an auditory learner when the student has received significantly higher grades and/or scores on assignments and/or in courses favorable to auditory learners. In some embodiments, this information can be stored in a tier of memory that is not the fastest memory in the content delivery network 100.

In some embodiments, the user profile data store 301 can further include information identifying one or several user skill levels. In some embodiments, these one or several user skill levels can identify a skill level determined based on past performance by the user interacting with the content delivery network 100, and in some embodiments, these one or several user skill levels can identify a predicted skill level determined based on past performance by the user interacting with the content delivery network 100 and one or several predictive models.

The user profile database 301 can further include information relating to one or several teachers and/or instructors who are responsible for organizing, presenting, and/or managing the presentation of information to the student. In some embodiments, user profile database 301 can include information identifying courses and/or subjects that have been taught by the teacher, data identifying courses and/or subjects currently taught by the teacher, and/or data identifying courses and/or subjects that will be taught by the teacher. In some embodiments, this can include information relating to one or several teaching styles of one or several teachers. In some embodiments, the user profile database 301 can further include information indicating past evaluations and/or evaluation reports received by the teacher. In some embodiments, the user profile database 301 can further include information relating to improvement suggestions received by the teacher, training received by the teacher, continuing education received by the teacher, and/or the like. In some embodiments, this information can be stored in a tier of memory that is not the fastest memory in the content delivery network 100.

An accounts data store 302, also referred to herein as an accounts database 302, may generate and store account data for different users in various roles within the content distribution network 100. For example, accounts may be created in an accounts data store 302 for individual end users, supervisors, administrator users, and entities such as companies or educational institutions. Account data may include account types, current account status, account characteristics, and any parameters, limits, restrictions associated with the accounts.

A content library data store 303, also referred to herein as a content library database 303, may include information describing the individual content items (or content resources or data packets) available via the content distribution network 100. In some embodiments, these data packets in the content library database 303 can be linked to form an object network. In some embodiments, these data packets can be linked in the object network according to one or several prerequisite relationships that can, for example, identify the relative hierarchy and/or difficulty of the data objects. In some embodiments, this hierarchy of data objects can be generated by the content distribution network 100 according to user experience with the object network, and in some embodiments, this hierarchy of data objects can be generated based on one or several existing and/or external hierarchies such as, for example, a syllabus, a table of contents, or the like. In some embodiments, for example, the object network can correspond to a syllabus such that content for the syllabus is embodied in the object network.

In some embodiments, the content library data store 303 can comprise a syllabus, a schedule, or the like. In some embodiments, the syllabus or schedule can identify one or several tasks and/or events relevant to the user. In some embodiments, for example, when the user is a member of a group such as a section or a class, these tasks and/or events relevant to the user can identify one or several assignments, quizzes, exams, or the like.

In some embodiments, the library data store 303 may include metadata, properties, and other characteristics associated with the content resources stored in the content server 112. Such data may identify one or more aspects or content attributes of the associated content resources, for example, subject matter, access level, or skill level of the content resources, license attributes of the content resources (e.g., any limitations and/or restrictions on the licensable use and/or distribution of the content resource), price attributes of the content resources (e.g., a price and/or price structure for determining a payment amount for use or distribution of the content resource), rating attributes for the content resources (e.g., data indicating the evaluation or effectiveness of the content resource), and the like. In some embodiments, the library data store 303 may be configured to allow updating of content metadata or properties, and to allow the addition and/or removal of information relating to the content resources. For example, content relationships may be implemented as graph structures, which may be stored in the library data store 303 or in an additional store for use by selection algorithms along with the other metadata.

In some embodiments, the content library data store 303 can contain information used in evaluating responses received from users. In some embodiments, for example, a user can receive content from the content distribution network 100 and can, subsequent to receiving that content, provide a response to the received content. In some embodiments, for example, the received content can comprise one or several questions, prompts, or the like, and the response to the received content can comprise an answer to those one or several questions, prompts, or the like. In some embodiments, information, referred to herein as "comparative data," from the content library data store 303 can be used to determine whether the responses are the correct and/or desired responses.

In some embodiments, the content library database 303 and/or the user profile database 301 can comprise an aggregation network, also referred to herein as a content network or content aggregation network. The aggregation network can comprise a plurality of content aggregations that can be linked together by, for example: creation by common user; relation to a common subject, topic, skill, or the like; creation from a common set of source material such as source data packets; or the like. In some embodiments, the content aggregation can comprise a grouping of content comprising the presentation portion that can be provided to the user in the form of, for example, a flash card and an extraction portion that can comprise the desired response to the presentation portion such as for example, an answer to a flash card. In some embodiments, one or several content aggregations can be generated by the content distribution network 100 and can be related to one or several data packets that they can be, for example, organized in object network. In some embodiments, the one or several content aggregations can be each created from content stored in one or several of the data packets.

In some embodiments, the content aggregations located in the content library database 303 and/or the user profile database 301 can be associated with a user-creator of those content aggregations. In some embodiments, access to content aggregations can vary based on, for example, whether a user created the content aggregations. In some embodiments, the content library database 303 and/or the user profile database 301 can comprise a database of content aggregations associated with a specific user, and in some embodiments, the content library database 303 and/or the user profile database 301 can comprise a plurality of databases of content aggregations that are each associated with a specific user. In some embodiments, these databases of content aggregations can include content aggregations created by their specific user and, in some embodiments, these databases of content aggregations can further include content aggregations selected for inclusion by their specific user and/or a supervisor of that specific user. In some embodiments, these content aggregations can be arranged and/or linked in a hierarchical relationship similar to the data packets in the object network and/or linked to the object network in the object network or the tasks or skills associated with the data packets in the object network or the syllabus or schedule.

In some embodiments, the content aggregation network, and the content aggregations forming the content aggregation network can be organized according to the object network and/or the hierarchical relationships embodied in the object network. In some embodiments, the content aggregation network, and/or the content aggregations forming the content aggregation network can be organized according to one or several tasks identified in the syllabus, schedule or the like.

A pricing data store 304 may include pricing information and/or pricing structures for determining payment amounts for providing access to the content distribution network 100 and/or the individual content resources within the network 100. In some cases, pricing may be determined based on a user's access to the content distribution network 100, for example, a time-based subscription fee, or pricing based on network usage. In other cases, pricing may be tied to specific content resources. Certain content resources may have associated pricing information, whereas other pricing determinations may be based on the resources accessed, the profiles and/or accounts of the user, and the desired level of access (e.g., duration of access, network speed, etc.). Additionally, the pricing data store 304 may include information relating to compilation pricing for groups of content resources, such as group prices and/or price structures for groupings of resources.

A license data store 305 may include information relating to licenses and/or licensing of the content resources within the content distribution network 100. For example, the license data store 305 may identify licenses and licensing terms for individual content resources and/or compilations of content resources in the content server 112, the rights holders for the content resources, and/or common or large-scale right holder information such as contact information for rights holders of content not included in the content server 112.

A content access data store 306 may include access rights and security information for the content distribution network 100 and specific content resources. For example, the content access data store 306 may include login information (e.g., user identifiers, logins, passwords, etc.) that can be verified during user login attempts to the network 100. The content access data store 306 also may be used to store assigned user roles and/or user levels of access. For example, a user's access level may correspond to the sets of content resources and/or the client or server applications that the user is permitted to access. Certain users may be permitted or denied access to certain applications and resources based on their subscription level, training program, course/grade level, etc. Certain users may have supervisory access over one or more end users, allowing the supervisor to access all or portions of the end user's content, activities, evaluations, etc. Additionally, certain users may have administrative access over some users and/or some applications in the content management network 100, allowing such users to add and remove user accounts, modify user access permissions, perform maintenance updates on software and servers, etc.

A source data store 307 may include information relating to the source of the content resources available via the content distribution network. For example, a source data store 307 may identify the authors and originating devices of content resources, previous pieces of data and/or groups of data originating from the same authors or originating devices, and the like.

An evaluation data store 308 may include information used to direct the evaluation of users and content resources in the content management network 100. In some embodiments, the evaluation data store 308 may contain, for example, the analysis criteria and the analysis guidelines for evaluating users (e.g., trainees/students, gaming users, media content consumers, etc.) and/or for evaluating the content resources in the network 100. The evaluation data store 308 also may include information relating to evaluation processing tasks, for example, the identification of users and user devices 106 that have received certain content resources or accessed certain applications, the status of evaluations or evaluation histories for content resources, users, or applications, and the like. Evaluation criteria may be stored in the evaluation data store 308 including data and/or instructions in the form of one or several electronic rubrics or scoring guides for use in the evaluation of the content, users, or applications. The evaluation data store 308 also may include past evaluations and/or evaluation analyses for users, content, and applications, including relative rankings, characterizations, explanations, and the like.

A model data store 309, also referred to herein as a model database 309, can store information relating to one or several predictive models. In some embodiments, these can include one or several evidence models, risk models, skill models, or the like. In some embodiments, an evidence model can be a mathematically-based statistical model. The evidence model can be based on, for example, Item Response Theory (IRT), Bayesian Network (Bayes net), Performance Factor Analysis (PFA), or the like. The evidence model can, in some embodiments, be customizable to a user and/or to one or several content items. Specifically, one or several inputs relating to the user and/or to one or several content items can be inserted into the evidence model. These inputs can include, for example, one or several measures of user skill level, one or several measures of content item difficulty and/or skill level, or the like. The customized evidence model can then be used to predict the likelihood of the user providing desired or undesired responses to one or several of the content items.

In some embodiments, the risk models can include one or several models that can be used to calculate one or several model function values. In some embodiments, these one or several model function values can be used to calculate a risk probability, which risk probability can characterize the risk of a user such as a student-user failing to achieve a desired outcome such as, for example, failing to correctly respond to one or several data packets, failure to achieve a desired level of completion of a program, for example in a pre-defined time period, failure to achieve a desired learning outcome, or the like. In some embodiments, the risk probability can identify the risk of the student-user failing to complete 60% of the program.

In some embodiments, these models can include a plurality of model functions including, for example, a first model function, a second model function, a third model function, and a fourth model function. In some embodiments, some or all of the model functions can be associated with a portion of the program such as, for example, a completion stage and/or completion status of the program. In one embodiment, for example, the first model function can be associated with a first completion status, the second model function can be associated with a second completion status, the third model function can be associated with a third completion status, and the fourth model function can be associated with a fourth completion status. In some embodiments, these completion statuses can be selected such that some or all of these completion statuses are less than the desired level of completion of the program. Specifically, in some embodiments, these completion statuses can be selected to all be at less than 60% completion of the program, and more specifically, in some embodiments, the first completion status can be at 20% completion of the program, the second completion status can be at 30% completion of the program, the third completion status can be at 40% completion of the program, and the fourth completion status can be at 50% completion of the program. Similarly, any desired number of model functions can be associated with any desired number of completion statuses.

In some embodiments, a model function can be selected from the plurality of model functions based on a student-user's progress through a program. In some embodiments, the student-user's progress can be compared to one or several status trigger thresholds, each of which status trigger thresholds can be associated with one or more of the model functions. If one of the status triggers is triggered by the student-user's progress, the corresponding one or several model functions can be selected.

The model functions can comprise a variety of types of models and/or functions. In some embodiments, each of the model functions outputs a function value that can be used in calculating a risk probability. This function value can be calculated by performing one or several mathematical operations on one or several values indicative of one or several user attributes and/or user parameters, also referred to herein as program status parameters. In some embodiments, each of the model functions can use the same program status parameters, and in some embodiments, the model functions can use different program status parameters. In some embodiments, the model functions use different program status parameters when at least one of the model functions uses at least one program status parameter that is not used by others of the model functions.

In some embodiments, a skill model can comprise a statistical model identifying a predictive skill level of one or several students. In some embodiments, this model can identify a single skill level of a student and/or a range of possible skill levels of a student. In some embodiments, this statistical model can identify a skill level of a student-user and an error value or error range associated with that skill level. In some embodiments, the error value can be associated with a confidence interval determined based on a confidence level. Thus, in some embodiments, as the number of student interactions with the content distribution network increases, the confidence level can increase and the error value can decrease such that the range identified by the error value about the predicted skill level is smaller.

A threshold database 310, also referred to herein as a threshold database, can store one or several threshold values. These one or several threshold values can delineate between states or conditions. In one exemplary embodiment, for example, a threshold value can delineate between an acceptable user performance and an unacceptable user performance, between content appropriate for a user and content that is inappropriate for a user, between risk levels, or the like.

In addition to the illustrative data stores described above, data store server(s) 104 (e.g., database servers, file-based storage servers, etc.) may include one or more external data aggregators 311. External data aggregators 311 may include third-party data sources accessible to the content management network 100, but not maintained by the content management network 100. External data aggregators 311 may include any electronic information source relating to the users, content resources, or applications of the content distribution network 100. For example, external data aggregators 311 may be third-party data stores containing demographic data, education-related data, consumer sales data, health-related data, and the like. Illustrative external data aggregators 311 may include, for example, social networking web servers, public records data stores, learning management systems, educational institution servers, business servers, consumer sales data stores, medical record data stores, etc. Data retrieved from various external data aggregators 311 may be used to verify and update user account information, suggest user content, and perform user and content evaluations.

Figure 4:
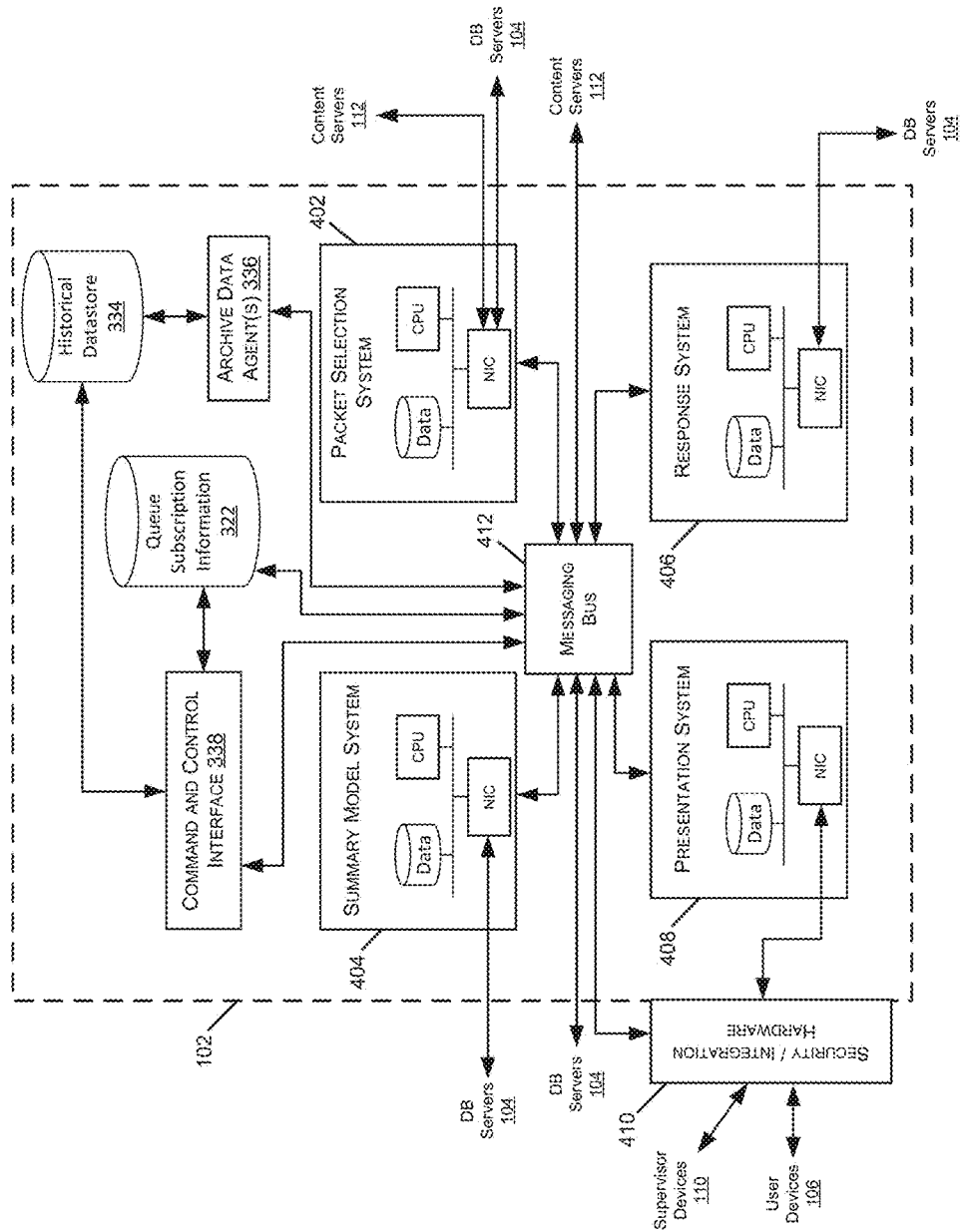
FIG. 4 is a block diagram illustrating an embodiment of one or more content management servers within a content distribution network.

With reference now to FIG. 4, a block diagram is shown illustrating an embodiment of one or more content management servers 102 within a content distribution network 100. In such an embodiment, content management server 102 performs internal data gathering and processing of streamed content along with external data gathering and processing. Other embodiments could have either all external or all internal data gathering. This embodiment allows reporting timely information that might be of interest to the reporting party or other parties. In this embodiment, the content management server 102 can monitor gathered information from several sources to allow it to make timely business and/or processing decisions based upon that information. For example, reports of user actions and/or responses, as well as the status and/or results of one or several processing tasks could be gathered and reported to the content management server 102 from a number of sources.

Internally, the content management server 102 gathers information from one or more internal components 402-408. The internal components 402-408 gather and/or process information relating to such things as: content provided to users; content consumed by users; responses provided by users; user skill levels; content difficulty levels; next content for providing to users; etc. The internal components 402-408 can report the gathered and/or generated information in real-time, near real-time or along another time line. To account for any delay in reporting information, a time stamp or staleness indicator can inform others of how timely the information was sampled. The content management server 102 can opt to allow third parties to use internally or externally gathered information that is aggregated within the server 102 by subscription to the content distribution network 100.

A command and control (CC) interface 338 configures the gathered input information to an output of data streams, also referred to herein as content streams. APIs for accepting gathered information and providing data streams are provided to third parties external to the server 102 who want to subscribe to data streams. The server 102 or a third party can design as yet undefined APIs using the CC interface 338.

The server 102 can also define authorization and authentication parameters using the CC interface 338 such as authentication, authorization, login, and/or data encryption. CC information is passed to the internal components 402-408 and/or other components of the content distribution network 100 through a channel separate from the gathered information or data stream in this embodiment, but other embodiments could embed CC information in these communication channels. The CC information allows throttling information reporting frequency, specifying formats for information and data streams, deactivation of one or several internal components 402-408 and/or other components of the content distribution network 100, updating authentication and authorization, etc.

The various data streams that are available can be researched and explored through the CC interface 338. Those data stream selections for a particular subscriber, which can be one or several of the internal components 402-408 and/or other components of the content distribution network 100, are stored in the queue subscription information database 322. The server 102 and/or the CC interface 338 then routes selected data streams to processing subscribers that have selected delivery of a given data stream. Additionally, the server 102 also supports historical queries of the various data streams that are stored in an historical data store 334 as gathered by an archive data agent 336. Through the CC interface 238 various data streams can be selected for archiving into the historical data store 334.

Components of the content distribution network 100 outside of the server 102 can also gather information that is reported to the server 102 in real-time, near real-time or along another time line. There is a defined API between those components and the server 102. Each type of information or variable collected by server 102 falls within a defined API or multiple APIs. In some cases, the CC interface 338 is used to define additional variables to modify an API that might be of use to processing subscribers. The additional variables can be passed to all processing subscribes or just a subset. For example, a component of the content distribution network 100 outside of the server 102 may report a user response but define an identifier of that user as a private variable that would not be passed to processing subscribers lacking access to that user and/or authorization to receive that user data. Processing subscribers having access to that user and/or authorization to receive that user data would receive the subscriber identifier along with response reported that component. Encryption and/or unique addressing of data streams or sub-streams can be used to hide the private variables within the messaging queues.

The user devices 106 and/or supervisor devices 110 communicate with the server 102 through security and/or integration hardware 410. The communication with security and/or integration hardware 410 can be encrypted or not. For example, a socket using a TCP connection could be used. In addition to TCP, other transport layer protocols like SCTP and UDP could be used in some embodiments to intake the gathered information. A protocol such as SSL could be used to protect the information over the TCP connection. Authentication and authorization can be performed to any user devices 106 and/or supervisor device interfacing to the server 102. The security and/or integration hardware 410 receives the information from one or several of the user devices 106 and/or the supervisor devices 110 by providing the API and any encryption, authorization, and/or authentication. In some cases, the security and/or integration hardware 410 reformats or rearranges this received information.

The messaging bus 412, also referred to herein as a messaging queue or a messaging channel, can receive information from the internal components of the server 102 and/or components of the content distribution network 100 outside of the server 102 and distribute the gathered information as a data stream to any processing subscribers that have requested the data stream from the messaging queue 412. Specifically, in some embodiments, the messaging bus 412 can receive and output information from at least one of the packet selection system, the presentation system, the response system, and the summary model system. In some embodiments, this information can be output according to a "push" model, and in some embodiments, this information can be output according to a "pull" model.

As indicated in FIG. 4, processing subscribers are indicated by a connector to the messaging bus 412, the connector having an arrow head pointing away from the messaging bus 412. Only data streams within the messaging queue 412 that a particular processing subscriber has subscribed to may be read by that processing subscriber if received at all. Gathered information sent to the messaging queue 412 is processed and returned in a data stream in a fraction of a second by the messaging queue 412. Various multicasting and routing techniques can be used to distribute a data stream from the messaging queue 412 that a number of processing subscribers have requested. Protocols such as Multicast or multiple Unicast could be used to distribute streams within the messaging queue 412. Additionally, transport layer protocols like TCP, SCTP and UDP could be used in various embodiments.

Through the CC interface 338, an external or internal processing subscriber can be assigned one or more data streams within the messaging queue 412. A data stream is a particular type of message in a particular category. For example, a data stream can comprise all of the data reported to the messaging bus 412 by a designated set of components. One or more processing subscribers could subscribe and receive the data stream to process the information and make a decision and/or feed the output from the processing as gathered information fed back into the messaging queue 412. Through the CC interface 338 a developer can search the available data streams or specify a new data stream and its API. The new data stream might be determined by processing a number of existing data streams with a processing subscriber.

The CDN 110 has internal processing subscribers 402-408 that process assigned data streams to perform functions within the server 102. Internal processing subscribers 402-408 could perform functions such as providing content to a user, receiving a response from a user, determining the correctness of the received response, updating one or several models based on the correctness of the response, recommending new content for providing to one or several users, or the like. The internal processing subscribers 402-408 can decide filtering and weighting of records from the data stream. To the extent that decisions are made based upon analysis of the data stream, each data record is time stamped to reflect when the information was gathered such that additional credibility could be given to more recent results, for example. Other embodiments may filter out records in the data stream that are from an unreliable source or stale. For example, a particular contributor of information may prove to have less than optimal gathered information and that could be weighted very low or removed altogether.

Internal processing subscribers 402-408 may additionally process one or more data streams to provide different information to feed back into the messaging queue 412 to be part of a different data stream. For example, hundreds of user devices 106 could provide responses that are put into a data stream on the messaging queue 412. An internal processing subscriber 402-408 could receive the data stream and process it to determine the difficulty of one or several data packets provided to one or several users, and supply this information back onto the messaging queue 412 for possible use by other internal and external processing subscribers.

As mentioned above, the CC interface 338 allows the CDN 110 to query historical messaging queue 412 information. An archive data agent 336 listens to the messaging queue 412 to store data streams in a historical database 334. The historical database 334 may store data streams for varying amounts of time and may not store all data streams. Different data streams may be stored for different amounts of time.

With regard to the components 402-48, the content management server(s) 102 may include various server hardware and software components that manage the content resources within the content distribution network 100 and provide interactive and adaptive content to users on various user devices 106. For example, content management server(s) 102 may provide instructions to and receive information from the other devices within the content distribution network 100, in order to manage and transmit content resources, user data, and server or client applications executing within the network 100.

A content management server 102 may include a packet selection system 402. The packet selection system 402 may be implemented using dedicated hardware within the content distribution network 100 (e.g., a packet selection server 402), or using designated hardware and software resources within a shared content management server 102. In some embodiments, the packet selection system 402 may adjust the selection and adaptive capabilities of content resources to match the needs and desires of the users receiving the content. For example, the packet selection system 402 may query various data stores and servers 104 to retrieve user information, such as user preferences and characteristics (e.g., from a user profile data store 301), user access restrictions to content recourses (e.g., from a content access data store 306), previous user results and content evaluations (e.g., from an evaluation data store 308), and the like. Based on the retrieved information from data stores 104 and other data sources, the packet selection system 402 may modify content resources for individual users.

In some embodiments, the packet selection system 402 can include a recommendation engine, also referred to herein as an adaptive recommendation engine. In some embodiments, the recommendation engine can select one or several pieces of content, also referred to herein as data packets, for providing to a user. These data packets can be selected based on, for example, the information retrieved from the database server 104 including, for example, the user profile database 301, the content library database 303, the model database 309, or the like. In some embodiments, these one or several data packets can be adaptively selected and/or selected according to one or several selection rules. In one embodiment, for example, the recommendation engine can retrieve information from the user profile database 301 identifying, for example, a skill level of the user. The recommendation engine can further retrieve information from the content library database 303 identifying, for example, potential data packets for providing to the user and the difficulty of those data packets and/or the skill level associated with those data packets.

The recommendation engine can identify one or several potential data packets for providing and/or one or several data packets for providing to the user based on, for example, one or several rules, models, predictions, or the like. The recommendation engine can use the skill level of the user to generate a prediction of the likelihood of one or several users providing a desired response to some or all of the potential data packets. In some embodiments, the recommendation engine can pair one or several data packets with selection criteria that may be used to determine which packet should be delivered to a student-user based on one or several received responses from that student-user. In some embodiments, one or several data packets can be eliminated from the pool of potential data packets if the prediction indicates either too high a likelihood of a desired response or too low a likelihood of a desired response. In some embodiments, the recommendation engine can then apply one or several selection criteria to the remaining potential data packets to select a data packet for providing to the user. These one or several selection criteria can be based on, for example, criteria relating to a desired estimated time for receipt of response to the data packet, one or several content parameters, one or several assignment parameters, or the like.

A content management server 102 also may include a summary model system 404. The summary model system 404 may be implemented using dedicated hardware within the content distribution network 100 (e.g., a summary model server 404), or using designated hardware and software resources within a shared content management server 102. In some embodiments, the summary model system 404 may monitor the progress of users through various types of content resources and groups, such as media compilations, courses or curriculums in training or educational contexts, interactive gaming environments, and the like. For example, the summary model system 404 may query one or more databases and/or data store servers 104 to retrieve user data such as associated content compilations or programs, content completion status, user goals, results, and the like.

A content management server 102 also may include a response system 406, which can include, in some embodiments, a response processor. The response system 406 may be implemented using dedicated hardware within the content distribution network 100 (e.g., a response server 406), or using designated hardware and software resources within a shared content management server 102. The response system 406 may be configured to receive and analyze information from user devices 106. For example, various ratings of content resources submitted by users may be compiled and analyzed, and then stored in a data store (e.g., a content library data store 303 and/or evaluation data store 308) associated with the content. In some embodiments, the response server 406 may analyze the information to determine the effectiveness or appropriateness of content resources with, for example, a subject matter, an age group, a skill level, or the like. In some embodiments, the response system 406 may provide updates to the packet selection system 402 or the summary model system 404, with the attributes of one or more content resources or groups of resources within the network 100. The response system 406 also may receive and analyze user evaluation data from user devices 106, supervisor devices 110, and administrator servers 116, etc. For instance, response system 406 may receive, aggregate, and analyze user evaluation data for different types of users (e.g., end users, supervisors, administrators, etc.) in different contexts (e.g., media consumer ratings, trainee or student comprehension levels, teacher effectiveness levels, gamer skill levels, etc.).

In some embodiments, the response system 406 can be further configured to receive one or several responses from the user and analyze these one or several responses. In some embodiments, for example, the response system 406 can be configured to translate the one or several responses into one or several observables. As used herein, an observable is a characterization of a received response. In some embodiments, the translation of the one or several responses into one or several observables can include determining whether the one or several responses are correct responses, also referred to herein as desired responses, or are incorrect responses, also referred to herein as undesired responses. In some embodiments, the translation of the one or several responses into one or several observables can include characterizing the degree to which one or several responses are desired responses and/or undesired responses. In some embodiments, one or several values can be generated by the response system 406 to reflect user performance in responding to the one or several data packets. In some embodiments, these one or several values can comprise one or several scores for one or several responses and/or data packets.

A content management server 102 also may include a presentation system 408. The presentation system 408 may be implemented using dedicated hardware within the content distribution network 100 (e.g., a presentation server 408), or using designated hardware and software resources within a shared content management server 102. The presentation system 408 can include a presentation engine that can be, for example, a software module running on the content delivery system.

The presentation system 408, also referred to herein as the presentation module or the presentation engine, may receive content resources from the packet selection system 402 and/or from the summary model system 404, and provide the resources to user devices 106. The presentation system 408 may determine the appropriate presentation format for the content resources based on the user characteristics and preferences, and/or the device capabilities of user devices 106. If needed, the presentation system 408 may convert the content resources to the appropriate presentation format and/or compress the content before transmission. In some embodiments, the presentation system 408 may also determine the appropriate transmission media and communication protocols for transmission of the content resources.

In some embodiments, the presentation system 408 may include specialized security and integration hardware 410, along with corresponding software components to implement the appropriate security features content transmission and storage, to provide the supported network and client access models, and to support the performance and scalability requirements of the network 100. The security and integration layer 410 may include some or all of the security and integration components 208 discussed above in FIG. 2, and may control the transmission of content resources and other data, as well as the receipt of requests and content interactions, to and from the user devices 106, supervisor devices 110, administrative servers 116, and other devices in the network 100.

Figure 5:
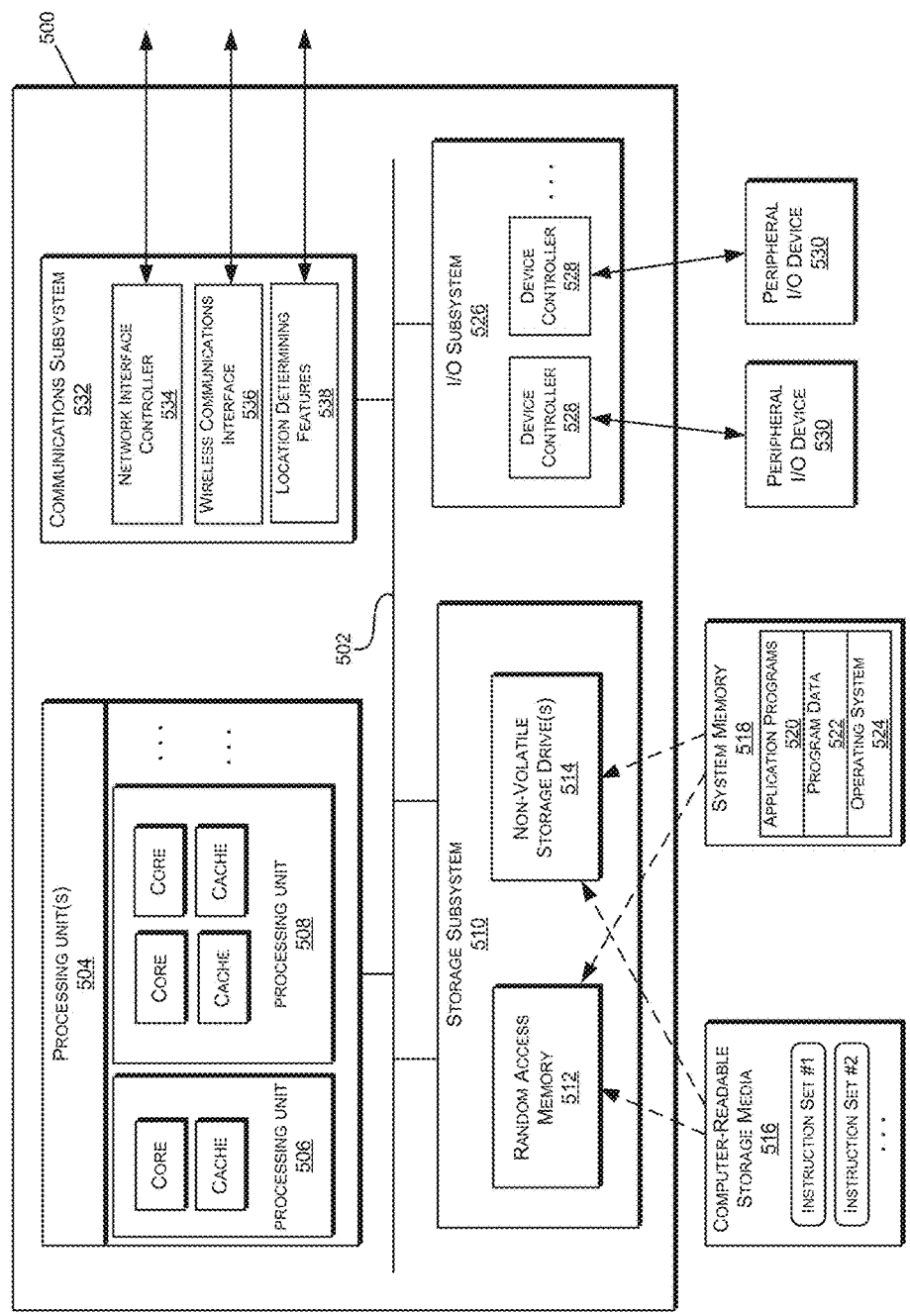
FIG. 5 is a block diagram illustrating the physical and logical components of a special-purpose computer device within a content distribution network.

With reference now to FIG. 5, a block diagram of an illustrative computer system is shown. The system 500 may correspond to any of the computing devices or servers of the content distribution network 100 described above, or any other computing devices described herein, and specifically can include, for example, one or several of the user devices 106, the supervisor device 110, and/or any of the servers 102, 104, 108, 112, 114, 116. In this example, computer system 500 includes processing units 504 that communicate with a number of peripheral subsystems via a bus subsystem 502. These peripheral subsystems include, for example, a storage subsystem 510, an I/O subsystem 526, and a communications subsystem 532.

Bus subsystem 502 provides a mechanism for letting the various components and subsystems of computer system 500 communicate with each other as intended. Although bus subsystem 502 is shown schematically as a single bus, alternative embodiments of the bus subsystem may utilize multiple buses. Bus subsystem 502 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 504, which may be implemented as one or more integrated circuits (e.g., a conventional microprocessor or microcontroller), controls the operation of computer system 500. One or more processors, including single core and/or multicore processors, may be included in processing unit 504. As shown in the figure, processing unit 504 may be implemented as one or more independent processing units 506 and/or 508 with single or multicore processors and processor caches included in each processing unit. In other embodiments, processing unit 504 may also be implemented as a quad-core processing unit or larger multicore designs (e.g., hexa-core processors, octo-core processors, ten-core processors, or greater).

Processing unit 504 may execute a variety of software processes embodied in program code, and may maintain multiple concurrently executing programs or processes. At any given time, some or all of the program code to be executed can be resident in processor(s) 504 and/or in storage subsystem 510. In some embodiments, computer system 500 may include one or more specialized processors, such as digital signal processors (DSPs), outboard processors, graphics processors, application-specific processors, and/or the like.

I/O subsystem 526 may include device controllers 528 for one or more user interface input devices and/or user interface output devices 530. User interface input and output devices 530 may be integral with the computer system 500 (e.g., integrated audio/video systems, and/or touchscreen displays), or may be separate peripheral devices which are attachable/detachable from the computer system 500. The I/O subsystem 526 may provide one or several outputs to a user by converting one or several electrical signals to the user in perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 530 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 530 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additional input devices 530 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 530 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from computer system 500 to a user or other computer. For example, output devices 530 may include, without limitation, a variety of display devices that visually convey text, graphics and audio/video information such as monitors, printers, speakers, headphones, automotive navigation systems, plotters, voice output devices, and modems.

Computer system 500 may comprise one or more storage subsystems 510, comprising hardware and software components used for storing data and program instructions, such as system memory 518 and computer-readable storage media 516. The system memory 518 and/or computer-readable storage media 516 may store program instructions that are loadable and executable on processing units 504, as well as data generated during the execution of these programs.

Depending on the configuration and type of computer system 500, system memory 318 may be stored in volatile memory (such as random access memory (RAM) 512) and/or in non-volatile storage drives 514 (such as read-only memory (ROM), flash memory, etc.). The RAM 512 may contain data and/or program modules that are immediately accessible to and/or presently being operated and executed by processing units 504. In some implementations, system memory 518 may include multiple different types of memory, such as static random access memory (SRAM) or dynamic random access memory (DRAM). In some implementations, a basic input/output system (BIOS), containing the basic routines that help to transfer information between elements within computer system 500, such as during start-up, may typically be stored in the non-volatile storage drives 514. By way of example, and not limitation, system memory 518 may include application programs 520, such as client applications, Web browsers, mid-tier applications, server applications, etc., program data 522, and an operating system 524.

Storage subsystem 510 also may provide one or more tangible computer-readable storage media 516 for storing the basic programming and data constructs that provide the functionality of some embodiments. Software (programs, code modules, instructions) that, when executed by a processor, provide the functionality described herein may be stored in storage subsystem 510. These software modules or instructions may be executed by processing units 504. Storage subsystem 510 may also provide a repository for storing data used in accordance with the present invention.

Storage subsystem 300 may also include a computer-readable storage media reader that can further be connected to computer-readable storage media 516. Together and, optionally, in combination with system memory 518, computer-readable storage media 516 may comprehensively represent remote, local, fixed, and/or removable storage devices plus storage media for temporarily and/or more permanently containing, storing, transmitting, and retrieving computer-readable information.

Computer-readable storage media 516 containing program code, or portions of program code, may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 500.

By way of example, computer-readable storage media 516 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 516 may include, but is not limited to, Zip® drives, flash memory cards, universal serial bus (USB) flash drives, secure digital (SD) cards, DVD disks, digital video tape, and the like. Computer-readable storage media 516 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 500.

Communications subsystem 532 may provide a communication interface from computer system 500 and external computing devices via one or more communication networks, including local area networks (LANs), wide area networks (WANs) (e.g., the Internet), and various wireless telecommunications networks. As illustrated in FIG. 5, the communications subsystem 532 may include, for example, one or more network interface controllers (NICs) 534, such as Ethernet cards, Asynchronous Transfer Mode NICs, Token Ring NICs, and the like, as well as one or more wireless communications interfaces 536, such as wireless network interface controllers (WNICs), wireless network adapters, and the like. As illustrated in FIG. 5, the communications subsystem 532 may include, for example, one or more location determining features 538 such as one or several navigation system features and/or receivers, and the like. Additionally and/or alternatively, the communications subsystem 532 may include one or more modems (telephone, satellite, cable, ISDN), synchronous or asynchronous digital subscriber line (DSL) units, FireWire® interfaces, USB® interfaces, and the like. Communications subsystem 536 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 532 may be detachable components coupled to the computer system 500 via a computer network, a FireWire® bus, or the like, and/or may be physically integrated onto a motherboard of the computer system 500. Communications subsystem 532 also may be implemented in whole or in part by software.

In some embodiments, communications subsystem 532 may also receive input communication in the form of structured and/or unstructured data feeds, event streams, event updates, and the like, on behalf of one or more users who may use or access computer system 500. For example, communications subsystem 532 may be configured to receive data feeds in real-time from users of social networks and/or other communication services, web feeds such as Rich Site Summary (RSS) feeds, and/or real-time updates from one or more third party information sources (e.g., data aggregators 311). Additionally, communications subsystem 532 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 532 may output such structured and/or unstructured data feeds, event streams, event updates, and the like to one or more data stores 104 that may be in communication with one or more streaming data source computers coupled to computer system 500.

Due to the ever-changing nature of computers and networks, the description of computer system 500 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 6:
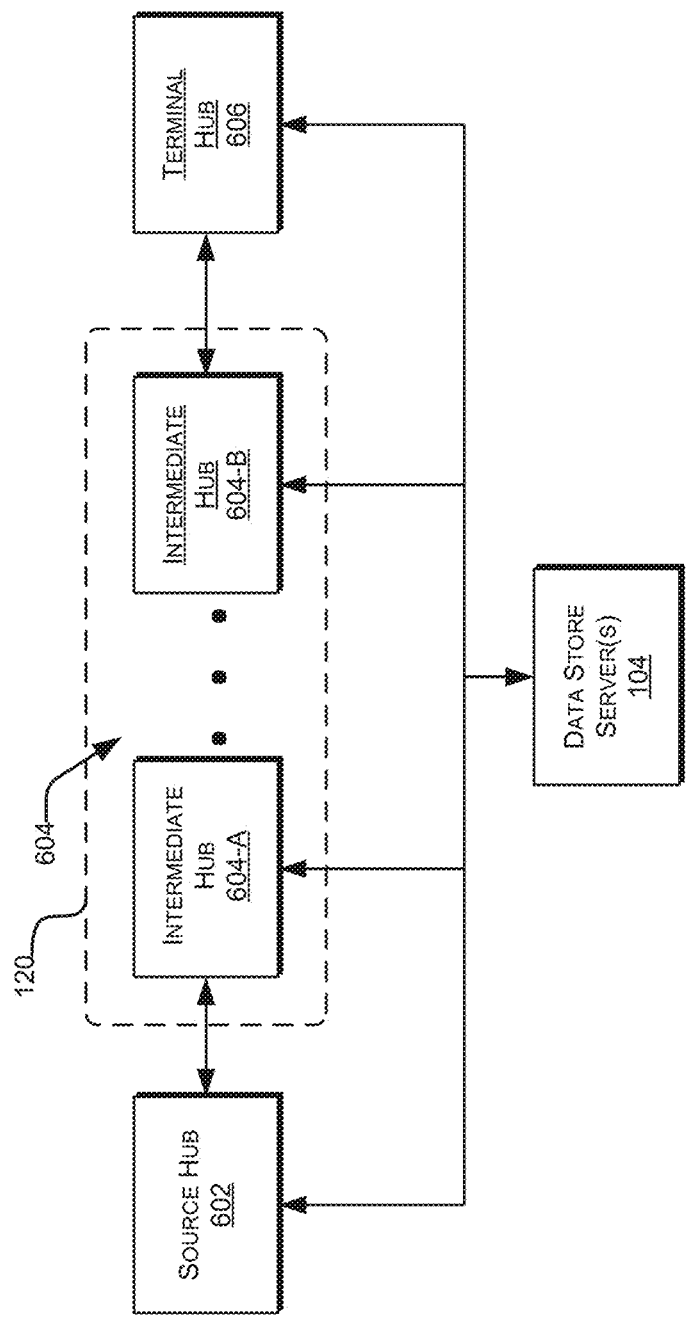
FIG. 6 is a block diagram illustrating one embodiment of the communication network.

With reference now to FIG. 6, a block diagram illustrating one embodiment of the communication network is shown. Specifically, FIG. 6 depicts one hardware configuration in which messages are exchanged between a source hub 602 via the communication network 120 that can include one or several intermediate hubs 604. In some embodiments, the source hub 602 can be any one or several components of the content distribution network generating and initiating the sending of a message, and the terminal hub 606 can be any one or several components of the content distribution network 100 receiving and not re-sending the message. In some embodiments, for example, the source hub 602 can be one or several of the user device 106, the supervisor device 110, and/or the server 102, and the terminal hub 606 can likewise be one or several of the user device 106, the supervisor device 110, and/or the server 102. In some embodiments, the intermediate hubs 604 can include any computing device that receives the message and resends the message to a next node.

As seen in FIG. 6, in some embodiments, each of the hubs 602, 604, 606 can be communicatingly connected with the data store 104. In such an embodiments, some or all of the hubs 602, 604, 606 can send information to the data store 104 identifying a received message and/or any sent or resent message. This information can, in some embodiments, be used to determine the completeness of any sent and/or received messages and/or to verify the accuracy and completeness of any message received by the terminal hub 606.

In some embodiments, the communication network 120 can be formed by the intermediate hubs 604. In some embodiments, the communication network 120 can comprise a single intermediate hub 604, and in some embodiments, the communication network 120 can comprise a plurality of intermediate hubs. In one embodiment, for example, and as depicted in FIG. 6, the communication network 120 includes a first intermediate hub 604-A and a second intermediate hub 604-B.

Figure 7:
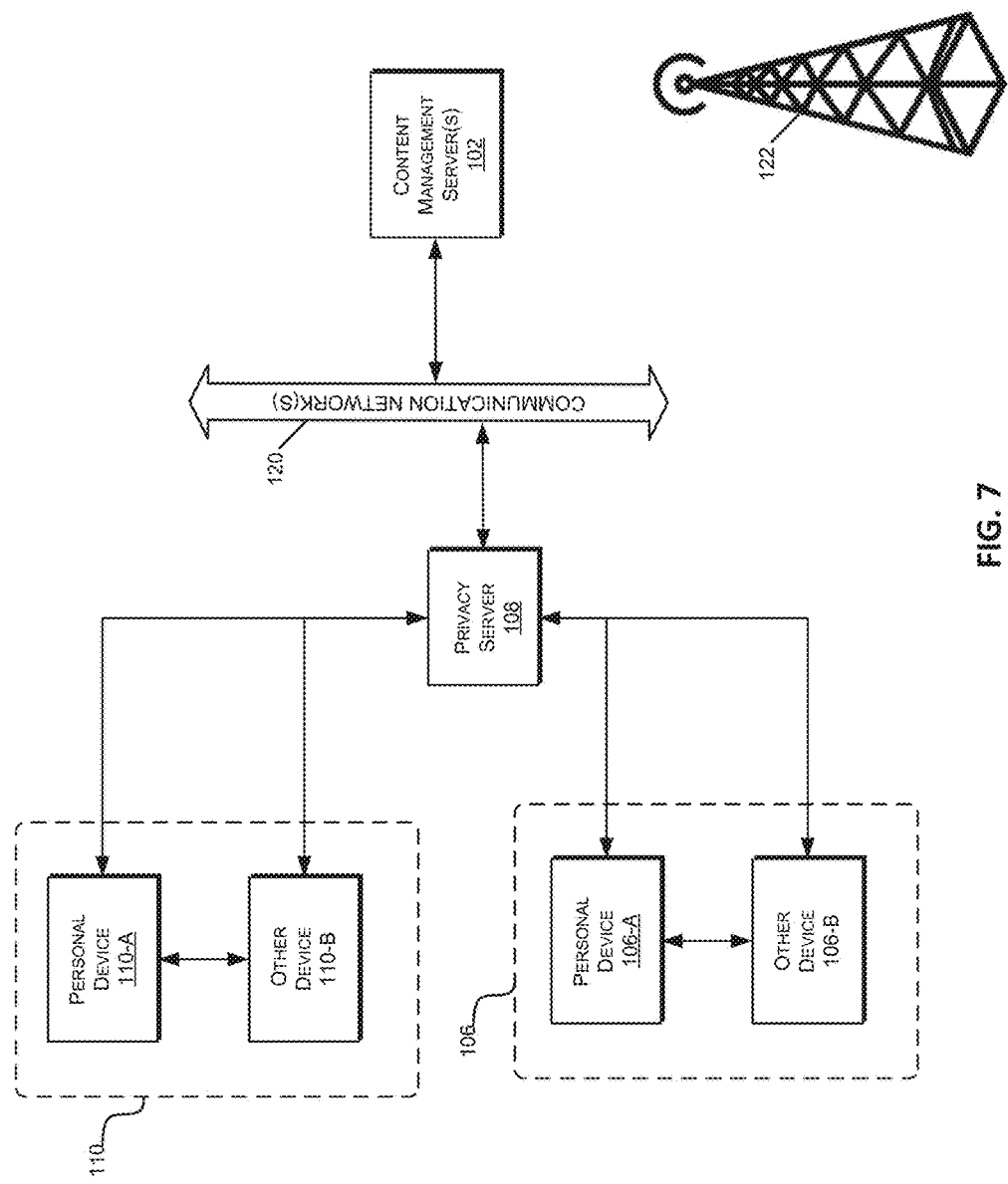
FIG. 7 is a block diagram illustrating one embodiment of user device and supervisor device communication.

With reference now to FIG. 7, a block diagram illustrating one embodiment of user device 106 and supervisor device 110 communication is shown. In some embodiments, for example, a user may have multiple devices that can connect with the content distribution network 100 to send or receive information. In some embodiments, for example, a user may have a personal device such as a mobile device, a Smartphone, a tablet, a Smartwatch, a laptop, a PC, or the like. In some embodiments, the other device can be any computing device in addition to the personal device. This other device can include, for example, a laptop, a PC, a Smartphone, a tablet, a Smartwatch, or the like. In some embodiments, the other device differs from the personal device in that the personal device is registered as such within the content distribution network 100 and the other device is not registered as a personal device within the content distribution network 100.

Specifically with respect to FIG. 7, the user device 106 can include a personal user device 106-A and one or several other user devices 106-B. In some embodiments, one or both of the personal user device 106-A and the one or several other user devices 106-B can be communicatingly connected to the content management server 102 and/or to the navigation system 122. Similarly, the supervisor device 110 can include a personal supervisor device 110-A and one or several other supervisor devices 110-B. In some embodiments, one or both of the personal supervisor device 110-A and the one or several other supervisor devices 110-B can be communicatingly connected to the content management server 102 and/or to the navigation system 122.

In some embodiments, the content distribution network can send one or more alerts to one or more user devices 106 and/or one or more supervisor devices 110 via, for example, the communication network 120. In some embodiments, the receipt of the alert can result in the launching of an application within the receiving device, and in some embodiments, the alert can include a link that, when selected, launches the application or navigates a web-browser of the device of the selector of the link to a page or portal associated with the alert. In some embodiments, this launched application can display one or several items or pieces of data contained in the alert.

In some embodiments, for example, the providing of this alert can include the identification of one or several user devices 106 and/or student-user accounts associated with the student-user and/or one or several supervisor devices 110 and/or supervisor-user accounts associated with the supervisor-user. After these one or several devices 106, 110 and/or accounts have been identified, the providing of this alert can include determining an active device of the devices 106, 110 based on determining which of the devices 106, 110 and/or accounts are actively being used, and then providing the alert to that active device.

Specifically, if the user is actively using one of the devices 106, 110 such as the other user device 106-B and the other supervisor device 110-B, and/or accounts, the alert can be provided to the user via that other device 106-B, 110-B and/or account that is actively being used. If the user is not actively using an other device 106-B, 110-B and/or account, a personal device 106-A, 110-A device, such as a smart phone or tablet, can be identified and the alert can be provided to this personal device 106-A, 110-A. In some embodiments, the alert can include code to direct the default device to provide an indicator of the received alert such as, for example, an aural, tactile, or visual indicator of receipt of the alert.

In some embodiments, the recipient device 106, 110 of the alert can provide an indication of receipt of the alert. In some embodiments, the presentation of the alert can include the control of the I/O subsystem 526 to, for example, provide an aural, tactile, and/or visual indicator of the alert and/or of the receipt of the alert. In some embodiments, this can include controlling a screen of the supervisor device 110 to display the alert, data contained in alert and/or an indicator of the alert.

Figure 8:
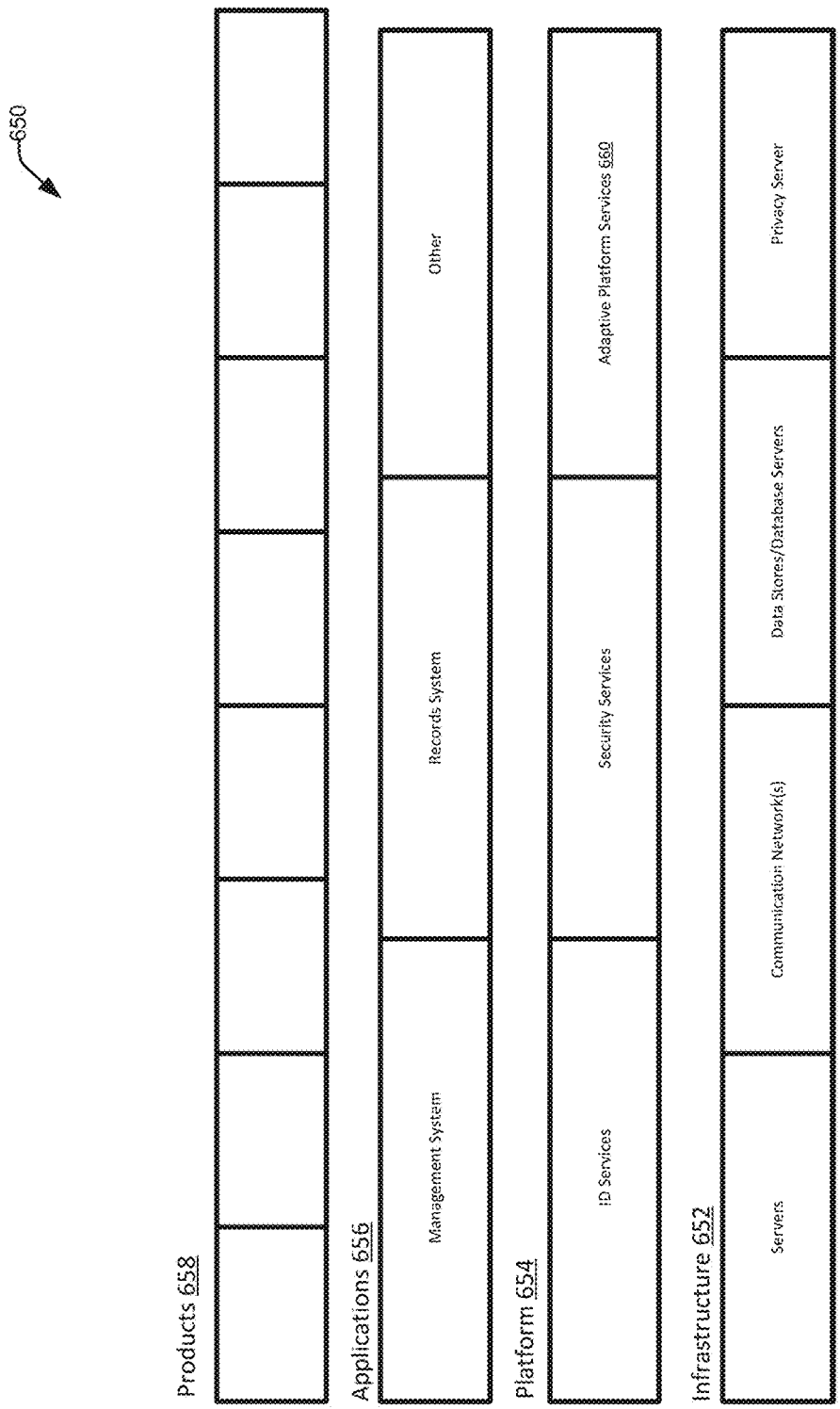
FIG. 8 is a schematic illustration of one embodiment of a computing stack.

With reference now to FIG. 8, a schematic illustration of one embodiment of an application stack, and particularly of a stack 650 is shown. In some embodiments, the content distribution network 100 can comprise a portion of the stack 650 that can include an infrastructure layer 652, a platform layer 654, an applications layer 656, and a products layer 658. In some embodiments, the stack 650 can comprise some or all of the layers, hardware, and/or software to provide one or several desired functionalities and/or productions.

As depicted in FIG. 8, the infrastructure layer 652 can include one or several servers, communication networks, data stores, privacy servers, and the like. In some embodiments, the infrastructure layer can further include one or several user devices 106 and/or supervisor devices 110 connected as part of the content distribution network.

The platform layer can include one or several platform software programs, modules, and/or capabilities. These can include, for example, identification services, security services, and/or adaptive platform services 660. In some embodiments, the identification services can, for example, identify one or several users, components of the content distribution network 100, or the like. The security services can monitor the content distribution network for one or several security threats, breaches, viruses, malware, or the like. The adaptive platform services 660 can receive information from one or several components of the content distribution network 100 and can provide predictions, models, recommendations, or the like based on that received information. The functionality of the adaptive platform services 660 will be discussed in greater detail in FIGS. 9A-9C, below.

The applications layer 656 can include software or software modules upon or in which one or several product softwares or product software modules can operate. In some embodiments, the applications layer 656 can include, for example, a management system, record system, or the like. In some embodiments, the management system can include, for example, a Learning Management System (LMS), a Content Management System (CMS), or the like. The management system can be configured to control the delivery of one or several resources to a user and/or to receive one or several responses from the user. In some embodiments, the records system can include, for example, a virtual gradebook, a virtual counselor, or the like.

The products layer can include one or several software products and/or software module products. These software products and/or software module products can provide one or several services and/or functionalities to one or several users of the software products and/or software module products.

Figure 9A:
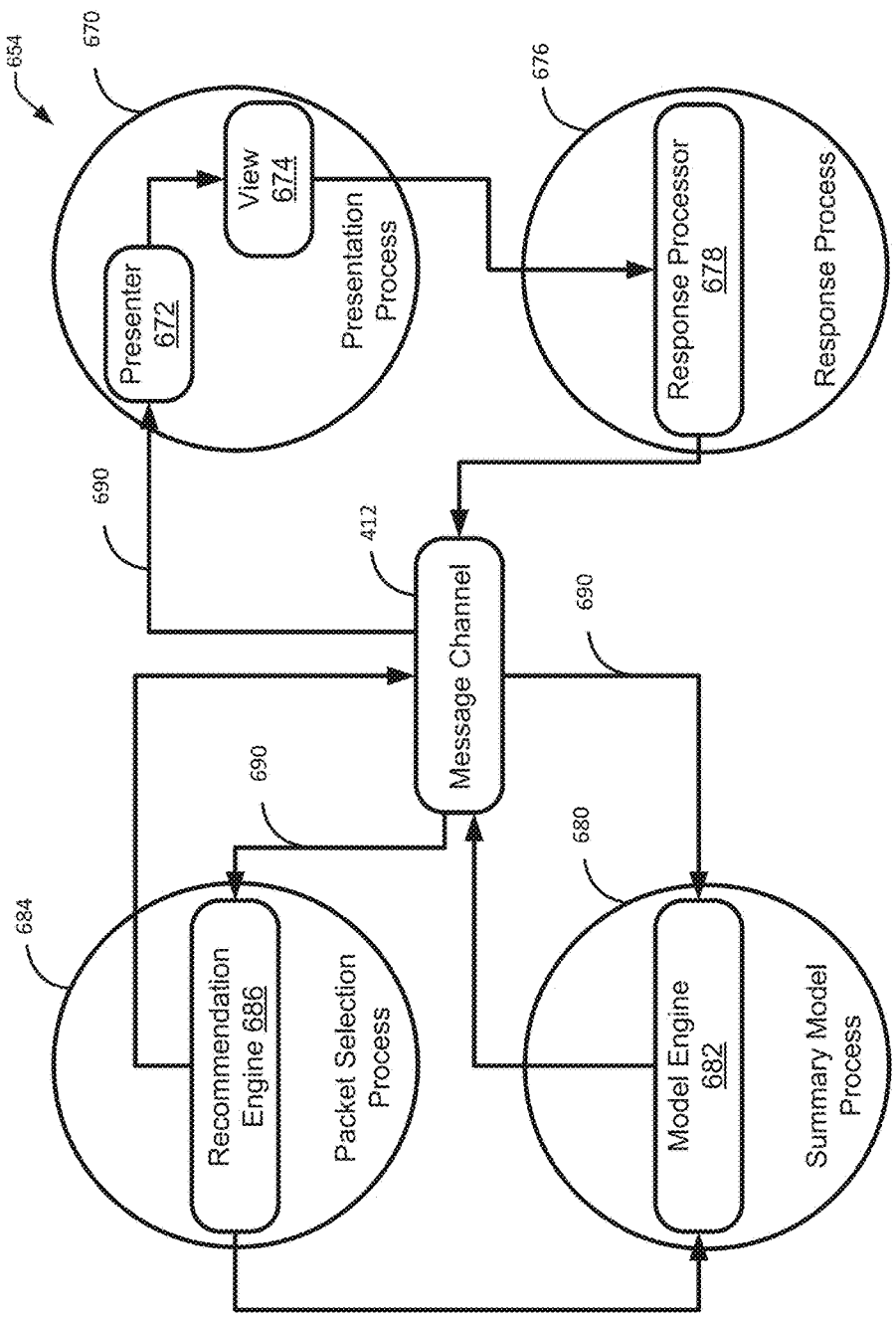
FIG. 9A is a schematic illustration of one embodiment of communication and processing flow of modules within the content distribution network.
Figure 9B:
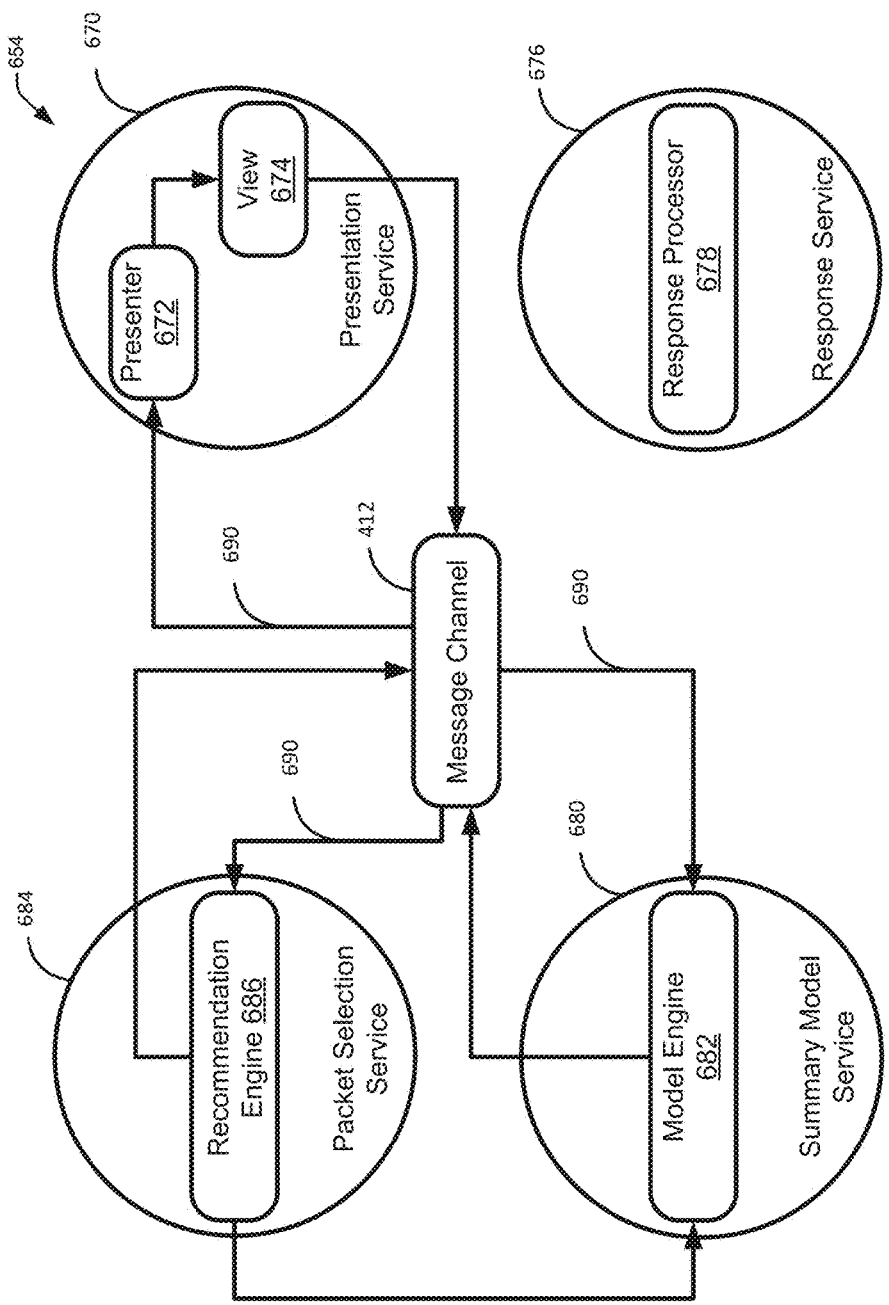
FIG. 9B is a schematic illustration of another embodiment of communication and processing flow of modules within the content distribution network.
Figure 9C:
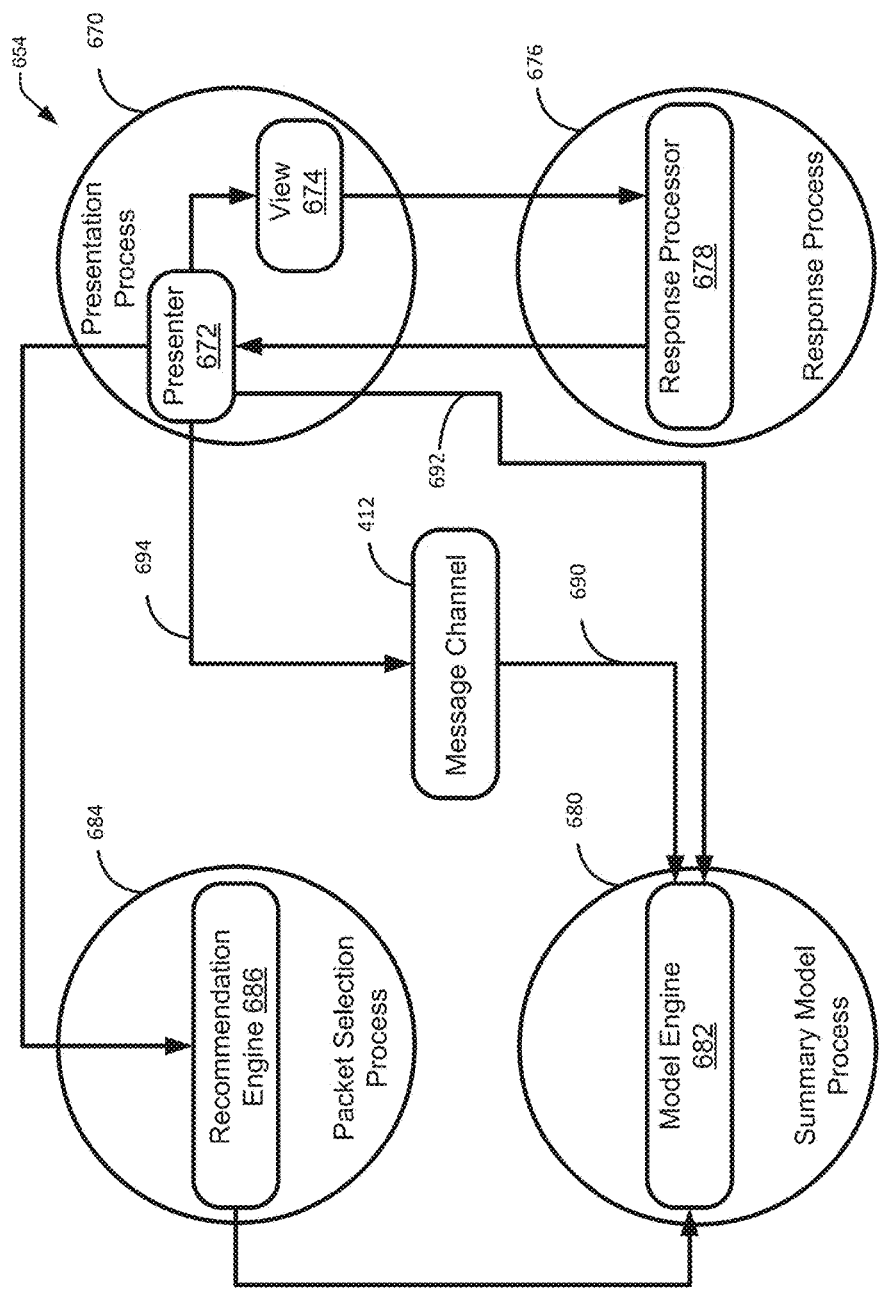
FIG. 9C is a schematic illustration of an additional embodiment of communication and processing flow of modules within the content distribution network.

With reference now to FIG. 9A-9C, schematic illustrations of embodiments of communication and processing flow of modules within the content distribution network 100 are shown. In some embodiments, the communication and processing can be performed in portions of the platform layer 654 and/or applications layer 656. FIG. 9A depicts a first embodiment of such communications or processing that can be in the platform layer 654 and/or applications layer 656 via the message channel 412.

The platform layer 654 and/or applications layer 656 can include a plurality of modules that can be embodied in software or hardware. In some embodiments, some or all of the modules can be embodied in hardware and/or software at a single location, and in some embodiments, some or all of these modules can be embodied in hardware and/or software at multiple locations. These modules can perform one or several processes including, for example, a presentation process 670, a response process 676, a summary model process 680, and a packet selection process 684.

The presentation process 670 can, in some embodiments, include one or several methods and/or steps to deliver content to one or several user devices 106 and/or supervisor devices 110. The presentation process 670 can be performed by a presenter module 672 and a view module 674. The presenter module 672 can be a hardware or software module of the content distribution network 100, and specifically of the server 102. In some embodiments, the presenter module 672 can include one or several portions, features, and/or functionalities that are located on the server 102 and/or one or several portions, features, and/or functionalities that are located on the user device 106. In some embodiments, the presenter module 672 can be embodied in the presentation system 408.

The presenter module 672 can control the providing of content to one or several user devices 106 and/or supervisor devices 110. Specifically, the presenter module 672 can control the generation of one or several messages to provide content to one or several desired user devices 106 and/or supervisor devices 110. The presenter module 672 can further control the providing of these one or several messages to the desired one or several desired user devices 106 and/or supervisor devices 110. Thus, in some embodiments, the presenter module 672 can control one or several features of the communications subsystem 532 to generate and send one or several electrical signals comprising content to one or several user devices 106 and/or supervisor devices 110.

In some embodiments, the presenter module 672 can control and/or manage a portion of the presentation functions of the presentation process 670, and can specifically manage an "outer loop" of presentation functions. As used herein, the outer loop refers to tasks relating to the tracking of a user's progress through all or a portion of a group of data packets. In some embodiments, this can include the identification of one or several completed data packets or nodes and/or the non-adaptive selection of one or several next data packets or nodes according to, for example, one or several fixed rules. Such non-adaptive selection does not rely on the use of predictive models, but rather on rules identifying next data packets based on data relating to the completion of one or several previously completed data packets or assessments and/or whether one or several previously completed data packets were successfully completed.

In some embodiments, and due to the management of the outer loop of presentation functions including the non-adaptive selection of one or several next data packets, nodes, or tasks by the presenter module, the presenter module can function as a recommendation engine referred to herein as a first recommendation engine or a rules-based recommendation engine. In some embodiments, the first recommendation engine can be configured to select a next node for a user based on one or all of: the user's current location in the content network; potential next nodes; the user's history including the user's previous responses; and one or several guard conditions associated with the potential next nodes. In some embodiments, a guard condition defines one or several prerequisites for entry into, or exit from, a node.

In some embodiments, the presenter module 672 can include a portion located on the server 102 and/or a portion located on the user device 106. In some embodiments, the portion of the presenter module 672 located on the server 102 can receive data packet information and provide a subset of the received data packet information to the portion of the presenter module 672 located on the user device 106. In some embodiments, this segregation of functions and/or capabilities can prevent solution data from being located on the user device 106 and from being potentially accessible by the user of the user device 106.

In some embodiments, the portion of the presenter module 672 located on the user device 106 can be further configured to receive the subset of the data packet information from the portion of the presenter module 672 located on the server 102 and provide that subset of the data packet information to the view module 674. In some embodiments, the portion of the presenter module 672 located on the user device 106 can be further configured to receive a content request from the view module 674 and to provide that content request to the portion of the presenter module 674 located on the server 102.

The view module 674 can be a hardware or software module of some or all of the user devices 106 and/or supervisor devices 110 of the content distribution network 100. The view module 674 can receive one or several electrical signals and/or communications from the presenter module 672 and can provide the content received in those one or several electrical signals and/or communications to the user of the user device 106 and/or supervisor device 110 via, for example, the I/O subsystem 526.

In some embodiments, the view module 674 can control and/or monitor an "inner loop" of presentation functions. As used herein, the inner loop refers to tasks relating to the tracking and/or management of a user's progress through a data packet. This can specifically relate to the tracking and/or management of a user's progression through one or several pieces of content, questions, assessments, and/or the like of a data packet. In some embodiments, this can further include the selection of one or several next pieces of content, next questions, next assessments, and/or the like of the data packet for presentation and/or providing to the user of the user device 106.

In some embodiments, one or both of the presenter module 672 and the view module 674 can comprise one or several presentation engines. In some embodiments, these one or several presentation engines can comprise different capabilities and/or functions. In some embodiments, one of the presentation engines can be configured to track the progress of a user through a single data packet, task, content item, or the like, and in some embodiments, one of the presentation engines can track the progress of a user through a series of data packets, tasks, content items, or the like.

The response process 676 can comprise one or several methods and/or steps to evaluate a response. In some embodiments, this can include, for example, determining whether the response comprises a desired response and/or an undesired response. In some embodiments, the response process 676 can include one or several methods and/or steps to determine the correctness and/or incorrectness of one or several received responses. In some embodiments, this can include, for example, determining the correctness and/or incorrectness of a multiple choice response, a true/false response, a short answer response, an essay response, or the like. In some embodiments, the response processor can employ, for example, natural language processing, semantic analysis, or the like in determining the correctness or incorrectness of the received responses.

In some embodiments, the response process 676 can be performed by a response processor 678. The response processor 678 can be a hardware or software module of the content distribution network 100, and specifically of the server 102. In some embodiments, the response processor 678 can be embodied in the response system 406. In some embodiments, the response processor 678 can be communicatingly connected to one or more of the modules of the presentation process 760 such as, for example, the presenter module 672 and/or the view module 674. In some embodiments, the response processor 678 can be communicatingly connected with, for example, the message channel 412 and/or other components and/or modules of the content distribution network 100.

The summary model process 680 can comprise one or several methods and/or steps to generate and/or update one or several models. In some embodiments, this can include, for example, implementing information received either directly or indirectly from the response processor 678 to update one or several models. In some embodiments, the summary model process 680 can include the update of a model relating to one or several user attributes such as, for example, a user skill model, a user knowledge model, a learning style model, or the like. In some embodiments, the summary model process 680 can include the update of a model relating to one or several content attributes including attributes relating to a single content item and/or data packet and/or attributes relating to a plurality of content items and/or data packets. In some embodiments, these models can relate to an attribute of the one or several data packets such as, for example, difficulty, discrimination, required time, or the like.

In some embodiments, the summary model process 680 can be performed by the model engine 682. In some embodiments, the model engine 682 can be a hardware or software module of the content distribution network 100, and specifically of the server 102. In some embodiments, the model engine 682 can be embodied in the summary model system 404.

In some embodiments, the model engine 682 can be communicatingly connected to one or more of the modules of the presentation process 760 such as, for example, the presenter module 672 and/or the view module 674, can be connected to the response processor 678 and/or the recommendation. In some embodiment, the model engine 682 can be communicatingly connected to the message channel 412 and/or other components and/or modules of the content distribution network 100.

The packet selection process 684 can comprise one or several steps and/or methods to identify and/or select a data packet for presentation to a user. In some embodiments, this data packet can comprise a plurality of data packets. In some embodiments, this data packet can be selected according to one or several models updated as part of the summary model process 680. In some embodiments, this data packet can be selected according to one or several rules, probabilities, models, or the like. In some embodiments, the one or several data packets can be selected by the combination of a plurality of models updated in the summary model process 680 by the model engine 682. In some embodiments, these one or several data packets can be selected by a recommendation engine 686. The recommendation engine 686 can be a hardware or software module of the content distribution network 100, and specifically of the server 102. In some embodiments, the recommendation engine 686 can be embodied in the packet selection system 402. In some embodiments, the recommendation engine 686 can be communicatingly connected to one or more of the modules of the presentation process 670, the response process 676, and/or the summary model process 680 either directly and/or indirectly via, for example, the message channel.

In some embodiments, and as depicted in FIG. 9A, a presenter module 672 can receive a data packet for presentation to a user device 106. This data packet can be received, either directly or indirectly from a recommendation engine 686. In some embodiments, for example, the presenter module 672 can receive a data packet for providing to a user device 106 from the recommendation engine 686, and in some embodiments, the presenter module 672 can receive an identifier of a data packet for providing to a user device 106 via a view module 674. This can be received from the recommendation engine 686 via a message channel 412.

Specifically, in some embodiments, the recommendation engine 686 can provide data to the message channel 412 indicating the identification and/or selection of a data packet for providing to a user via a user device 106. In some embodiments, this data indicating the identification and/or selection of the data packet can identify the data packet and/or can identify the intended recipient of the data packet.

The message channel 412 can output this received data in the form of a data stream 690 which can be received by, for example, the presenter module 672, the model engine 682, and/or the recommendation engine 686. In some embodiments, some or all of: the presenter module 672, the model engine 682, and/or the recommendation engine 686 can be configured to parse and/or filter the data stream 690 to identify data and/or events relevant to their operation. Thus, for example, the presenter module 672 can be configured to parse the data stream for information and/or events relevant to the operation of the presenter module 672.

In some embodiments, the presenter module 672 can extract the data packet from the data stream 690 and/or extract data identifying the data packet and/or indicating the selecting of a data packet from the data stream. In the event that data identifying the data packet is extracted from the data stream 690, the presenter module 672 can request and receive the data packet from the database server 104, and specifically from the content library database 303. In embodiments in which data indicating the selection of a data packet is extracted from the data stream 690, the presenter module 672 can request and receive identification of the data packet from the recommendation engine 686 and then request and receive the data packet from the database server 104, and specifically from the content library database 303, and in some embodiments in which data indicating the selection of a data packet is extracted from the data stream 690, the presenter module 672 can request and receive the data packet from the recommendation engine 686.

The presenter module can then provide the data packet and/or portions of the data packet to the view module 674. In some embodiments, for example, the presenter module 672 can retrieve one or several rules and/or conditions that can be, for example, associated with the data packet and/or stored in the database server 104. In some embodiments, these rules and/or conditions can identify portions of a data packet for providing to the view module 674 and/or portions of a data packet to not provide to the view module 674. In some embodiments, for example, sensitive portions of a data packet, such as, for example, solution information to any questions associated with a data packet, is not provided to the view module 674 to prevent the possibility of undesired access to those sensitive portions of the data packet. Thus, in some embodiments, the one or several rules and/or conditions can identify portions of the data packet for providing to the view module 674 and/or portions of the data packet for not providing to the view module.

In some embodiments, the presenter module 672 can, according to the one or more rules and/or conditions, generate and transmit an electronic message containing all or portions of the data packet to the view module 674. The view module 674 can receive these all or portions of the data packet and can provide all or portions of this information to the user of the user device 106 associated with the view module 674 via, for example, the I/O subsystem 526. In some embodiments, as part of the providing of all or portions of the data packet to the user of the view module 674, one or several user responses can be received by the view module 674. In some embodiments, these one or several user responses can be received via the I/O subsystem 526 of the user device 106.

After one or several user responses have been received, the view module 674 can provide the one or several user responses to the response processor 678. In some embodiments, these one or several responses can be directly provided to the response processor 678, and in some embodiments, these one or several responses can be provided indirectly to the response processor 678 via the message channel 412.

After the response processor 678 receives the one or several responses, the response processor 678 can determine whether the responses are desired responses and/or the degree to which the received responses are desired responses. In some embodiments, the response processor can make this determination via, for example, use of one or several techniques, including, for example, natural language processing (NLP), semantic analysis, or the like.

In some embodiments, the response processor can determine whether a response is a desired response and/or the degree to which a response is a desired response with comparative data which can be associated with the data packet. In some embodiments, this comparative data can comprise, for example, an indication of a desired response and/or an indication of one or several undesired responses, a response key, a response rubric comprising one criterion or several criteria for determining the degree to which a response is a desired response, or the like. In some embodiments, the comparative data can be received as a portion of and/or associated with a data packet. In some embodiments, the comparative data can be received by the response processor 678 from the presenter module 672 and/or from the message channel 412. In some embodiments, the response data received from the view module 674 can comprise data identifying the user and/or the data packet or portion of the data packet with which the response is associated. In some embodiments in which the response processor 678 merely receives data identifying the data packet and/or portion of the data packet associated with the one or several responses, the response processor 678 can request and/or receive comparative data from the database server 104, and specifically from the content library database 303 of the database server 104.

After the comparative data has been received, the response processor 678 determines whether the one or several responses comprise desired responses and/or the degree to which the one or several responses comprise desired responses. The response processor can then provide the data characterizing whether the one or several responses comprise desired response and/or the degree to which the one or several responses comprise desired responses to the message channel 412. The message channel can, as discussed above, include the output of the response processor 678 in the data stream 690 which can be constantly output by the message channel 412.

In some embodiments, the model engine 682 can subscribe to the data stream 690 of the message channel 412 and can thus receive the data stream 690 of the message channel 412 as indicated in FIG. 9A. The model engine 682 can monitor the data stream 690 to identify data and/or events relevant to the operation of the model engine. In some embodiments, the model engine 682 can monitor the data stream 690 to identify data and/or events relevant to the determination of whether a response is a desired response and/or the degree to which a response is a desired response.

When a relevant event and/or relevant data are identified by the model engine, the model engine 682 can take the identified relevant event and/or relevant data and modify one or several models. In some embodiments, this can include updating and/or modifying one or several models relevant to the user who provided the responses, updating and/or modifying one or several models relevant to the data packet associated with the responses, and/or the like. In some embodiments, these models can be retrieved from the database server 104, and, in some embodiments, can be retrieved from the model data source 309 of the database server 104.

After the models have been updated, the updated models can be stored in the database server 104. In some embodiments, the model engine 682 can send data indicative of the event of the completion of the model update to the message channel 412. The message channel 412 can incorporate this information into the data stream 690 which can be received by the recommendation engine 686. The recommendation engine 686 can monitor the data stream 690 to identify data and/or events relevant to the operation of the recommendation engine 686. In some embodiments, the recommendation engine 686 can monitor the data stream 690 to identify data and/or events relevant to the updating of one or several models by the model engine 682.

When the recommendation engine 686 identifies information in the data stream 690 indicating the completion of the summary model process 680 for models relevant to the user providing the response and/or for models relevant to the data packet provided to the user, the recommendation engine 686 can identify and/or select a next data packet for providing to the user and/or to the presentation process 470. In some embodiments, this selection of the next data packet can be performed according to one or several rules and/or conditions. After the next data packet has been selected, the recommendation engine 686 can provide information to the model engine 682 identifying the next selected data packet and/or to the message channel 412 indicating the event of the selection of the next content item. After the message channel 412 receives information identifying the selection of the next content item and/or receives the next content item, the message channel 412 can include this information in the data stream 690 and the process discussed with respect to FIG. 9A can be repeated.

With reference now to FIG. 9B, a schematic illustration of a second embodiment of communication or processing that can be in the platform layer 654 and/or applications layer 656 via the message channel 412 is shown. In the embodiment depicted in FIG. 9B, the data packet provided to the presenter module 672 and then to the view module 674 does not include a prompt for a user response and/or does not result in the receipt of a user response. As no response is received, when the data packet is completed, nothing is provided to the response processor 678, but rather data indicating the completion of the data packet is provided from one of the view module 674 and/or the presenter module 672 to the message channel 412. The data is then included in the data stream 690 and is received by the model engine 682 which uses the data to update one or several models. After the model engine 682 has updated the one or several models, the model engine 682 provides data indicating the completion of the model updates to the message channel 412. The message channel 412 then includes the data indicating the completion of the model updates in the data stream 690 and the recommendation engine 686, which can subscribe to the data stream 690, can extract the data indicating the completion of the model updates from the data stream 690. The recommendation engine 686 can then identify a next one or several data packets for providing to the presenter module 672, and the recommendation engine 686 can then, either directly or indirectly, provide the next one or several data packets to the presenter module 672.

In some embodiments, of the communication as shown in FIGS. 9A and 9B, all communications between any of the presenter module 672, the response processor 678, the model engine 682, and the recommendation engine 686 can pass through the message channel 412. Alternatively, in some embodiments, some of the communications between any of the presenter module 672, the response processor 678, the model engine 682, and the recommendation engine 686 can pass through the message channel and others of the communications between any of the presenter module 672, the response processor 678, the model engine 682, and the recommendation engine 686 can be direct.

With reference now to FIG. 9C, a schematic illustration of an embodiment of dual communication, or hybrid communication, in the platform layer 654 and/or applications layer 656 is shown. Specifically, in this embodiment, some communication is synchronous with the completion of one or several tasks and some communication is asynchronous. In the embodiment depicted in FIG. 9C, the presenter module 972 communicates synchronously with the model engine 682 via a direct communication 692 and communicates asynchronously with the model engine 682 via the message channel 412.

In some embodiments, and as depicted in FIG. 9C, the synchronous communication and/or the operation of the presenter module 672, the response processor 678, the model engine 682, and the recommendation engine 686 can be directed and/or controlled by a controller. In some embodiments, this controller can be part of the server 102 and/or located in any one or more of the presenter module 672, the response processor 678, the model engine 682, and the recommendation engine 686. In some embodiments, this controller can be located in the presenter module 672, which presenter module can control communications with and between itself and the response processor 678, the model engine 682, and the recommendation engine 686, and the presenter module can thus control the functioning of the response processor 678, the model engine 682, and the recommendation engine 686.

Specifically, and with reference to FIG. 9C, the presenter module 672 can receive and/or select a data packet for presentation to the user device 106 via the view module 674. In some embodiments, the presenter module 672 can identify all or portions of the data packet that can be provided to the view module 674 and portions of the data packet for retaining from the view module 674. In some embodiments, the presenter module can provide all or portions of the data packet to the view module 674. In some embodiments, and in response to the receipt of all or portions of the data packet, the view module 674 can provide a confirmation of receipt of the all or portions of the data packet and can provide those all or portions of the data packet to the user via the user device 106. In some embodiments, the view module 674 can provide those all or portions of the data packet to the user device 106 while controlling the inner loop of the presentation of the data packet to the user via the user device 106.

After those all or portions of the data packet have been provided to the user device 106, a response indicative of the completion of one or several tasks associated with the data packet can be received by the view module 674 from the user device 106, and specifically from the I/O subsystem 526 of the user device 106. In response to this receive, the view module 674 can provide an indication of this completion status to the presenter module 672 and/or can provide the response to the response processor 678.

After the response has been received by the response processor 678, the response processor 678 can determine whether the received response is a desired response. In some embodiments, this can include, for example, determining whether the response comprises a correct answer and/or the degree to which the response comprises a correct answer.

After the response processor has determined whether the received response is a desired response, the response processor 678 can provide an indicator of the result of the determination of whether the received response is a desired response to the presenter module 672. In response to the receipt of the indicator of whether the result of the determination of whether the received response is a desired response, the presenter module 672 can synchronously communicate with the model engine 682 via a direct communication 692 and can asynchronously communicate with model engine 682 via the message channel 412. In some embodiments, the synchronous communication can advantageously include two-way communication between the model engine 682 and the presenter module 672 such that the model engine 682 can provide an indication to the presenter module 672 when model updating is completed by the model engine.

After the model engine 682 has received one or both of the synchronous and asynchronous communications, the model engine 682 can update one or several models relating to, for example, the user, the data packet, or the like. After the model engine 682 has completed the updating of the one or several models, the model engine 682 can send a communication to the presenter module 672 indicating the completion of the updated one or several modules.

After the presenter module 672 receives the communication indicating the completion of the updating of the one or several models, the presenter module 672 can send a communication to the recommendation engine 686 requesting identification of a next data packet. As discussed above, the recommendation engine 686 can then retrieve the updated model and retrieve the user information. With the updated models and the user information, the recommendation engine can identify a next data packet for providing to the user, and can provide the data packet to the presenter module 672. In some embodiments, the recommendation engine 686 can further provide an indication of the next data packet to the model engine 682, which can use this information relating to the next data packet to update one or several models, either immediately, or after receiving a communication from the presenter module 672 subsequent to the determination of whether a received response for that data packet is a desired response.

With reference now to FIG. 9D, a schematic illustration of one embodiment of the presentation process 670 is shown. Specifically, FIG. 9D depicts multiple portions of the presenter module 672, namely, the external portion 673 and the internal portion 675. In some embodiment, the external portion 673 of the presenter module 672 can be located in the server, and in some embodiments, the internal portion 675 of the presenter module 672 can be located in the user device 106. In some embodiments, the external portion 673 of the presenter module can be configured to communicate and/or exchange data with the internal portion 675 of the presenter module 672 as discussed herein. In some embodiments, for example, the external portion 673 of the presenter module 672 can receive a data packet and can parse the data packet into portions for providing to the internal portion 675 of the presenter module 672 and portions for not providing to the internal portion 675 of the presenter module 672. In some embodiments, the external portion 673 of the presenter module 672 can receive a request for additional data and/or an additional data packet from the internal portion 675 of the presenter module 672. In such an embodiments, the external portion 673 of the presenter module 672 can identify and retrieve the requested data and/or the additional data packet from, for example, the database server 104 and more specifically from the content library database 104.

Figure 10A:
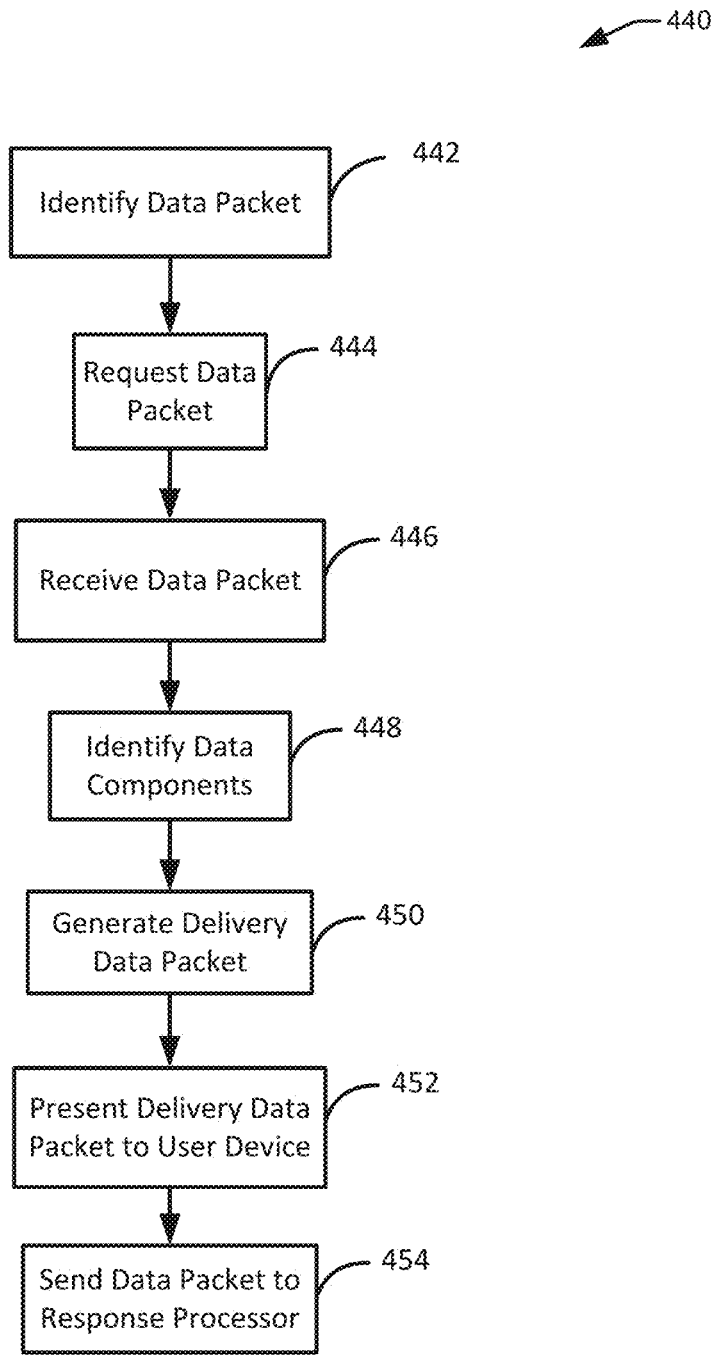
FIG. 10A is a flowchart illustrating one embodiment of a process for data management.

With reference now to FIG. 10A, a flowchart illustrating one embodiment of a process 440 for data management is shown. In some embodiments, the process 440 can be performed by the content management server 102, and more specifically by the presentation system 408 and/or by the presentation module or presentation engine. In some embodiments, the process 440 can be performed as part of the presentation process 670.

The process 440 begins at block 442, wherein a data packet is identified. In some embodiments, the data packet can be a data packet for providing to a student-user. In some embodiments, the data packet can be identified based on a communication received either directly or indirectly from the recommendation engine 686.

After the data packet has been identified, the process 440 proceeds to block 444, wherein the data packet is requested. In some embodiments, this can include the requesting of information relating to the data packet such as the data forming the data packet. In some embodiments, this information can be requested from, for example, the content library database 303. After the data packet has been requested, the process 440 proceeds to block 446, wherein the data packet is received. In some embodiments, the data packet can be received by the presentation system 408 from, for example, the content library database 303.

After the data packet has been received, the process 440 proceeds to block 448, wherein one or several data components are identified. In some embodiments, for example, the data packet can include one or several data components which can, for example, contain different data. In some embodiments, one of these data components, referred to herein as a presentation component, can include content for providing to the student user, which content can include one or several requests and/or questions and/or the like. In some embodiments, one of these data components, referred to herein as a response component, can include data used in evaluating one or several responses received from the user device 106 in response to the data packet, and specifically in response to the presentation component and/or the one or several requests and/or questions of the presentation component. Thus, in some embodiments, the response component of the data packet can be used to ascertain whether the user has provided a desired response or an undesired response.

After the data components have been identified, the process 440 proceeds to block 450, wherein a delivery data packet is identified. In some embodiments, the delivery data packet can include the one or several data components of the data packets for delivery to a user such as the student-user via the user device 106. In some embodiments, the delivery packet can include the presentation component, and in some embodiments, the delivery packet can exclude the response packet. After the delivery data packet has been generated, the process 440 proceeds to block 452, wherein the delivery data packet is provided to the user device 106 and more specifically to the view module 674. In some embodiments, this can include providing the delivery data packet to the user device 106 via, for example, the communication network 120.

After the delivery data packet has been provided to the user device 106, the process 440 proceeds to block 454, wherein the data packet and/or one or several components thereof are sent to and/or provided to the response processor 678. In some embodiments, this sending of the data packet and/or one or several components thereof to the response processor can include receiving a response from the student-user, and sending the response to the student-user to the response processor simultaneous with the sending of the data packet and/or one or several components thereof to the response processor. In some embodiments, for example, this can include providing the response component to the response processor. In some embodiments, the response component can be provided to the response processor from the presentation system 408.

Figure 10B:
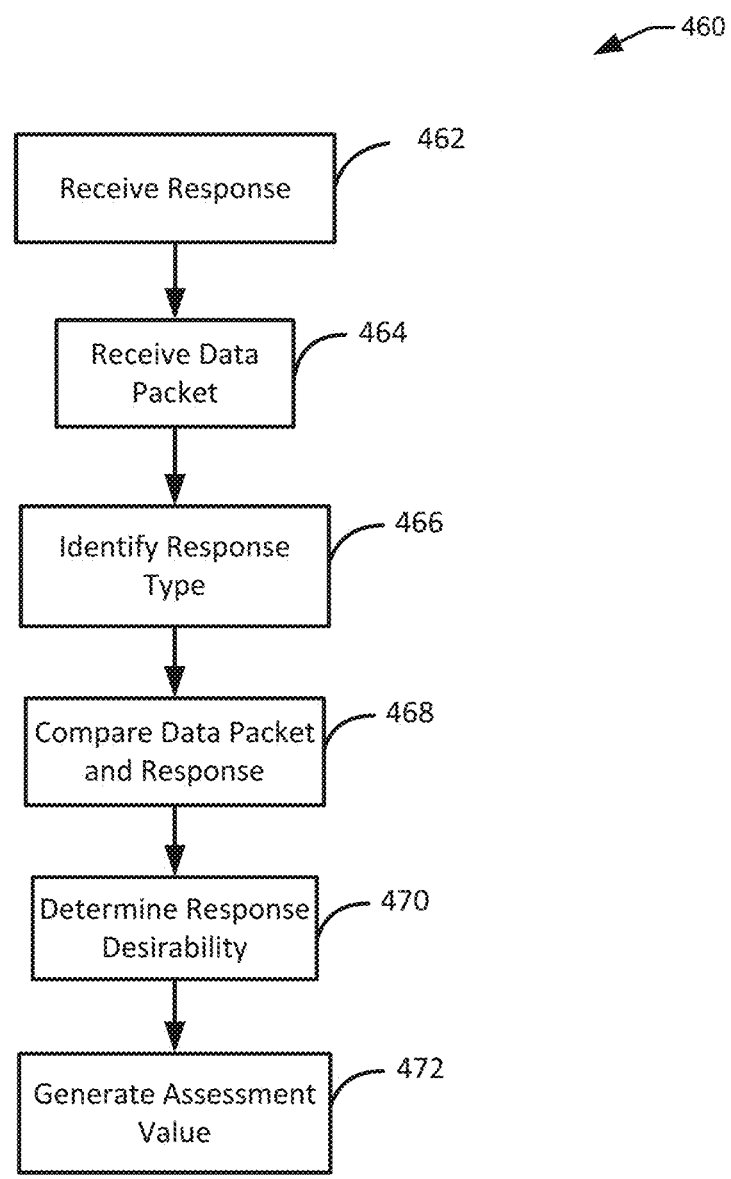
FIG. 10B is a flowchart illustrating one embodiment of a process for evaluating a response.

With reference now to FIG. 10B, a flowchart illustrating one embodiment of a process 460 for evaluating a response is shown. In some embodiments, the process can be performed as a part of the response process 676 and can be performed by, for example, the response system 406 and/or by the response processor 678. In some embodiments, the process 460 can be performed by the response system 406 in response to the receipt of a response, either directly or indirectly, from the user device 106 or from the view module 674.

The process 460 begins at block 462, wherein a response is received from, for example, the user device 106 via, for example, the communication network 120. After the response has been received, the process 460 proceeds to block 464, wherein the data packet associated with the response is received. In some embodiments, this can include receiving all or one or several components of the data packet such as, for example, the response component of the data packet. In some embodiments, the data packet can be received by the response processor from the presentation engine.

After the data packet has been received, the process 460 proceeds to block 466, wherein the response type is identified. In some embodiments, this identification can be performed based on data, such as metadata associated with the response. In other embodiments, this identification can be performed based on data packet information such as the response component.

In some embodiments, the response type can identify one or several attributes of the one or several requests and/or questions of the data packet such as, for example, the request and/or question type. In some embodiments, this can include identifying some or all of the one or several requests and/or questions as true/false, multiple choice, short answer, essay, or the like.

After the response type has been identified, the process 460 proceeds to block 468, wherein the data packet and the response are compared to determine whether the response comprises a desired response and/or an undesired response. In some embodiments, this can include comparing the received response and the data packet to determine if the received response matches all or portions of the response component of the data packet, to determine the degree to which the received response matches all or portions of the response component, to determine the degree to which the receive response embodies one or several qualities identified in the response component of the data packet, or the like. In some embodiments, this can include classifying the response according to one or several rules. In some embodiments, these rules can be used to classify the response as either desired or undesired. In some embodiments, these rules can be used to identify one or several errors and/or misconceptions evidenced in the response. In some embodiments, this can include, for example: use of natural language processing software and/or algorithms; use of one or several digital thesauruses; use of lemmatization software, dictionaries, and/or algorithms; or the like.

After the data packet and the response have been compared, the process 460 proceeds to block 470 wherein response desirability is determined. In some embodiments, this can include, based on the result of the comparison of the data packet and the response, whether the response is a desired response or is an undesired response. In some embodiments, this can further include quantifying the degree to which the response is a desired response. This determination can include, for example, determining if the response is a correct response, an incorrect response, a partially correct response, or the like. In some embodiments, the determination of response desirability can include generation of a value characterizing the response desirability and the storing of this value in one of the databases 104 such as, for example, the user profile database 301. After the response desirability has been determined, the process 460 proceeds to block 472, wherein an assessment value is generated. In some embodiments, the assessment value can be an aggregate value characterizing response desirability for one or more a plurality of responses. This assessment value can be stored in one of the databases 104 such as the user profile database 301.

Figure 11:
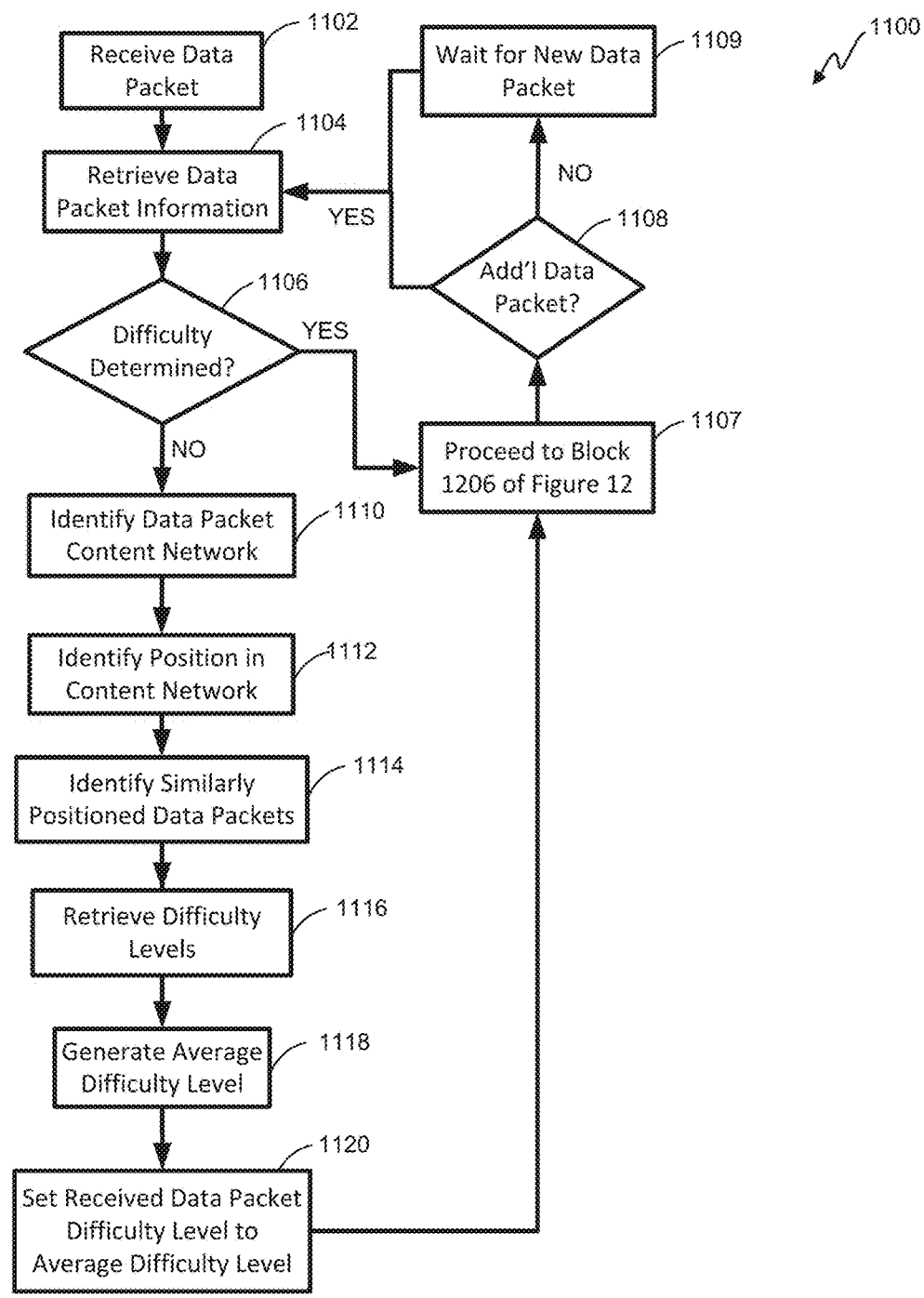
FIG. 11 is a flowchart illustrating one embodiment of a process for automatic difficulty determination of the data packet and placement of that data packet in the content network.

With reference to the FIG. 11, a flowchart illustrating one embodiment of a process 1100 for automatic difficulty determination of the data packet and placement of that data packet in the content network is shown. The process 1100 can be performed by all or components of the content distribution network 100 including by, for example, one or several servers 102. In some embodiments, these one or several servers 102 can comprise one or several remote resources such as can occur via cloud computing or distributed processing. The process 1100 begins at block 1102 when a data packet is received and/or identified. In some embodiments, the data packet can be a data packet for which responses have not been received. In some embodiments, this data packet does not include data metadata identifying one or several attributes of the data packet such as, for example, data packet difficulty level, discrimination level, or the like. In some embodiments, the data packet can be received by the server 102 from another component of the content distribution network 100 such as, for example, the supervisor device 110 or content server 112. In some embodiments, the data packet can be identified by the server 102 from one or several data packets stored in the database server 104 such as in, for example, the content library database 303 of the database server 104.

After the data packet has been received and/or identified, the process 1100 proceeds to block 1104 wherein data packet information, also referred to herein as data packet metadata, is retrieved and/or received. In some embodiments, the data packet metadata can identify one or several attributes of the data packet such as, for example, the difficulty level of all or portions of the data packet, the discrimination level of all or portions of the data packet, or the like. In some embodiments, the data packet metadata can be received with the data packet in block 1102, and in some embodiments, the data packet metadata can be retrieved from the database server 104 and specifically from, for example, the content library database 303 of the database server 104.

After the data packet information has been retrieved, the process 1100 proceeds to block 1106 wherein it is determined if the data packet metadata includes data identifying a difficulty level and/or discrimination level of the data packet. In some embodiments, this can include analyzing the data packet metadata in determining the presence or absence of portions the data packet metadata identifying a difficulty level and/or discrimination level of the data packet. In some embodiments, this determination can be made by the server 102. If it is determined that the data packet metadata contains data packet difficulty information and/or data packet discrimination information, then the process 1100 proceeds to block 1107 and continues to block 1206 of FIG. 12 with the data packet received in block 1102 and continues as described with respect to FIG. 12 below.

The process 1100 continues to decision state 1108 wherein it is determined if any additional data packets have been received or retrieved. If no additional data packets have been received or retrieved, then the process proceeds to block 1109 and waits until a new data packet has been received. After the new data packet has been received, the process 1100 returns to block 1104 and procedures outlined herein. Returning again to decision state 1108, if it is determined that there is an additional data packet, then the process 1100 returns to block 1104 and procedures outlined herein.

Returning again to decision state 1106, if it is determined the difficulty level of the data packet received in block 1102 has not been determined, then the process 1100 proceeds to block 1110 wherein the data packet content network of the received data packet is identified. In some embodiments, for example, the data packet content network can be identified based on information contained in the data packet metadata and information relating to the content network which information relating to the content network is referred to herein as content network metadata. In some embodiments, the information contained in the data packet metadata can identify a subject of the data packet and/or a subject to which the data packet belongs. Similarly, in some embodiments, the content network metadata can identify a subject of the content network and/or tasks, skills, objectives, topics, or the like belonging to the content network. In some embodiments, the information contained in the data packet metadata and in the content network metadata can be retrieved and/or extracted. The information contained in the data packet metadata can then be matched to the information contained in content network metadata to identify the content network to which the data packet belongs. This content network to which the data packet belongs is also referred to herein as the data packet content network. In some embodiments, the identification of the data packet content network can be performed by the server 102 and/or any of the modules are engines of the server 102 or other portion of the content distribution network 100.

After the data packet content network has been identified, the process 1100 proceeds to block 1112 wherein a position in the content network is identified and/or determined for insertion of the data packet received in block 1102. In some embodiments, the position of the content network can be identified based on the data packet metadata and/or the content network metadata. In some embodiments, the position of the content network can be identified and/or selected such that the data packet is placed in the content network with other data packets having similar subjects, topics, skill levels, or the like. This identification can be performed by the server 102 or any other component of the content distribution network 100.

After the position of the content network has been identified, the process 1100 proceeds to block 1114 wherein similarly positioned data packets are identified. In some embodiments, this identification can be performed by retrieving data packets already included in the content network and having subjects, topics, skills, skill levels, or the like identified in their metadata that correspond to those subjects, topics, skills, skill levels, or the like identified in the data packet received in block 1102. In some embodiments, the metadata for the data packets already positioned in the content network can be retrieved from the database server 104 by the server 102, and can be specifically retrieved from the content library database server 303 by the server 102.

After similarly positioned data packets have been identified, the process 1100 proceeds block 1116 wherein attribute information for those one or several similarly positioned data packets is retrieved. In some embodiments, this attribute information can identify, for example, difficulty levels of the similarly positioned data packets, discrimination levels of the similarly positioned data packets, or the like. In some embodiments, this attribute information can be retrieved by retrieving the metadata from the database server 104 for the similarly positioned data packets and extracting the desired attribute information from the retrieved metadata. In some embodiments, the similarly positioned packets for which the metadata is retrieved and for which the attribute information is determined or identified can be the similarly positioned data packets identified in block 1114.

After the attribute information for the similarly positioned data packets has been received and/or retrieved, the process 1100 proceeds to block 1118 wherein a combined attribute value is generated. In some embodiments, this combined attribute value reflects the aggregate of the attribute information retrieved in block 1116. In some embodiments, this combined value can comprise a mean, median, mode, or any other meaningful combined value. In some embodiments, the combined attribute value can comprise an average difficulty level, an average discrimination level, or the like. The combined attribute value can be, in some embodiments, generated by the server 102 or any other desired component of the content distribution network 100.

After the combined attribute value has been determined, the process 1100 proceeds to block 1120 wherein the value of the attribute of the data packet received in block 1102 corresponding to the combined attribute value is set to match the combined attribute value. This can include, for example, setting the difficulty level of the data packet received in block 1102 to the average difficulty level generated in block 1118 for similarly positioned data packets identified in block 1114 when the combined attribute value comprises an average difficulty level. Similarly, this can include setting the discrimination level of the data packet received in block 1102 to the average discrimination level generated in block 1118 for the similarly positioned data packets identified in block 1114 when the combined attribute value comprises an average discrimination level. In some embodiments, the value of the attribute of the data packet received in block 1102 can be set to the average attribute value generated in block 1118 by the server 102 and an indicator of this can be stored in the database server 104 and specifically in the content library database 303. In other words, in some embodiments, the metadata of the data packet received in block 1102 can be updated to reflect an attribute value corresponding to the combined attribute value generated in block 1118. In such an embodiment, the metadata of the data packet received in block 1102 can be updated to have a difficulty level matching the average difficulty level generated in block 1118. After the received packet attribute value has been set to the combined attribute value, the process 1100 returns to block 1107 and proceeds as outlined above.

Figure 12:
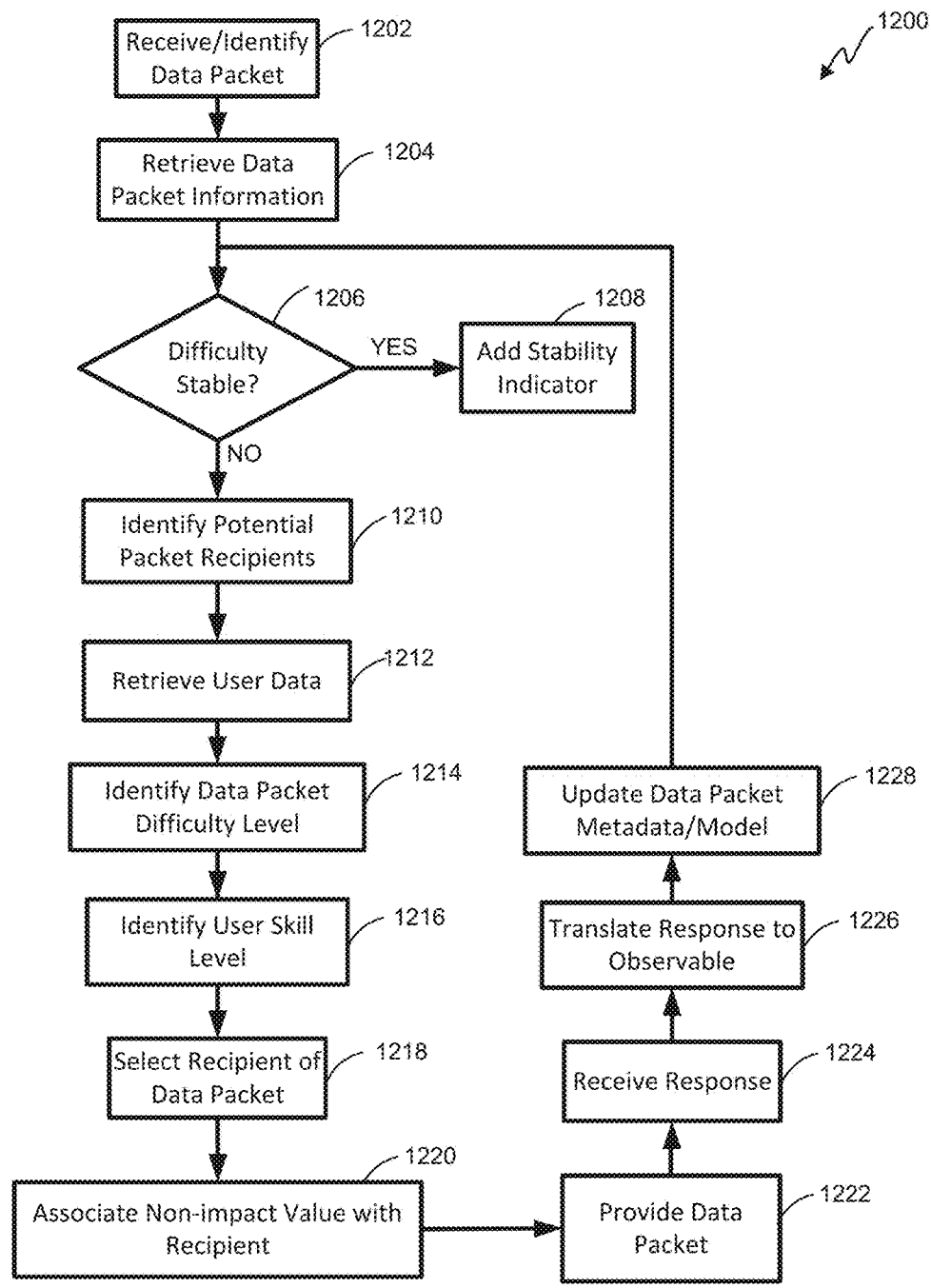
FIG. 12 is a flowchart illustrating one embodiment of a process for data packet metadata stabilization.

With reference now to FIG. 12, a flowchart illustrating one embodiment of a process 1200 for data packet metadata stabilization is shown. The process 1200 can be performed by all or components of the content distribution network 100 including by, for example, one or several servers 102. In some embodiments, these one or several servers 102 can comprise one or several remote resources such as can occur via cloud computing or distributed processing. The process 1200 begins to block 1202 wherein the data packet is received and/or identified. In some embodiments, the data packet can be received from, for example, block 1107 of FIG. 11. In some embodiments, the data packet can be identified from one of the data packet stored in the database 104 specifically in the content library database 303.

After the data packet has been received or identified, process 1200 proceeds to block 1204 wherein data packet information, also referred to herein as data packet metadata is retrieved. In some embodiments, data packet information can be retrieved for the data packet received and/or identified in block 1202. In some embodiments, the data packet metadata can identify one or several attributes of the data packet such as, for example, the difficulty level of all or portions of the data packet, the discrimination level of all or portions of the data packet, or the like. In some embodiments, the data packet metadata can be received with the data packet in block 1202, and in some embodiments, the data packet metadata can be retrieved from the database server 104 and specifically from, for example, the content library database 303 of the database server 104.

After the data packet metadata has been retrieved, the process 1200 proceeds to decision state 1206 where it is determined if one or several attributes identified in the data packet metadata are stable. In some embodiments, for example, the one or several attributes can be identified in the data packet data by one or several values, also referred to herein as attribute values. In some embodiments, for example, one or several of these attribute values can identify the difficulty and/or discrimination of the data packet received and/or identified in block 1202.

In some embodiments, the data packet metadata can include time series data tracking the one or several attribute values over time. In some embodiments, decision state 1206 can include determining whether the one or several attribute values are stable as indicated by their time series data. Alternatively, in some embodiments, the determination of the stability of the attribute values can comprise determining the number of responses received for the data packet received and/or identified in block 1202 and retrieving a threshold, referred to herein as a stability threshold, from the database server 104 and specifically from the threshold database 310 which delineates between stable attribute values and unstable attribute values based on, for example, the number of responses received foreign attribute value. In some embodiments, for example, this threshold can identify a minimum number of responses to be received before an attribute value is identified as stable. In some embodiments, this minimum number of responses can be, for example, 100 responses, 200 responses, 500 responses, 750 responses, 1000 responses, 2000 responses, 5000 responses, 10,000 responses, 50,000 responses, 100,000 responses, and/or any other or intermediate number of responses. In some embodiments, the determined number of responses received for the data packet received and/or identified in a block 1102 can be compared to the stability threshold to determine whether the required minimum number of responses has been received for the data packet identified in block 1202.

If it is determined that the desired number of responses has been received, the process 1200 proceeds to block 1208 wherein a stability indicator is added to the data packet metadata associated with the data packet received and/or identified in block 1202 and/or wherein a stability indicator is stored within the database server 104 in association with the data packet retrieved and/or identified in block 1202. In some embodiments, the stability indicator can comprise one or several values, one of which values can be indicative of the achievement of stability for the attribute values of the data packet received in block 1202. In some embodiments, the adding of a stability indicator can further comprise the generating and sending of an alert to a device such as the supervisor device 110. In some embodiments, this alert can identify the data packet and that the difficulty of the data packet is stable. In some embodiments, the alert can contain other information relevant to the data packet received and/or identified in block 1202.

Returning again to decision state 1206, if it is determined that the difficulty level is not stable, then the process 1200 proceeds to block 1210 wherein one or several potential packet recipients are identified. In some embodiments, the one or several potential packet recipients can be, for example, one or several users belonging to a common cohort. In some embodiments, this common cohort can include registration in one or several groups, classes, courses of study, disciplines, or the like. In some embodiments, identifying the potential packet recipients can include identifying one or several cohorts related to the data packet received and/or identified in block 1202 based on, for example, data packet metadata for the data packet received in block 1202. In some embodiments, the database server 104 can then be queried for information identifying one or several users belonging to these one or several cohorts. In some embodiments, this query can be directed to user profile database 301. The potential packet recipients can, in some embodiments, be identified by the server 102.

In some embodiments, the set of potential packet recipients can comprise users requesting a next data packet or an additional data packet. In some embodiments, the set of potential packet recipients can be formally identified in that some potential packet recipients are designated as belonging to this set of potential packet recipients and/or in that this set of potential packet recipients exists in, for example, the database server 104. In some embodiments, this set of potential packet recipients can merely comprise the group of users requesting a next packet, and specifically requesting a next packet that can include the data packet identified in block 1202.

After the potential packet recipients have been identified, the process 1200 proceeds to block 1212, wherein user data for the potential packet recipients is retrieved and/or received. In some embodiments, this user data can comprise the metadata for each of the users in the group of potential packet. This metadata can be received from the database server 104 and specifically from the user profile database 301 by the server 102 upon query of the user profile database 301 for that metadata by the server 102.

After the user data has been retrieved, the process 1200 proceeds to block 1214 wherein a data packet attribute value is identified. In some embodiments, the data packet attribute value can be one or several values that can characterize a difficulty level of the data packet received in block 1202 and/or that can characterize the discrimination level of the data packet received in block 1202. In some embodiments, the data packet metadata can be retrieved in the database server 104 and specifically from the content library database 303. In some embodiments, as the data packet metadata has already been retrieved in block 1204, block 1214 can include extracting one or several attribute values from that metadata.

After the data packet attribute value has been identified, the process 1200 proceeds block 1216 wherein a user attribute value is identified. In some embodiments, the user attribute value can be one or several values that characterize, for example, the skill level of the user, a learning style of the user, or the like. In some embodiments, the user attribute value can be identified from user metadata that can be retrieved from the database server 104 and specifically from the user profile database 301.

After the skill level has been identified, the process 1200 proceeds to block 1218 wherein a recipient of the data packet is selected. In some embodiments, the recipient is the user who will receive the data packet received and/or identified in block 1202. In some embodiments, the recipient of the data packet can be selected based on, for example, comparison of one or several data packet attribute values in one or several user attribute values. The recipient of the data packet can be selected by the server 102.

After the recipient of the packet has been selected, the process 1200 proceeds to block 1220 wherein a non-impact value is associated with the recipient. In some embodiments, the non-impact value identifies the data packet received in block 1202 and selected for delivery to the recipient selected in block 1218 as excluded from calculations of user attribute values. In some embodiments, for example, because instability of the attribute values of the data packet as determined in decision state 1206, modifications to the user metadata with results of a user response relating to the data packet would be unreliable. Accordingly, the non-impact value is associated with the recipient and the data packet to be provided to the recipient so that the recipient's user metadata is not modified based on the result of any response provided by the recipient. In some embodiments, the non-impact value can be associated with the recipient by storing the non-impact value in the database server 104 and specifically in the user profile database 301. In some embodiments, the non-impact value can be further associated with the data packet received in block 1202 by storing the non-impact value in the content library database 303 and linked to the data packet received in block 1202.

After the nonimpact value has been associated with the recipient, the process 1200 proceeds to block 1222 wherein the data packet is provided to the recipient. In some embodiments, the data packet can be provided to the recipient via the user device 106, and specifically by providing the data packet to the presenter module 672 which can then provide the data packet to the view module 674 which can use the I/O subsystem 526 to provide the data packet and/or portions of the data packet to the user of the user device 106.

After the data packet has been provided, the process 1200 proceeds block 1224 wherein the responses received. In some embodiments, the responses received from the user by the server 102. Specifically, the user can provide a response to the data packet provided in block 1222 at the user device 106 via the I/O subsystem 526 which can pass the response to the view module 674. To view module can then provide the response the presenter module 672, and bus the response can be received by the server 102.

After the responses have been received, the process 1200 proceeds to block 1226 wherein the responses are translated into an observable. In some embodiments, the response translated into an observable is the response received in block 1224, which response is provided by the recipient subsequent to receiving the data packet. In some embodiments, translating the received response into an observable includes evaluating the received response to determine if the received response includes one or several attributes, or alternatively evaluating the received response to determine if the received response is a desired response. In some embodiments, the response can be translated into an observable by the response system 406 and/or the response processor 678.

After the response has been translated into an observable, the process 1200 proceeds to block 1228, wherein the data packet metadata and/or data packet model is updated. In some embodiments, the data packet metadata and/or data packet model associated with the data packet provided in block 1222 can be updated based on the observable generated in block 1226 via the translation of the response received in block 1224. In some embodiments, this can include updating one or several data packet attribute values contained in the data packet metadata, and specifically can include updating a difficulty level of the data packet according to whether the response received in block 1224 was correct or incorrect. In some embodiments, the data packet metadata and/or data packet can be updated by the summary model system 404 and/or the model engine 682. The details of the updating of the data packet metadata and/or data packet model will be discussed in greater detail with respect to the process 1400 of FIG. 14 below. After the data packet metadata and/or data packet model has been updated, the process 1200 returns to decision state 1206 and proceeds as outlined above.

Figure 13:
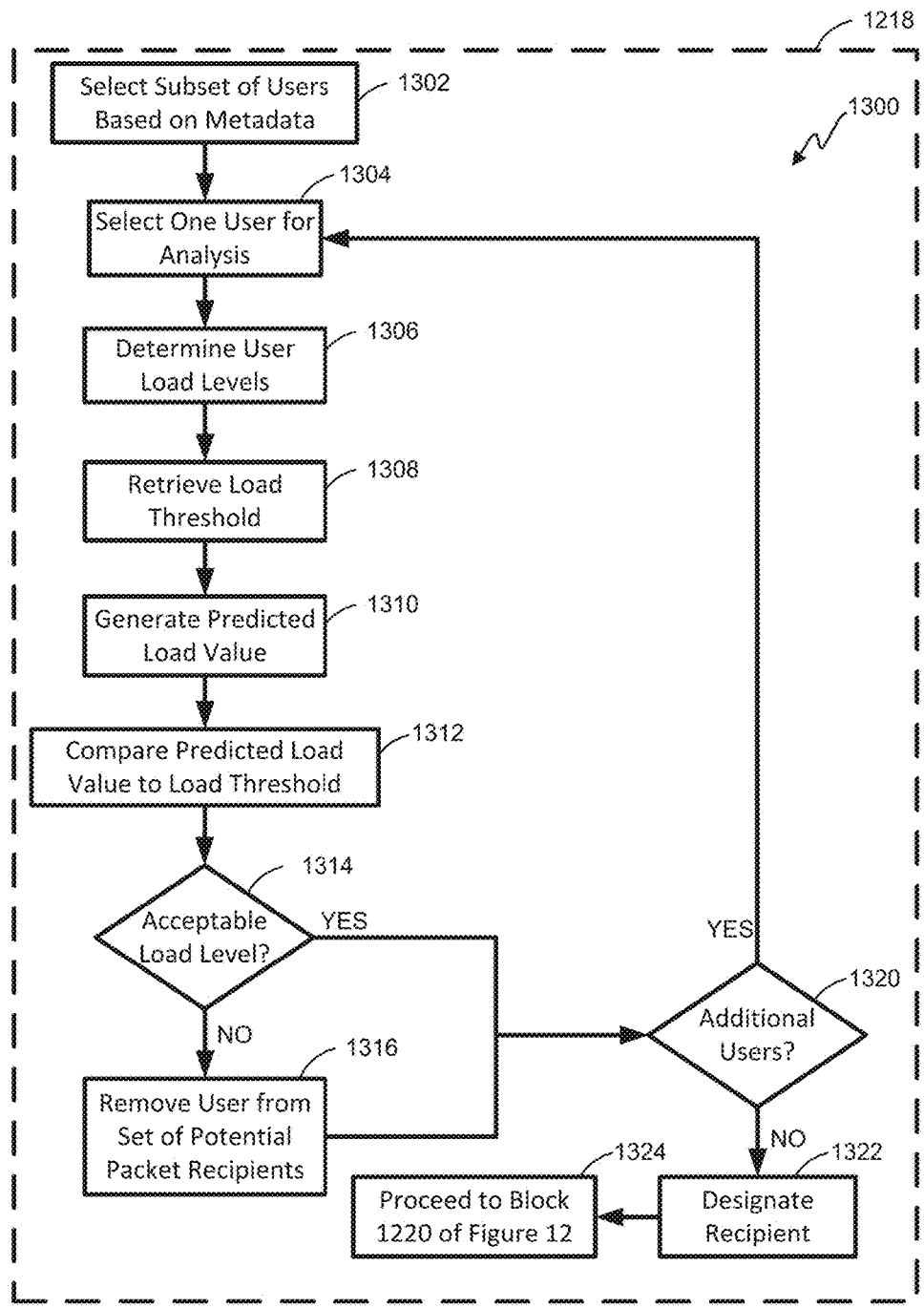
FIG. 13 is a flowchart illustrating one embodiment of a process for selecting recipient of the data packet.

With reference to FIG. 13, a flowchart illustrating one embodiment of a process 1300 for selecting recipient of the data packet shown. In some embodiments, the process 1300 can be performed in the place of as a part of block 1218 of FIG. 12. The process 1300 can be performed by any component of the content distribution network 100 including, for example, the server 102. The process begins at block 1302 wherein a subset of users is selected. In some embodiments, the subset of users selected is based on only portions of the data packet metadata of the data packet received in block 1202 and/or the user metadata. In some embodiments, the subset of users can be selected from the potential packet recipients identified in block 1210 of FIG. 12. In some embodiments, the subset of users can be selected by identifying one or several users within the group of potential packet recipients having a skill level corresponding to and/or matching the difficulty level and/or the discrimination level of the data packet received in block 1202.

After the subset of users has been selected, the process 1300 proceeds to block 1304 wherein one of the subset of users is selected for analysis in some embodiments, the selected one of the subset of users can be the user that has not been previously selected for analysis. In some embodiments, the selecting one user for analysis can include identifying the users in the subset of users that have not been previously selected for analysis and then selecting one of those identified users. In some embodiments, when a user is selected for analysis, a value indicative of selection can be associated with that user. The one of the subset users can, in some embodiments, be selected by the server 102.

After one of the subset of users has been selected for analysis, process 1300 proceeds to block 1306 wherein user load levels of the selected user are determined. In some embodiments, the user load levels can comprise data that can be contained in the user metadata and that can identify, for example, the amount of time, or the number of data packets for a user to complete a task relating to the data packet received in block 1202. In some embodiments, determining the user load levels can comprise extracting this information from the user metadata with, for example, the server 102. After the user load levels have been determined, the process 1300 proceeds to block 1308 wherein a load threshold is retrieved. In some embodiments, below threshold delineates between acceptable load levels and unacceptable load levels. The low threshold can be stored in the database server 104, and specifically in the threshold database 310.

In some embodiments, the load threshold can be generic. In some embodiments the load threshold can be specific to, for example, one or several data packets, courses, tasks, or the like. In some embodiments, the load threshold retrieved in block 1308 can be relevant to the data packet received in block 1202.

After the load threshold has been retrieved, the process 1300 proceeds to block 1310 wherein a predicted load value is generated. In some embodiments, the predicted load value can comprise the load level determined in block 1306 adjusted to reflect inclusion of the data packet received in block 1202. In some embodiments, this can measure and/or predict the user load level if the data packet received in block 1202 is provided to the user, or in other words, if that user is selected as the recipient. In some embodiments, the predicted load value can be generated by the server 102.

After the predicted load value has been generated, the process 1300 proceeds to block 1312 when the predicted load value is compared to the load threshold. In some embodiments, this comparison can include associating a first value with the user selected in block 1304 if the comparison of the load value and the load threshold indicates an acceptable load level and the second value can be associated with the user selected in block 1304 if the comparison of the load value and the load threshold indicates an unacceptable load level. In some embodiments, the predicted load value can be compared to the load threshold by the server 102.

After the predicted load value has been compared to the load threshold, the process 1300 proceeds to decision state 1314 wherein it is determined if the load level is acceptable. In some embodiments, this can include determining if the first value or the second value is associated with the user selected in block 1304. If the second value is associated with the user selected in block 1304 and the load level is thus unacceptable, then the process 1300 proceeds to block 1316 and the user selected in block 1304 is removed from the set of potential packet recipients.

After the user has been removed from the set of potential packet recipients, returning again to decision state 1314, if it is determined that the load level is acceptable, then the process 1300 proceeds to decision state 1320 wherein it is determined if there are additional users. In some embodiments, this can include determining if there are additional, unselected users in the subset of users selected in block 1302. If it is determined that there are additional, unselected users, then the process 1300 returns to decision state 1304 and proceeds as outlined above.

If it is determined there no additional users, than the process 1300 proceeds to block 1322 wherein a recipient is designated. In some embodiments, this can include determining whether any of the users in the set of potential users is associated with a first value indicative of an acceptable load level. If only a single user is associated with the first value indicative of an acceptable load level, then that single user is designated as the recipient by the server 102. If multiple users are associated with the first value indicative of an acceptable vote level, then one of those multiple users can be designated as the recipient. In some embodiments, for example, this one of the multiple users can be randomly selected from the multiple users that are associated with the first value by, for example the server, and in some embodiments, this one of the multiple users can be selected based on the closeness of the match between the attribute values of the data packet received in block 1202 and attribute values of the users, the degree to which users' predicted load levels are acceptable, or the like. After the recipient has been designated, the process 1300 proceeds to block 1324 and continues at block 1220 of FIG. 12.

Figure 14:
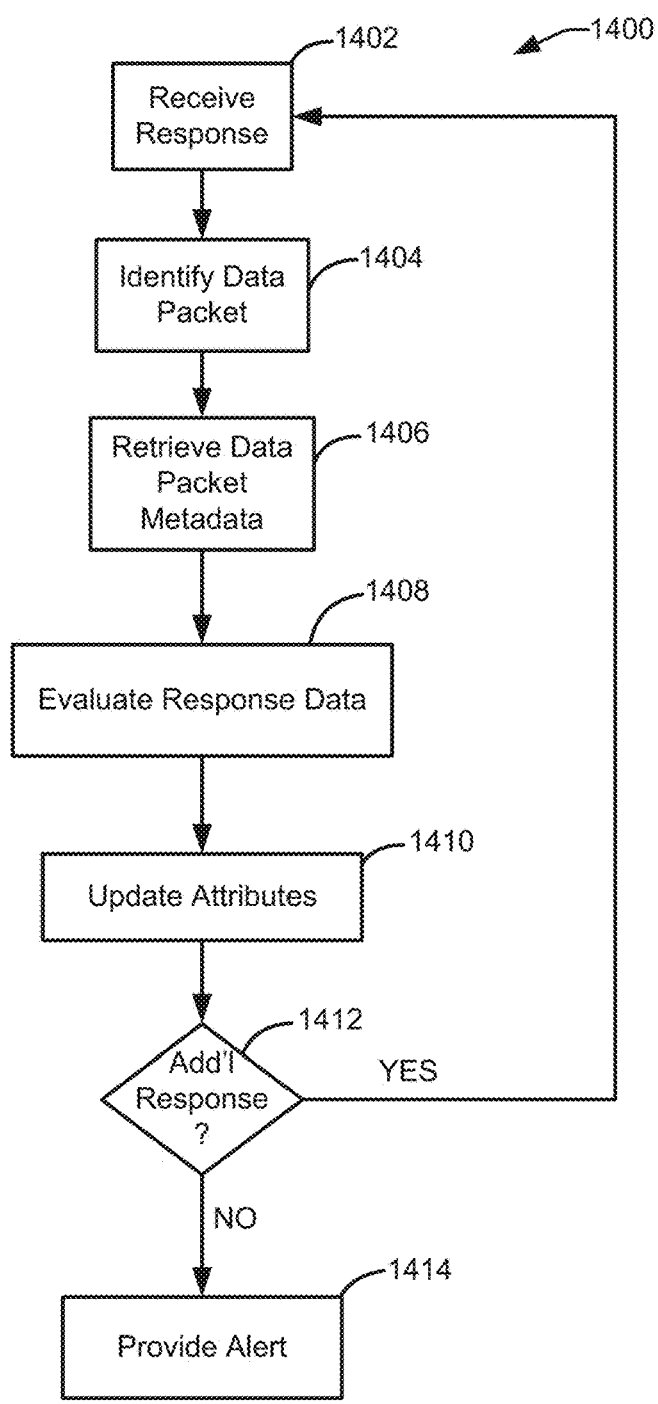
FIG. 14 is a flowchart illustrating one embodiment of a process for automatically updating data packet metadata and/or automatically updating a data packet model.

With reference now to FIG. 14, a flowchart illustrating one embodiment of a process 1400 for automatically updating data packet metadata and/or automatically updating a data packet model is shown. In some embodiments, the process 1400 can be performed as a part of or in place of the step of block 1228 of FIG. 12, and in some embodiments, the process 1400 can be performed independent of the process of FIG. 12. The process 1400 can be performed by the server 102, and specifically by, for example, the response system 406, the response processor 678, the summary model system 404 and/or the model engine 682. The process 1400 begins at block 1402 wherein a response is received. In some embodiments, the response can be received from a user device 106 via the I/O subsystem 526, the communication subsystem 532, the communications network 102, the view module 674, and/or the presenter module 672. In some embodiments, the response can be associated with a previously provided data packet that can be selected for the user based on one or several of the user metadata, the data packet metadata, or the like.

After the responses have been received, the process 1400 proceeds to block 1404 wherein the data packet associated with the received responses is identified. In some embodiments, for example, the response can include information relating to the data packet prompting the response. In some embodiments, for example, this information can be extracted from the response and can be used to identify the data packet provided to the user previous to the response and giving rise to the response. In some embodiments, the data packet can be identified by the server 102.

After the data packet has been identified, the process 1400 proceeds to block 1406 wherein the data packet metadata is retrieved. In some embodiments, the data packet metadata can comprise information relating to one or several attributes of the data packet. In some embodiments, the data packet metadata can be associated with the data packet identified in block 1404 and the data packet metadata can be retrieved from the database server 104 and specifically from the content library database 303.

In some embodiments, the one or several attributes can be represented and/or determined through one or several models, such as statistical models. In some embodiments, these models can be continuously or periodically updated by the content distribution network 100 when one or several new responses are received. In some embodiments, these models can be stored in, for example, the user profile database 301, the content library database 303, the model database 309, or any of the other databases 104. In some embodiments, a model can be associated with a single objective such that the model is not applicable to other objectives, and in some embodiments, the model can be associated with a plurality of objectives.

In some embodiments, a user skill level and/or a data packet difficulty level can be determined via a model such as a statistical model based on, for example, a localized distribution including, for example, a Gaussian distribution, a Beta distribution or a Beta family distribution, a Log normal distribution, or the like. In some embodiments, the data packet difficulty can be determined from the mode of a localized distribution such as the mode of a Gaussian distribution and/or a piece-wise Gaussian distribution, and a user skill level can likewise be determined from the mode of a localized distribution such as the mode of a Gaussian distribution and/or a piece-wise Gaussian distribution.

Figure 15:
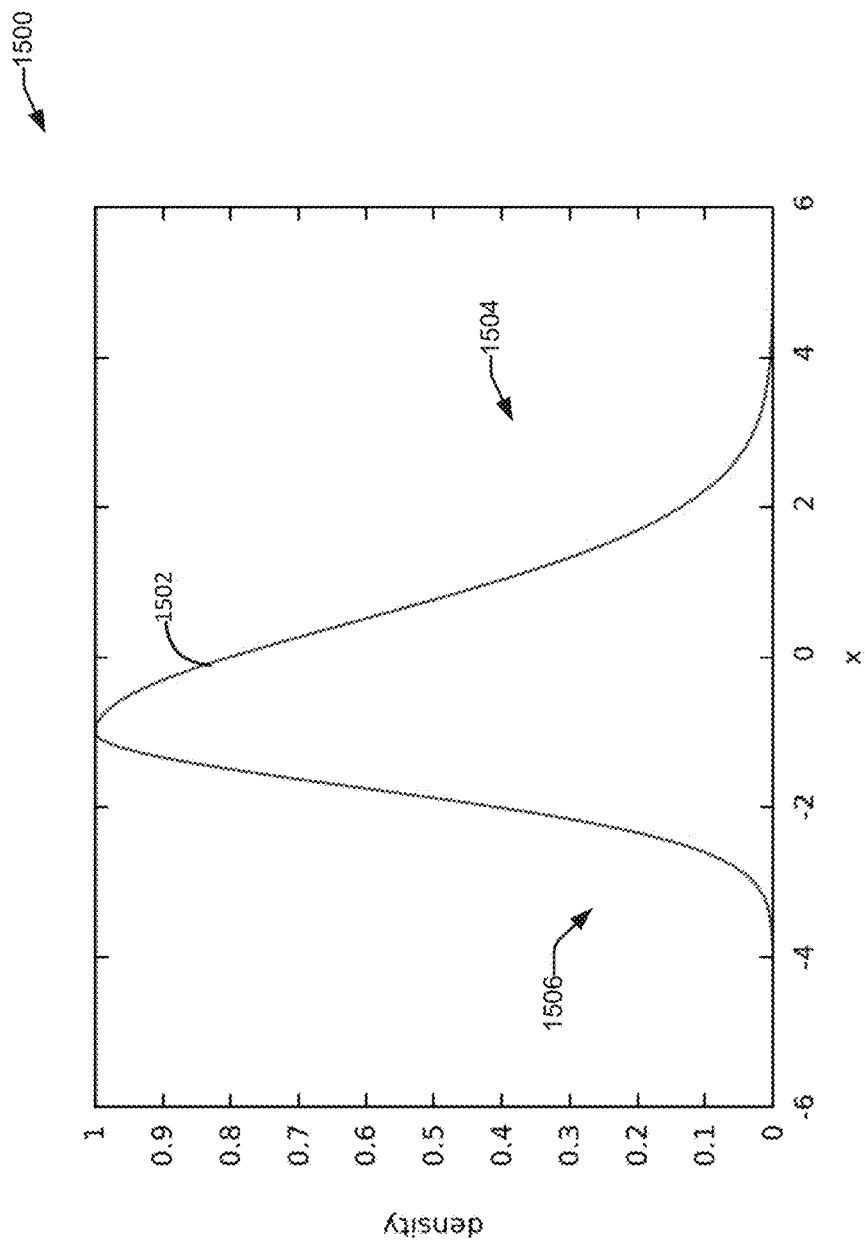
FIG. 15 is an illustration of one embodiment of a piecewise Gaussian distribution.

One example of a piece-wise Gaussian distribution 1500 is shown in FIG. 15. As seen in FIG. 9, the piece-wise Gaussian distribution 1500 has an x-axis labelled "x" and a y-axis labelled "density." As depicted in FIG. 15, the units of the x-axis indicate a skill level of the user(s) associated with the piecewise Gaussian distribution 1500, with the skill level increasing in a positive correlation with the values of the x-axis. The units of the y-axis, density, indicate a density that describes the likelihood of a random variable selected according to the piecewise Gaussian distribution 1500 to take on a value on the x-axis.

The piecewise Gaussian distribution 1500 includes a curve 1502 that has a first piece 1504 forming the right side of the piecewise Gaussian distribution 1500, and a second piece 1506 forming the left side of the piecewise Gaussian distribution 1500. In some embodiments, the mode of the piecewise Gaussian distribution 1500 can represent the skill level of the user and/or the difficulty level of the data packet.

In some embodiments, the property of the Gaussian distribution, such as, for example, the width of the Gaussian distribution or of the piecewise Gaussian distribution can represent or positively correlate to the level of certainty, and/or can be used to determine an error value. In some embodiments, the level of uncertainty and/or an error value can be mathematically calculated based on one or several variables and/or parameters tied to the Gaussian distribution and/or the piecewise Gaussian distribution 1500.

In some embodiments, the piecewise Gaussian distribution 1500 can further include a first level of certainty and/or first error value associated with the first piece 1504 of the piecewise Gaussian distribution 1500, and a second level of certainty and/or a second error value associated with the second piece 1506 of the piecewise Gaussian distribution 1500. In such embodiments, the width of the Gaussian distribution and/or piecewise Gaussian distribution 1500, and/or the width of one or both of the pieces 1504, 1506 of the piecewise Gaussian distribution 1500 can vary in a positive relation with the level of uncertainty and/or with the error value. Thus, as the width decreases, the level of uncertainty and/or the error value decreases, and as the width increases, the level of uncertainty and/or the error value increases.

In some embodiments, the first piece 1504 and the second piece 1506 can have different properties to represent different traits of one or several users and/or of one or several data packets. Specifically, and as seen in FIG. 15, the tail of the first piece 1504 of the piecewise Gaussian distribution 1500 extend farther than the tail of the second piece 1506 of the piecewise Gaussian distribution 1500. In some embodiments, this serves to provide a semi-ratcheting effect to changes to the piecewise Gaussian distribution 1500 when either desired responses or undesired responses are received. Specifically, this semi-ratcheting effect results in a user's skill level and/or the difficulty level of a data packet more quickly increasing when a desired response is received than decreasing when an undesired response is received. This can, in some embodiments, correlate to the user property of accepting data, or more specifically, gaining knowledge faster than losing knowledge.

Figure 16:
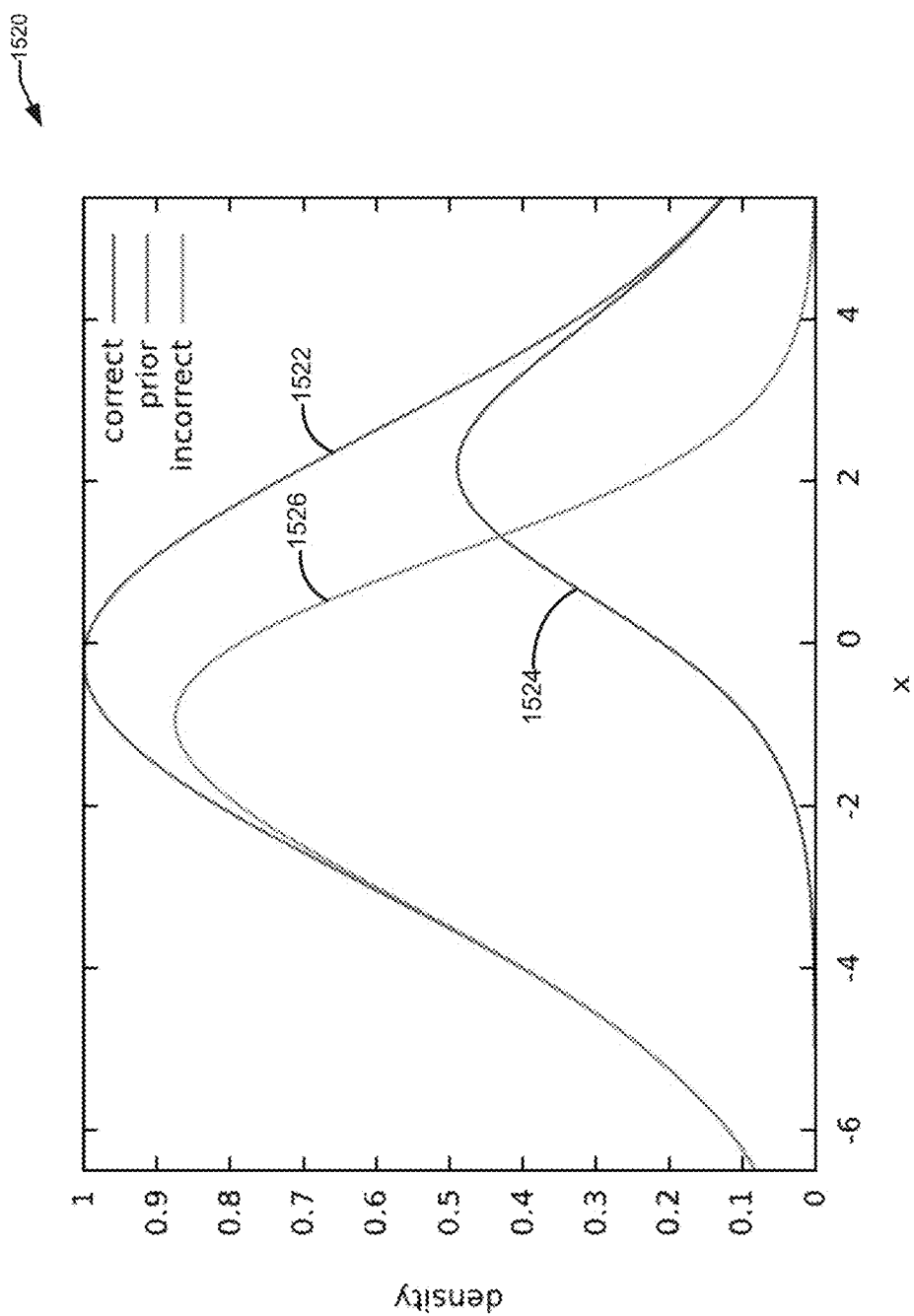
FIG. 16 is an illustration of a plurality of piecewise Gaussian distributions.

This semi-ratcheting effect is illustrated in FIG. 16 which depicts a plurality of piecewise Gaussian distributions 1520. The plurality of piecewise Gaussian distributions 1520 includes a prior distribution 1522, a correct distribution 1524, which is the Gaussian distribution resulting from receipt of a desired response to an assessment data packet, and an incorrect distribution 1526, which is the piecewise Gaussian distribution resulting from receipt of an undesired response to an assessment data packet.

As depicted in FIG. 16, the prior response has a mode of −0.2, and thus depicts a user skill level and/or data packet difficulty level of −0.2. This skill level and/or data packet difficulty level shifts, in response to the received desired response to 2.2, and shifts, in response to the received undesired response of −1.5. Thus, the semi-ratcheting effect of the piecewise Gaussian distribution is that the skill level and/or data packet difficulty level increases a total of 2.5 as a result of the received desired response and only decreases a total of 1.3 as a result of the received undesired response. As further seen, each of the correct and incorrect distributions 1524, 1526 is narrower than the prior distribution 1522, indicating lower levels of uncertainty and greater levels of certainty associated with those models. In some embodiments, the degree to which the width of the piecewise Gaussian distribution 1500 can shrink can be limited. In some embodiments, for example, the first piece 1504 of the piece-wise Gaussian distribution 1500 can be prohibited from having a scale factor smaller than, for example, approximately: 3.0; 2.5; 2.0; 1.75; 1.5; 1.25; 1.0; 0.75; 0.5; 0.25; and/or any other or intermediate value, and in some embodiments, for example, the second piece 1506 of the piece-wise Gaussian distribution 1500 can be prohibited from having a scale factor smaller than, for example, approximately: 3.0; 2.5; 2.0; 1.75; 1.5; 1.25; 1.0; 0.75; 0.5; 0.25; 0.15; 0.1; 0.05; and/or any other or intermediate value. As used herein, "approximately" identifies a range about the therewith associated value, which range is +/−25%, 20%, 15%, 10%, 5%, and/or any other or intermediate percent of that therewith associated value.

Returning again to FIG. 14, after the data packet metadata has been retrieved, the process 1400 proceeds to block 1408 wherein the response data is evaluated. In some embodiments, this can include the translation of the response into an observable by, for example, the response processor 678. In some embodiments, this translation of the response into an observable can include determining whether the response is a desired response or an undesired response. Evaluation the response can be performed by the response processor 678 based on answer data associated with the data packet and, in some embodiments, stored in the content library database 303.

After the response data has been evaluated, the process 1400 proceeds to block 1410 wherein one or several attribute values of the data packet for which the response is received in block 1402 are updated. In some embodiments, this can include updating the user attributes to reflect a new skill level and/or new confidence level or error value, and in some embodiments, this can include updating the objective and/or data packet data to reflect a new difficulty level and/or new confidence level or error value. In some embodiments, the date of attributes in block 1410 can include the updating of both user attributes and data packet attributes unless the user associated with the response received in block 1402 is associated with a non-impact value as can be generated in block 1220 of FIG. 12.

In some embodiments, the user data and/or data packet data can be updated to reflect the desired or undesired response received. In some embodiments in which the user provides an undesired response, the user skill level can stay the same and/or be negatively changed and/or the data packet difficulty level can increase and/or stay the same, and in some embodiments in which the user provides the desired response, the user skill level can positively change and/or the data packet difficulty level can decrease and/or stay the same. In some embodiments, the user skill level can be changed according to one or several predictive models which can be, for example, one or several probabilistic models.

In some embodiments in which one or several user attributes and/or objective or data packet attributes are modeled according to a localized distribution such as a Gaussian distribution and/or a piecewise Gaussian distribution, these models can be updated using a mathematical approach including, for example, a Bayesian approach. In such an embodiment, the updated model 1524, 1526 can be determined based on the combination of prior model 1522 and the calculated probability of the user providing the desired response to the provided data packet. Thus, in some embodiments, the prior model can be adjusted based on the skill level and/or difficulty level most likely correlating to the received response. In some embodiments, this adjustment can be limited to within the error function and/or error value so as to stabilize the change to the prior model.

In one embodiment, for example, the likelihood of the user providing the desired response can be based on the user skill level and/or the difficulty of the data packet, and can be determined using an Item Response Theory ("IRT") model such as, for example, a Rasch model and/or a sigmoid and/or logistic curve. This probability of correctly answering the question can be input into, for example, a Gaussian model of the student skill level, which Gaussian model can be updated according to a Bayesian technique to estimate a new student skill level and/or a new data packet difficulty level.

After the additional data has been updated, the process 1400 proceeds to decision state 1412, wherein it is determined if there are any additional responses. In some embodiments, this can include determining whether there are any other responses received for the data packet identified in block 1404. If there are additional responses, then the process returns to block 1402 and proceeds as outlined above. If there are no additional responses then the process 1400 proceeds to block 1414, wherein an alert is generated and sent to, for example, the supervisor device 110. In some embodiments, this alert can be generated and sent as described above. In some embodiments, this alert can comprise information identifying, for example, the occurrence of the update to the attributes and/or data identifying the effect of the update.

In some embodiments, and in the place of providing the alert, the process 1400 at step 1414 can return to decision state 1206 and proceed as outlined above. Alternatively, in other embodiments, the process 1400 at step 1414 can provide the data packet identified in block 1404 to one or several users based on the updated attribute information.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein, the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read-only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for content provisioning via the automatic determination of a content attribute, the system comprising:
   memory comprising:
      a content database comprising a plurality of data packets and metadata identifying an attribute of an associated data packet, wherein each of the plurality of data packets is associated with unique metadata;
      a user profile database comprising user history data identifying an attribute of an associated user, wherein each user is associated with unique user history data;
   a user device comprising:
      a first network interface configured to exchange data via a communication network; and a first I/O subsystem configured to convert received digital communication to user interpretable outputs via a user interface; and one or more servers communicatingly coupled with the memory and the user device, wherein the server is configured to:
- receive a response from a user via a user device, wherein the response is to a previously provided data packet;
- identify the previously provided data packet;
- retrieve data packet metadata, wherein the packet metadata comprises at least one attribute value identifying an attribute of the data packet, wherein the data packet metadata comprises a model based on a Gaussian distribution, wherein the Gaussian distribution is defined in part by an error value corresponding to a width of the Gaussian distribution;
- translate the received response into an observable;
- update the data packet metadata based on the observable; and
- provide the data packet to another user based on the updated data packet metadata.

2. The system of claim 1, wherein the model is a model of the difficulty level of the data packet.

3. The system of claim 1, wherein the Gaussian distribution comprises a piecewise Gaussian distribution.

4. The system of claim 1, wherein the mode of the Gaussian distribution corresponds to a difficulty level of the data packet.

5. The system of claim 1, wherein updating the update the data packet metadata based on the observable comprises updating the Gaussian distribution.

6. The system of claim 5, wherein updating the Gaussian distribution comprises updating the mode of the Gaussian distribution and the error value of the Gaussian distribution.

7. The system of claim 6, wherein the update of the Gaussian distribution varies based on whether the received response is a desired response or an undesired response.

8. The system of claim 7, wherein providing the received data packet to the user device based on the updated data packet metadata of the received data packet comprises selecting a recipient of the received data packet.

9. The system of claim 8, wherein the recipient of the received data packet is selected based on a comparison of the data packet metadata and user metadata associated with the recipient.

10. A method for automatically updating data packet metadata comprising:
- receiving a response from a user via a user device, wherein the response is to a previously provided data packet;
- identifying the previously provided data packet;
- retrieving data packet metadata, wherein the packet metadata comprises at least one attribute value identifying an attribute of the data packet, wherein the data packet metadata comprises a model based on a Gaussian distribution, wherein the Gaussian distribution is defined in part by an error value corresponding to a width of the Gaussian distribution;
- translating the received response into an observable;
- updating the data packet metadata based on the observable; and
- providing the data packet to another user based on the updated data packet metadata.

11. The method of claim 9, wherein the data packet metadata comprises a model of the difficulty level of the data packet.

12. The method of claim 11, wherein the mode of the Gaussian distribution corresponds to a difficulty level of the data packet.

13. The method of claim 12, wherein the Gaussian distribution comprises a piecewise Gaussian distribution.

14. The method of claim 10, wherein updating the update the data packet metadata based on the observable comprises updating the Gaussian distribution.

15. The method of claim 14, wherein updating the Gaussian distribution comprises updating the mode of the Gaussian distribution and the error value of the Gaussian distribution.

16. The method of claim 15, wherein the update of the Gaussian distribution varies based on whether the received response is a desired response or an undesired response.

17. The method of claim 16, wherein providing the received data packet to the user device based on the updated data packet metadata of the received data packet comprises selecting a recipient of the received data packet, and wherein the recipient of the received data packet is selected based on a comparison of the data packet metadata and user metadata associated with the recipient.

* * * * *